United States Patent [19]

Skolnick et al.

[11] Patent Number: 5,747,282

[45] Date of Patent: May 5, 1998

[54] 17Q-LINKED BREAST AND OVARIAN CANCER SUSCEPTIBILITY GENE

[75] Inventors: Mark H. Skolnick; David E. Goldgar; Yoshio Miki; Jeff Swenson; Alexander Kamb; Keith D. Harshman; Donna M. Shattuck-Eidens; Sean V. Tavtigian, all of Salt Lake City, Utah; Roger W. Wiseman; P. Andrew Futreal, both of Durham, N.C.

[73] Assignees: Myraid Genetics, Inc.; University of Utah Research Foundation, both of Salt Lake City, Utah; The United States of America as represented by the Secretary of Health and Human Services, Washington, D.C.

[21] Appl. No.: 483,554

[22] Filed: Jun. 7, 1995

Related U.S. Application Data

[63] Continuation-in-part of Ser. No. 409,305, Mar. 24, 1995, abandoned, which is a continuation-in-part of Ser. No. 348,824, Nov. 29, 1994, abandoned, which is a continuation-in-part of Ser. No. 308,104, Sep. 16, 1994, which is a continuation-in-part of Ser. No. 300,266, Sep. 2, 1994, abandoned, which is a continuation-in-part of Ser. No. 289,221, Aug. 12, 1994, abandoned.

[51] Int. Cl.$^6$ .............................. C12P 21/06; C12Q 1/68; C07H 21/04

[52] U.S. Cl. .................. 435/69.1; 435/6; 435/320.1; 435/325; 536/23.5; 536/24.31; 536/24.33; 935/9; 935/60; 935/66

[58] Field of Search .................. 536/23.1, 23.5, 536/24.33; 435/69.1, 6, 7.1, 91.1, 91.2, 375, 320.1; 514/44

[56] References Cited

PUBLICATIONS

E. Marshall (1995) Science 269:1050–1055.
Vila et al (1995) Targeted Gene Therapy 9:190–199.
Molecular Biology of the Gene, 4th Edition, vol. 1 Eds. J. D. Watson et al., 1987, p. 313.

*Primary Examiner*—Bruce R. Campell
*Assistant Examiner*—Abdur Razzaque
*Attorney, Agent, or Firm*—Venable, Baetjer, Howard & Civiletti, LLP

[57] ABSTRACT

The present invention relates generally to the field of human genetics. Specifically, the present invention relates to methods and materials used to isolate and detect a human breast and ovarian cancer predisposing gene (BRCA1), some mutant alleles of which cause susceptibility to cancer, in particular breast and ovarian cancer. More specifically, the invention relates to germline mutations in the BRCA1 gene and their use in the diagnosis of predisposition to breast and ovarian cancer. The present invention further relates to somatic mutations in the BRCA1 gene in human breast and ovarian cancer and their use in the diagnosis and prognosis of human breast and ovarian cancer. Additionally, the invention relates to somatic mutations in the BRCA1 gene in other human cancers and their use in the diagnosis and prognosis of human cancers. The invention also relates to the therapy of human cancers which have a mutation in the BRCA1 gene, including gene therapy, protein replacement therapy and protein mimetics. The invention further relates to the screening of drugs for cancer therapy. Finally, the invention relates to the screening of the BRCA1 gene for mutations, which are useful for diagnosing the predisposition to breast and ovarian cancer.

20 Claims, 18 Drawing Sheets

Map of the early onset breast and ovarian cancer region (BRCA1)

| SEQ. ID NO: | | |
|---|---|---|
| 82 | BRCA1 | CPICLELIKEPVSTK-CDHIFCKFCMLKLLNQKK---GPSQCPLCK |
| 83 | RPT1 | CPICLELLKEPVSAD-CNHSFCRACITLNYESNRNTDGKGNCPVCR |
| 84 | RIN1 | CPICLDMLKNTMTTKECLHRFCSDCIVTALRS-----GNKECPTCR |
| 85 | RFP1 | CPVCLQYFAEPMMLD-CGHNICCACLARCWGTAC---TNVSCPQCR |
|  | C3HC4 motif | C--C------------C-H--C--C-----------------C--C |

```
   1  gaggctagagggcaggcactttatggcaaactcaggtagaattcttcctcttccgtctct
  61  ttcctttacgtcatcggggagactgggtggcaatcgcagcccgagagacgcatggctct
 121  ttctgccctccatcctctgatgtaccttgatttcgtattctgagaggctgctgcttagcg
 181  gtagcccttggtttccgtggcaacggaaaagcgcgggaattacagataaattaaaactg
 241  cgactgcgcggcgtgAGCTCGCTGAGACTTCCTGGACCCCGCACCAGGCTGTGGGGTTTC
 301  TCAGATAACTGGGCCCCTGCGCTCAGGAGGCCTTCACCCTCTGCTCTGGGTAAAGgtagt
 361  agagtcccgggaaagggacaggggggcccaagtgatgctctggggtactggcgtgggagag
 421  tggatttccgaagctgacagatgggtattctttgacgggggtaggggcggaacctgaga
 481  ggcgtaaggcgttgtgaaccctggggagggggggcagtttgtaggtcgcgagggaagcgct
 541  gaggatcaggaaggggcactgagtgtccgtgggggaatcctcgtgataggaactggaat
 601  atgccttgaggggggacactatgtctttaaaaacgtcggctggtcatgaggtcaggagttc
 661  cagaccagcctgaccaacgtggtgaaactccgtctctactaaaaatacnaaaattagccg
 721  ggcgtggtgccgctccagctactcaggaggctgaggcaggagaatcgctagaacccggga
 781  ggcggaggttgcagtgagccgagatcgcgccattgcactccagcctgggcgacagagcga
 841  gactgtctcaaaacaaaacaaaacaaaacaaaacaaaaacaccggctggtatgtatgag
 901  aggatgggaccttgtggaagaagaggtgccaggaatatgtctgggaaggggaggagacag
 961  gatttgtgggagggagaacttaagaactggatccatttgcgccattgagaaagcgcaag
1021  agggaagtagaggagcgtcagtagtaacagatgctgccggcagggatgtgcttgaggagg
1081  atccagagatgagagcaggtcactgggaaaggttaggggcggggaggccttgattggtgt
1141  tggtttggtcgttgttgattttggttttatgcaagaaaaagaaaacaaccagaaacattg
1201  gagaaagctaaggctaccaccacctacccggtcagtcactcctctgtagctttctctttc
1261  ttggagaaaggaaaagacccaaggggttggcagcgatatgtgaaaaaattcagaatttat
1321  gttgtctaattacaaaaagcaacttctagaatctttaaaaataaaggacgttgtcattag
1381  ttcttctggtttgtattattctaaaaccttccaaatcttcaaatttactttatttaaaa
1441  tgataaaatgaagttgtcatttataaaccttttaaaaagatatatatatatgttttct
1501  aatgtgttaaagTTCATTGGAACAGAAAGAAATGGATTTATCTGCTCTTCGCGTTGAAGA
1561  AGTACAAAATGTCATTAATGCTATGCAGAAAATCTTAGAGTGTCCCATCTGgtaagtcag
1621  cacaagagtgtattaatttgggattcctatgattatctcctatgcaaatgaacagaattg
1681  accttacatactagggaagaaaagacatgtctagtaagattaggctattgtaattgctga
1741  ttttcttaactgaagaactttaaaaatatagaaaatgattccttgttctccatccactct
1801  gcctctcccactcctctccttttcaacacaatcctgtggtccgggaaagacagggctctg
1861  tcttgattggttctgcactgggcaggatctgttagatactgcatttgctttctccagctc
1921  taaavvvvvvvvvvvvvvaaatgctgatgatagtatagagtattgaagggatcaatataat
1981  tctgttttgatatctgaaagctcactgaaggtaaggatcgtattctctgctgtattctca
2041  gttcctgacacagcagacatttaataaatattgaacgaacttgaggccttatgttgactc
2101  agtcataacagctcaaagttgaacttattcactaagaatagctttattttaaataaatt
2161  attgagcctcatttattttctttttctccccccctaccctgctagTCTGGAGTTGATCA
2221  AGGAACCTGTCTCCACAAAGTGTGACCACATATTTTGCAAgtaagtttgaatgtgttatg
2281  tggctccattattagcttttgttttgtccttcataacccaggaaacacctaactttata
2341  gaagctttactttcttcaattaagtgagaacgaaaatccaactccatttcattcttctc
2401  agagagtatatagttatcaaaagttggttgtaatcatagttcctggtaaagttttgacat
2461  atattatctttttttttttgagacaagtctcgctctgtcgcccaggctggagtgcagt
2521  ggcatgaggcttgctcactgcacctccgcccccgagttcagcgactctvvvvvvvvvvvv
2581  vtgagatctagaccacatggtcaaagagatagaatgtgagcaataaatgaaccttaaatt
2641  tttcaacagctacttttttttttttttttgagacagGGKCTTACTCTGTTGTCCCAGCT
2701  GGAGTACAGWGTGCGATCATGAGGCTTACTGTTGCTTGACTCCTAGGCTCAAGCGATCCT
2761  ATCACCTCAGTCTCCAAGTAGCTGGACTgtaagtgcacaccaccatatccagctaaattt
2821  tgtgttttctgtagagacggggtttcgccatgtttcccaggctggtcttgaactttgggc
2881  ttaacccgtctgcccacctaggcatcccaaagtgctaggattacaggtgtgagtcatcat
2941  gcctggccagtattttagttagctctgtcttttcaagtcatatacaagttcatttctttt
3001  taagtttagttaacaaccttatatcatgtattcttttctagcataaagaaagattcgagg
```

FIG. 10A

```
3061  ccvvvvvvvvvvvvvtgtgatcataacagtaagccatatgcatgtaagttcagttttcat
3121  agatcattgcttatgtagttagGttttttgcttatgcagcatccaaaaacaattaggaaa
3181  ctattgcttgtaattcacctgccattactttttaaatggctcttaagggcagttgtgaga
3241  ttatcttttcatggctatttgcctttgagtattctttctacaaaaggaagtaaattaaa
3301  ttgttctttctttctttataatttatagATTTTGCATGCTGAAACTTCTCAACCAGAAGA
3361  AAGGGCCTTCACAGTGTCCTTTATGTAAGAATGATATAACCAAAAGgtatataatttggt
3421  aatgatgctaggttggaagcaaccacagtaggaaaaagtagaaatttatttaataacatag
3481  cgttcctataaaaccattcatcagaaaaatttataaaagagttttagcacacagtaaat
3541  tatttccaaagttatttcctgaaagttttatgggcatctgccttatacaggtattgvvv
3601  vvvvvvvvvvggtaggcttaaatgaatgacaaaagttactaaatcactgccatcacacg
3661  gtttatacagatgtcaatgatgtattgattatagaggttttctactgttgctgcatctta
3721  ttttatttgtttacatgtctttcttatttagtgtccttaaaaggttgataatcactt
3781  gctgagtgtgtttctcaaacaatttaatttcagGAGCCTACAAGAAAGTACGAGATTTAG
3841  TCAACTTGTTGAAGAGCTATTGAAAATCATTTGTGCTTTTCAGCTTGACACAGGTTTGGA
3901  GTgtaagtgttgaatatcccaagaatgacactcaagtgctgtccatgaaaactcaggaag
3961  tttgcacaattactttctatgacgtggtgataagacctttagtctaggttaatttagt
4021  tctgtatctgtaatctatttaaaaaattactcccactggtctcacaccttatttvvvvv
4081  vvvvvvvvaaaaaatcacaggtaaccttaatgcattgtcttaacacaacaaagagcatac
4141  ataggtttctcttggtttctttgattataattcatacattttctctaactgcaaacat
4201  aatgttttcccttgtattttacagATGCAAACAGCTATAATTTTGCAAAAAAGGAAAATA
4261  ACTCTCCTGAACATCTAAAAGATGAAGTTTCTATCATCCAAAGTATGGGCTACAGAAACC
4321  GTGCCAAAAGACTTCTACAGAGTGAACCCGAAAATCCTTCCTTGgtaaaaccatttgttt
4381  tcttcttcttcttcttcttcttttcttttttttttcttttttttttttgagatggagtctt
4441  gctctgtggcccaggctagaagcagtcctcctgccttagccnccttagtagctgggatta
4501  caggcacgcgcaccatgccaggctaattttgtatttagtagagacggggtttcatca
4561  tgttggccaggctggtctcgaactcctaacctcaggtgatcvvvvvvvvvvvvvatgatg
4621  gagatcttaaaaagtaatcattctggggctgggcgtagtagcttgcacctgtaatcccag
4681  cacttcgggaggctgaggcaggcagataatttgaggtcaggagtttgagaccagcctggc
4741  caacatggtgaaacccatctctactaaaaatacaaaaattagctgggtgtggtggcacgt
4801  acctgtaatcccagctactcgggaggcggaggcacaagaattgcttgaacctaggacgcg
4861  gaggttgcagcgagccaagatcgcgccactgcactccagcctgggccgtagagtgagact
4921  ctgtctcaaaaaagaaaaaaaagtaattgttctagctgggcgcagtggctcttgcctgta
4981  atcccagcactttgggaggccaaggcgggtggatctcgagtcctagagttcaagaccagc
5041  ctaggcaatgtggtgaaaccccatcgctacaaaaaatacaaaaattagccaggcatggtg
5101  gcgtgcgcatgtagtcccagctccttgggaggctgaggtgggaggatcacttgaacccag
5161  gagacagaggttgcagtgaaccgagatcacgccaccacgctccagcctgggcaacagaac
5221  aagactctgtctaaaaaaatacaaataaataaaagtagttctcacagtaccagcattca
5281  ttttcaaaagatatagagctaaaaggaaggaaaaaaaagtaatgttgggctttaaa
5341  tactcgttcctatactaaatgttcttaggagtgctggggttttattgtcatcatttatcc
5401  tttttaaaaatgttattggccaggcacggtggctcatggctgtaatcccagcactttggg
5461  aggccgaggcaggcagatcacctgaggtcaggagtgtgagaccagcctggccaacatggc
5521  gaaacctgtctctactaaaaatacaaaaattaactaggcgtggtggtgtacgcctgtagt
5581  cccagctactcgggaggctgaggcaggagaatcaactgaaccagggaggtggaggttgca
5641  gtgtgccgagatcacgccactgcactctagcctggcaacagagcaagattctgtctcaaa
5701  aaaaaaaacatatatacacatatatcccaaagtgctgggattacatatatatatatata
5761  tatatattatatatatatatatatatatgtgatatatatgtgatatatatataacata
5821  tatatatgtaatatatatgtgatatatatataatatatatgtaatatatatgtgatat
5881  atatatacacacacacacatatatgtatgtgtgtacacacacacacaaat
5941  tagccaggcatagttgcacacgcttggtagacccagctactcaggaggctgagggaggag
6001  aatctcttgaacttaggaggcggaggttgcagtgagctgagattgcgccactgcactcca
6061  gcctgggtgacagagcaggactctgtacaccccccaaaacaaaaaaaaaagttatcagat
```

FIG. 10B

```
6121  gtgattggaatgtatatcaagtatcagcttcaaaatatgctatattaatacttcaaaaat
6181  tacacaaataatacataatcaggtttgaaaaatttaagacaacmsaaraaaaaawycmaa
6241  tcacamatatcccacacatttttattattmctmctmcwattattttgwagagmctgggtct
6300  cacycykttgctwatgctggtctttgaacyccykgccycaarcartcctsctccabcctc
6361  ccaargtgctggggatwataggcatgarctaaccgcacccagccccagacattttagtgt
6421  gtaaattcctgggcattttttcaaggcatcatacatgttagctgactgatgatggtcaat
6481  ttattttgtccatggtgtcaagtttctcttcaggaggaaaagcacagaactggccaagaa
6541  ttgcttgactgttctttaccatactgtttagCAGGAAACCAGTCTCAGTGTCCAACTCTC
6601  TAACCTTGGAACTGTGAGAACTCTGAGGACAAAGCAGCGGATACAACCTCAAAAGACGTC
6661  TGTCTACATTGAATTGGtaagggtctcaggttttttaagtatttaataataattgctgg
6721  attccttatcttatagttttgccaaaaatcttggtcataatttgtatttgtggtaggcag
6781  ctttgggaagtgaattttatgagccctatggtgagttataaaaatgtaaaagacgcagt
6841  tcccaccttgaagaatcttactttaaaaagggagcaaaagaggccaggcatggtggctca
6901  cacctgtaatcccagcactttgggaggccaaagtgggtggatcacctgaggtcgggagtt
6961  cgagaccagcctagccaacatggagaaactctgtctgtaccaaaaaataaaaaattagcc
7021  aggtgtggtggcacataactgtaatcccagctactcgggaggctgaggcaggagaatcac
7081  ttgaacccgggaggtggaggttgcggtgaaccgagatcgcaccattgcactccagcctgg
7141  gcaaaaatagcgaaactccatctaaaaaaaaaaagagagcaaaagaaagamtmtctggt
7201  tttaamtmtgtgtaaatatgtttttggaaagatggagagtagcaataagaaaaaacatga
7261  tggattgctacagtatttagttccaagataaattgtactagatgaggaagcctttttaaga
7321  agagctgaattgccaggcgcagtggctcacgcctgtaatcccagcactttgggaggccga
7381  ggtgggcggatcacctgaggtcgggagttcaagaccagcctgaccaacatggagaaaccc
7441  catctctactaaaaaaaaaaaaaaaaaattagccggggtggtggcttatgcctgtaatc
7501  ccagctactcaggaggctgaggcaggagaatcgcttgaacccaggaagcagaggttgcag
7561  tgagccaagatcgcaccattgcactccagcctaggcaacaagagtgaaactccatctcaa
7621  aaaaaaaaaaagagctgaatcttggctgggcaggatggctcgtgcctgtaatcctaac
7681  gctttggaagaccgaggcagaaggattggttgagtccacgagtttaagaccagcctggcc
7741  aacatagggaaccctgtctctatttttaaaataataatacatttttggccggtgcggtg
7801  gctcatgcctgtaatcccaatactttgggaggctgaggcaggtagatcacctgaggtcag
7861  agttcgagaccagcctggataacctggtgaaacccctctttactaaaaatacaaaaaaa
7921  aaaaaaattagctgggtgtggtagcacatgcttgtaatcccagctactgggaggctgag
7981  gcaggagaatcgcttgaaccagggaggcggaggttacaatgagccaacactacaccactg
8041  cactccagcctgggcaatagagtgagactgcatctcaaaaaaataataatttttaaaaat
8101  aataaattttttaagcttataaaagaaaagtgaggccagcatagtagctcacatctg
8161  taatctcagcagtggcagaggattgcttgaagccaggagtttgagaccagcctgggcaac
8221  atagcaagacctcatctctacaaaaaaatttctttttaaattagctgggtgtggtggtg
8281  tgcatctgtagtcccagctactcaggaggcagaggtgagtggatacattgaacccaggag
8341  tttgaggctgtagtgagctatgatcatgccactgcactccaacctgggtgacagagcaag
8401  acctccaaaaaaaaaaaaaaagagctgctgagctcagaattcaaactgggctctcaaat
8461  tggatttttcttttagaatatatttataattaaaaggatagccatcttttgagctcccag
8521  gcaccaccatctatttatcataacacttactgttttccccccttatgatcataaattcct
8581  agacaacaggcattgtaaaaatagttatagtagttgatatttaggagcacttaactatat
8641  tccaggcactattgtgcttttcttgtataactcattagatgcttgtcagacctctgagat
8701  tgttcctattatacttattttacagatgagaaaattaaggcacagagaagttatgaaatt
8761  tttccaaggtattaaacctagtaagtggctgagccatgattcaaacctaggaagttagat
8821  gtcagagcctgtgcttttttttgttttgttttgttttcagtagaaacgggggtctca
8881  ctttgttggccaggctggtcttgaactcctaacctcaaataatccacccatctcggcctc
8941  ctcaagtgctgggattacaggtgagagccactgtgcctggcgaagcccatgcctttaacc
9001  acttctctgtattacatactagcttaactagcattgtacctgccacagtagatgctcagt
9061  aaatatttctagttgaatatctgttttcaacaagtacatttttttaacccttttaatta
9121  agaaaactttattgatttattttttgggggaaattttttagGATCTGATTCTTCTGAA
```

FIG. 10C

```
 9181  GATACCGTTAATAAGGAACTTATTGCAGgtgagtcaaagagaacctttgtctatgaagc
 9241  tggtattttcctatttagttaatattaaggattgatgtttctctcttttaaaaatattt
 9301  taactttattttaggttcagggatgtatgtgcagtttgttatataggtaaacacacgac
 9361  ttgggatttggtgtatagattttttcatcatccgggtactaagcatacccacagtttt
 9421  ttgtttgctttctttctgaatttctccctcttcccaccttcctccctcaagtaggctggt
 9481  gtttctccagactagaatcatggtattggaagaaaccttagagatcatctagtttagttc
 9541  tctcattttatagtggaggaaatacccttttgtttgttggatttagttattagcactgt
 9601  ccaaaggaatttaggataacagtagaactctgcacatgcttgcttctagcagattgttct
 9661  ctaagttcctcatatacagtaatattgacacagcagtaattgtgactgatgaaaatgttc
 9721  aaggacttcattttcaactctttctttcctctgttccttatttccacatatctctcaagc
 9781  tttgtctgtatgttatataataaactacaagcaaccccaactatgttacctaccttcctt
 9841  aggaattattgcttgacccaggttttttttttttttttttttggagacgggtcttgccct
 9901  gttgccaggatggagtgtagtggcgccatctcggctcactgcaatctccaactcctggt
 9961  tcaagcgattctcctgtctcaatctcacgagtagctgggactacaggtatacaccaccac
10021  gcccggttaattgaccattccatttctttctttctctcttttttttttttttttttgaga
10081  cagagtcttgctctgttgcccaggctggagtacagaggtgtgatctcacctctccgcaac
10141  gtctgcctcccaggttgaagccatactctgcctcagcctctctagtagctgggactaca
10201  ggcgcgcgccaccacacccggctaattttgtatttttagtagagatggggtttcaccat
10261  gttggccaggctggtcttgaactcatgacctcaagtggtccacccgcctcagcctcccaa
10321  agtgctggaattacaggcttgagccaccgtgcccagcaaccatttcatttcaactagaag
10381  tttctaaaggagagagcagctttcactaactaaataagattggtcagctttctgtaatcg
10441  aaagagctaaaatgtttgatcttggtcatttgacagttctgcatacatgtaactagtgtt
10501  tcttattaggactctgtcttttccctatagTGTGGGAGATCAAGAATTGTTACAAATCAC
10561  CCCTCAAGGAACCAGGGATGAAATCAGTTTGGATTCTGCAAAAAAGGgtaatggcaaagt
10621  ttgccaacttaacaggcactgaaaagagagtgggtagatacagtactgtaattagattat
10681  tctgaagaccatttgggaccttacaacccacaaaatctcttggcagagttagagtatca
10741  ttctctgtcaaatgtcgtggtatggtctgatagatttaaatggtactagactaatgtacc
10801  tataataagaccttcttgtaactgattgttgccctttcgcttttttttttgtttgtttgt
10861  ttgtttttttttgagatggggtctcactctgttgcccaggctggagtgcagtgatgcaat
10921  cttggctcactgcaacctccacctccaaaggctcaagctatcctcccacttcagcctcct
10981  gagtagctgggactacaggcgcatgccaccacacccggttaattttttgtggttttatag
11041  agatggggtttcaccatgttaccgagctggtctcaaactcctggactcaagcagtctgc
11101  ccactcagcctcccaaagtgctgcagttacaggcttgagccactgtgcctggcctgccc
11161  tttacttttaattggtgtatttgtgtttcatcttttacctactggttttttaaatataggg
11221  agtggtaagtctgtagatagaacagagtattaagtagacttaatggccagtaatctttag
11281  agtacatcagaaccagttttctgatggccaatctgcttttaattcactcttagacgttag
11341  agaaataggtgtggtttctgcatagggaaaattctgaaattaavvvvvvvvvvvvvvgatc
11401  ctaagtggaaataatctaggtaaataggaattaaatgaaagagtatgagctacatcttca
11461  gtatacttggtagtttatgaggttagtttctctaatatagccagttggttgatttccacc
11521  tccaaggtgtatgaagtatgtattttttaatgacaattcagtttttgagtaccttgtta
11581  tttttgtatattttcagCTGCTTGTGAATTTTCTGAGACGGATGTAACAAATACTGAACA
11641  TCATCAACCCAGTAATAATGATTTGAACACCACTGAGAAGCGTGCAGCTGAGAGGCATCC
11701  AGAAAAGTATCAGGGTAGTTCTGTTTCAAACTTGCATGTGGAGCCATGTGGCACAAATAC
11761  TCATGCCAGCTCATTACAGCATGAGAACAGCAGTTTATTACTCACTAAAGACAGAATGAA
11821  TGTAGAAAAGGCTGAATTCTGTAATAAAAGCAAACAGCCTGGCTTAGCAAGGAGCCAACA
11881  TAACAGATGGGCTGGAAGTAAGGAAACATGTAATGATAGGCGGACTCCCAGCACAGAAAA
11941  AAAGGTAGATCTGAATGCTGATCCCCTGTGTGAGAGAAAAGAATGGAATAAGCAGAAACT
12001  GCCATGCTCAGAGAATCCTAGAGATACTGAAGATGTTCCTTGGATAACACTAAATAGCAG
12061  CATTCAGAAAGTTAATGAGTGGTTTTCCAGAAGTGATGAACTGTTAGGTTCTGATGACTC
12121  ACATGATGGGGAGTCTGAATCAAATGCCAAGTAGCTGATGTATTGGACGTTCTAAATGA
12181  GGTAGATGAATATTCTGGTTCTTCAGAGAAAATAGACTTACTGGCCAGTGATCCTCATGA
```

FIG. 10D

```
12241  GGCTTTAATATGTAAAAGTGAAAGAGTTCACTCCAAATCAGTAGAGAGTAATATTGAAGG
12301  CCAATATTTGGGAAAACCTATCGGAAGAAGGCAAGCCTCCCCAACTTAAGCCATGTAAC
12361  TGAAAATCTAATTATAGGAGCATTTGTTACTGAGCCACAGATAATACAAGAGCGTCCCT
12421  CACAAATAAATTAAAGCGTAAAAGGAGACCTACATCAGGCCTTCATCCTGAGGATTTTAT
12481  CAAGAAAGCAGATTTGGCAGTTCAAAAGACTCCTGAAATGATAAATCAGGGAACTAACCA
12541  AACGGAGCAGAATGGTCAAGTGATGAATATTACTAATAGTGGTCATGAGAATAAAACAAA
12601  AGGTGATTCTATTCAGAATGAGAAAAATCCTAACCCAATAGAATCACTCGAAAAGAATC
12661  TGCTTTCAAAACGAAAGCTGAACCTATAAGCAGCAGTATAAGCAATATGGAACTCGAATT
12721  AAATATCCACAATTCAAAAGCACCTAAAAAGAATAGGCTGAGGAGGAAGTCTTCTACCAG
12781  GCATATTCATGCGCTTGAACTAGTAGTCAGTAGAAATCTAAGCCCACCTAATTGTACTGA
12841  ATTGCAAATTGATAGTTGTTCTAGCAGTGAAGAGATAAAGAAAAAAAGTACAACCAAAT
12901  GCCAGTCAGGCACAGCAGAAACCTACAACTCATGGAAGGTAAAGAACCTGCAACTGGAGC
12961  CAAGAAGAGTAACAAGCCAAATGAACAGACAAGTAAAAGACATGACAGCGATACTTTCCC
13021  AGAGCTGAAGTTAACAAATGCACCTGGTTCTTTTACTAAGTGTTCAAATACCAGTGAACT
13081  TAAAGAATTTGTCAATCCTAGCCTTCCAAGAGAAGAAAAAGAAGAGAAACTAGAAACAGT
13141  TAAAGTGTCTAATAATGCTGAAGACCCCAAAGATCTCATGTTAAGTGGAGAAAGGGTTTT
13201  GCAAACTGAAAGATCTGTAGAGAGTAGCAGTATTTCATTGGTACCTGGTACTGATTATGG
13261  CACTCAGGAAAGTATCTCGTTACTGGAAGTTAGCACTCTAGGGAAGGCAAAAACAGAACC
13321  AAATAAATGTGTGAGTCAGTGTGCAGCATTTGAAAACCCCAAGGGACTAATTCATGGTTG
13381  TTCCAAAGATAATAGAAATGACACAGAAGGCTTTAAGTATCCATTGGGACATGAAGTTAA
13441  CCACAGTCGGGAAACAAGCATAGAAATGGAAGAAAGTGAACTTGATGCTCAGTATTTGCA
13501  GAATACATTCAAGGTTTCAAAGCGCCAGTCATTTGCTCCGTTTTCAAATCCAGGAAATGC
13561  AGAAGAGGAATGTGCAACATTCTCTGCCCACTCTGGGTCCTTAAAGAAACAAAGTCCAAA
13621  AGTCACTTTTGAATGTGAACAAAAGGAAGAAAATCAAGGAAAGAATGAGTCTAATATCAA
13681  GCCTGTACAGACAGTTAATATCACTGCAGGCTTTCCTGTGGTTGGTCAGAAAGATAAGCC
13741  AGTTGATAATGCCAAATGTAGTATCAAAGGAGGCTCTAGGTTTTGTCTATCATCTCAGTT
13801  CAGAGGCAACGAAACTGGACTCATTACTCCAAATAAACATGGACTTTTACAAACCCATA
13861  TCGTATACCACCACTTTTTCCCATCAAGTCATTTGTTAAAACTAAATGTAAGAAAAATCT
13921  GCTAGAGGAAAACTTTGAGGAACATTCAATGTCACCTGAAAGAGAAATGGGAAATGAGAA
13981  CATTCCAAGTACAGTGAGCACAATTAGCCGTAATAACATTAGAGAAAATGTTTTTAAAGA
14041  AGCCAGCTCAAGCAATATTAATGAAGTAGGTTCCAGTACTAATGAAGTGGGCTCCAGTAT
14101  TAATGAAATAGGTTCCAGTGATGAAAACATTCAAGCAGAACTAGGTAGAAACAGAGGGCC
14161  AAAATTGAATGCTATGCTTAGATTAGGGGTTTTGCAACCTGAGGTCTATAAACAAAGTCT
14221  TCCTGGAAGTAATTGTAAGCATCCTGAAATAAAAAGCAAGAATATGAAGAAGTAGTTCA
14281  GACTGTTAATACAGATTTCTCTCCATATCTGATTTCAGATAACTTAGAACAGCCTATGGG
14341  AAGTAGTCATGCATCTCAGGTTTGTTCTGAGACACCTGATGACCTGTTAGATGATGGTGA
14401  AATAAAGGAAGATACTAGTTTTGCTGAAAATGACATTAAGGAAAGTTCTGCTGTTTTTAG
14461  CAAAAGCGTCCAGAAAGGAGAGCTTAGCAGGAGTCCTAGCCCTTTCACCCATACACATTT
14521  GGCTCAGGGTTACCGAAGAGGGGCCAAGAAATTAGAGTCCTCAGAAGAGAACTTATCTAG
14581  TGAGGATGAAGAGCTTCCCTGCTTCCAACACTTGTTATTTGGTAAAGTAAACAATATACC
14641  TTCTCAGTCTACTAGGCATAGCACCGTTGCTACCGAGTGTCTGTCTAAGAACACAGAGGA
14701  GAATTTATTATCATTGAAGAATAGCTTAAATGACTGCAGTAACCAGGTAATATTGGCAAA
14761  GGCATCTCAGGAACATCACCTTAGTGAGGAAACAAAATGTTCTGCTAGCTTGTTTTCTTC
14821  ACAGTGCAGTGAATTGGAAGACTTGACTGCAAATACAAACACCCAGGATCCTTTCTTGAT
14881  TGGTTCTTCCAAACAAATGAGGCATCAGTCTGAAAGCCAGGGAGTTGGTCTGAGTGACAA
14941  GGAATTGGTTTCAGATGATGAAGAAGAGGAACGGGCTTGGAAGAAAATAATCAAGAAGA
15001  GCAAAGCATGGATTCAAACTTAGgtattggaaccaggttttgtgtttgccccagtctat
15061  ttatagaagtgagctaaatgtttatgcttttggggagcacattttacaaatttccaagta
15121  tagttaaaggaactgcttcttaaacttgaaacatgttcctcctaaggtgcttttcataga
15181  aaaaagtccttcacacagctaggacgtcatctttgactgaatgagctttaacatcctaat
15241  tactggtggacttacttctggtttcattttataaagcaaatcccggtgtcccaaagcaag
```

FIG. 10E

```
15301  gaatttaatcatttgtgtgacatgaaagtaaatccagtcctgccaatgagaagaaaaag
15361  acacagcaagttgcagcgtttatagtctgcttttacatctgaacctctgtttttgttatt
15421  taagGTGAAGCAGCATCTGGGTGTGAGAGTGAAACAAGCGTCTCTGAAGACTGCTCAGGG
15481  CTATCCTCTCAGAGTGACATTTTAACCACTCaggtaaaaagcgtgtgtgtgtgcacat
15541  gcgtgtgtgtggtgtcctttgcattcagtagtatgtatcccacattcttaggtttgctga
15601  catcatctctttgaattaatggcacaattgtttgtggttcattgtcvvvvvvvvvvvvn
15661  gngaatgtaatcctaatatttcncnccnacttaaaagaataccactccaanggcatcnca
15721  atacatcaatcaattggggaattgggattttccctcnctaacatcantggaataatttca
15781  tggcattaattgcatgaatgtggttagattaaaaggtgttcatgctagaacttgtagttc
15841  catactaggtgatttcaattcctgtgctaaaattaatttgtatgatatattntcatttaa
15901  tggaaagcttctcaaagtatttcattttcttggtaccatttatcgtttttgaAGCAGAGG
15961  GATACCATGCAACATAACCTGATAAAGCTCCAGCAGGAAATGGCTGAACTAGAAGCTGTG
16021  TTAGAACAGCATGGGAGCCAGCCTTCTAACAGCTACCCTTCCATCATAAGTGACTCTTCT
16081  GCCCTTGAGGACCTGCGAAATCCAGAACAAAGCACATCAGAAAAAGgtgtgtattgttgg
16141  ccaaacactgatatcttaagcaaaattctttccttcccctttatctccttctgaagagta
16201  aggacctagctccaacattttatgatccttgctcagcacatgggtaattatggagccttg
16261  gttcttgtccctgctcacaactaatataccagtcagagggacccaaggcagtcattcatg
16321  ttgtcatctgagatacctacaacaagtagatgctatggggagcccatggvvvvvvvvvvv
16381  vvccattggtgctagcatctgtctgttgcattgcttgtgtttataaaattctgcctgata
16441  tacttgttaaaaaccaatttgtgtatcatagattgatgcttttgaaaaaaatcagtattc
16501  taacctgaattatcactatcagaacaaagcagtaaagtagatttgttttctcattccatt
16561  taaagCAGTATTAACTTCACAGAAAAGTAGTGAATACCCTATAAGCCAGAATCCAGAAGG
16621  CCTTTCTGCTGACAAGTTTGAGGTGTCTGCAGATAGTTCTACCAGTAAAAATAAAGAACC
16681  AGGAGTGGAAAGgtaagaaacatcaatgtaaagatgctgtggtatctgacatctttattt
16741  atattgaactctgattgttaatttttttccaccatactttctccagtttttttgcatacag
16801  gcatttatacacttttattgctctaggatacttcttttgtttaatcctatataggvvvvv
16861  vvvvvvvvggataagntcaagagatattttgataggtgatgcagtgataattgngaaaa
16921  tttnctgcctgcttttaatcttccccgttcttcttcctncctccctcccttcctncct
16981  cccgtccttncctttccttttcctcccttccnccttctttccntctntctttccttttctt
17041  tcctgtctacctttctttccttcctccccttccttttcttttctttctttcctttccttt
17101  ctttcctttctttccttttccttttctttcttgacagagtcttgctctgtcactcaggctgg
17161  agtgcagtggcgtgatctcgnctcactgcaacctctgtctcccaggttcaagcaatttc
17221  ctgcctcagcctcccgagtagctgagattacaggcgccagccaccacacccagctactga
17281  cctgcttttvvvvvvvvvvvvvaaacagctgggagatatggtgcctcagaccaagcccat
17341  gttatatgtcaaccctgacatattggcaggcaacatgaatccagacttctaggctgtcat
17401  gcgggctcttttttgccagtcatttctgatctctctgacatgagctgtttcatttatgct
17461  ttggctgcccagcaagtatgatttgtcctttcacaattggtggcgatggttttctccttc
17521  catttatctttctagGTCATCCCCTTCTAAATGCCCATCATTAGATGATAGGTGGTACAT
17581  GCACAGTTGCTCTGGGAGTCTTCAGAATAGAAACTACCCATCTCAAGAGGAGCTCATTAA
17641  GGTTGTTGATGTGGAGGAGCAACAGCTGGAAGAGTCTGGGCCACACGATTTGACGGAAAC
17701  ATCTTACTTGCCAAGGCAAGATCTAGgtaatatttcatctgctgtattggaacaaacact
17761  ytgatttactctgaatcctacataaagatattctggttaaccaacttttagatgtacta
17821  gtctatcatggacacttttgttatacttaattaagcccactttagaaaaatagctcaagt
17881  gttaatcaaggtttacttgaaaattattgaaactgttaatccatctatattttaattaat
17941  ggtttaactaatgattttgaggatgwgggagtcktggtgtactctamatgtattatttca
18001  ggccaggcatagtggctcacgcctggtaatcccagtayycmrgagcccgaggcaggtgga
18061  gccagctgaggtcaggagttcaagacctgtcttggccaacatgggngaaacctgtcttc
18121  ttcttaaaaaanacaaaaaaattaactgggttgtgcttaggtgnatgccccgnatccta
18181  gttnttcttgngggttgagggaggagatcacnttggaccccggagggngggtgggggng
18241  agcaggncaaaacacngacccagctggggtggaagggaagcccactcnaaaaaannttnv
18301  vvvvvvvvvvvvvttttttaggaaacaagctactttggatttccaccaacacctgtattcat
```

FIG. 10F

```
18361  gtacccattttctcttaacctaactttattggtcttttaattcttaacagagaccaga
18421  actttgtaattcaacattcatcgttgtgtaaattaaacttctcccattcctttcagAGGG
18481  AACCCCTTACCTGGAATCTGGAATCAGCCTCTTCTCTGATGACCCTGAATCTGATCCTTC
18541  TGAAGACAGAGCCCCAGAGTCAGCTCGTGTTGGCAACATACCATCTTCAACCTCTGCATT
18601  GAAAGTTCCCCAATTGAAAGTTGCAGAATCTGCCCAGAGTCCAGCTGCTGCTCATACTAC
18661  TGATACTGCTGGGTATAATGCAATGGAAGAAAGTGTGAGCAGGGAGAAGCCAGAATTGAC
18721  AGCTTCAACAGAAAGGGTCAACAAAAGAATGTCCATGGTGGTGTCTGGCCTGACCCCAGA
18781  AGAATTTgtgagtgtatccatatgtatctccctaatgactaagacttaacaacattctgg
18841  aaagagttttatgtaggtattgtcaattaataacctagaggaagaaatctagaaaacaat
18901  cacagttctgtgtaatttaatttcgattactaatttctgaaaatttagaayvvvvvvvvv
18961  vvvvnccnnccccccnaatctgaaatgggggtaaccccccccccaaccganacntgggtng
19021  cntagagantttaatggccnttctgaggnacanaagcttaagccaggngacgtggancn
19081  atgngttgtttnttgtttggttacctccagcctgggtgacagagcaagactctgtctaaa
19141  aaaaaaaaaaaaaaaatcgactttaaatagttccaggacacgtgtagaacgtgcaggat
19201  tgctacgtaggtaaacatatgccatggtgggataactagtattctgagctgtgtgctaga
19261  ggtaactcatgataatggaatatttgatttaatttcagATGCTCGTGTACAAGTTTGCCA
19321  GAAAACACCACATCACTTTAACTAATCTAATTACTGAAGAGACTACTCATGTTGTTATGA
19381  AAACAGgtataccaagaacctttacagaatacctttgcatctgctgcataaaaccacatga
19441  ggcgaggcacggtggcgcatgcctgtaatcgcagcactttgggaggccgaggcgggcaga
19501  tcacgagattaggagatcgagaccatcctggccagcatggtgaaacccgtctctactan
19561  naaatggnaaaattanctgggtgtggtcgcgtgcnctgtagtcccagctactcgtgagg
19621  ctgaggcaggagaatcacttgaaccggggaaatggaggtttcagtgagcagagatcatnc
19681  ccctncattccagcctggcgacagagcaaggctccgtcnccnaaaaaataaaaaaaaacg
19741  tgaacaaataagaatatttgttgagcatagcatggatgatagtcttctaatagtcaatca
19801  attactttatgaaagacaaataatagttttgctgcttccttacctccttttgttttgggt
19861  taagatttggagtgtgggccaggcacvvvvvvvvvvvvvgatctatagctagccttggcg
19921  tctagaagatgggtgttgagaagagggagtggaaagatatttcctctggtcttaacttca
19981  tatcagcctccctagacttccaaatatccatacctgctggttataattagtggtgttt
20041  cagcctctgattctgtcaccaggggtttagaatcataaatccagattgatcttgggagt
20101  gtaaaaactgaggctctttagcttcttaggacagcacttcctgattttgttttcaactt
20161  ctaatcctttgagtgttttcattctgcagATGCTGAGTTTGTGTGTGAACGGACACTGA
20221  AATATTTTCTAGGAATTGCGGGAGGAAAATGGGTAGTTAGCTATTTCTgtaagtataata
20281  ctatttctccctcctcccctttaacacctcagaattgcattttacacctaacatttaac
20341  acctaaggttttgctgatgctgagtctgagttaccaaaaggtctttaaattgtaatact
20401  aaactactttatctttaatatcactttgttcaagataagctggtgatgctgggaaaatg
20461  ggtctcttttataactaataggacctaatctgctcctagcaatgttagcatatgagctag
20521  ggatttatttaatagtcggcaggaatccatgtgcarcagncaaacttataatgtttaaat
20581  taaacatcaactctgtctccagaaggaaactgctgctacaagccttattaaagggctgtg
20641  gctttagagggaaggacctctcctctgtcattcttcctgtgctcttttgtgaatcgctga
20701  cctctctatctccgtgaaaagagcacgttcttctgctgtatgtaacctgtcttttctatg
20761  atctctvvvvvvvvvvvvnaaaaacggggnngggantgggccttaaanccaaagggcna
20821  actccccaaccattnaaaaantgacngggattattaaaancggcgggaaacatttcacn
20881  gcccaactaatattgttaaattaaaaccaccaccnctgcnccaaggagggaaactgctgc
20941  tacaagccttattaaagggctgtggctttagagggaaggacctctcctctgtcattcttc
21001  ctgtgctcttttgtgaatcgctgacctctctatgtccgtgaaaagagcacgttcttcgtc
21061  tgtatgtaacctgtcttttctatgatctctttagGGGTGACCCAGTCTATTAAAGAAAGA
21121  AAATGCTGAATGAGgtaagtacttgatgttacaaactaaccagagatattcattcagtc
21181  atatagttaaaaatgtatttgcttccttccatcaatgcaccactttccttaacaatgcac
21241  aaattttccatgataatgaggatcatcaagaattatgcaggcctgcactgtggctcatac
21301  ctataatcccagcgctttgggaggctgaggcgcttggatcvvvvvvvvvvvvvaattttt
21361  tgtattttagtagagatgaggttcaccatgttggtctagatctggtgtcgaacgtcctg
```

FIG. 10G

```
21421  acctcaagtgatctgccagcctcagtctcccaaagtgctaggattacaggggtgagccac
21481  tgcgcctggcctgaatgcctaaaatatgacgtgtctgctccacttccattgaaggaagct
21541  tctctttctcttatcctgatgggttgtgtttggtttctttcagCATGATTTTGAAGTCAG
21601  AGGAGATGTGGTCAATGGAAGAAACCACCAAGGTCCAAAGCGAGCAAGAGAATCCCAGGA
21661  CAGAAAGgtaaagctccctccctcaagttgacaaaaatctcaccccaccactctgtattc
21721  cactcccctttgcagagatgggccgcttcattttgtaagacttattacatacatacacag
21781  tgctagatactttcacacaggttctttttcactcttccatcccaaccacataaataagt
21841  attgtctctactttatgaatgataaaactaagagatttagagaggctgtgtaatttggat
21901  tcccgtctcgggttcagatcvvvvvvvvvvvvvvttggcctgattggtgacaaaagtgaga
21961  tgctcagtccttgaatgacaaagaatgcctgtagagttgcaggtccaactacatatgcac
22021  ttcaagaagatcttctgaaatctagtagtgttctggacattggactgcttgtccctggga
22081  agtagcagcagaaatgatcggtggtgaacagaagaaaagaaaagctcttcctttttgaa
22141  agtctgtttttgaataaaagccaatattctttttataactagattttccttctctccatt
22201  cccctgtcctctctcttcctctcttcttccagATCTTCAGGGGGCTAGAAATCTGTTGC
22261  TATGGGCCCTTCACCAACATGCCCACAGgtaagagcctgggagaaccccagagttccagc
22321  accagcctttgtcttacatagtggagtattataagcaaggtcccacgatgggggttcctc
22381  agattgctgaaatgttctagaggctattctatttctctaccactctccaaacaaaacagc
22441  acctaaatgttatcctatggcaaaaaaaaactataccttgtcccccttctcaagagcatg
22501  aaggtggttaatagttaggattcagtatgttatgtgttcagatggcgttgagctgctgtt
22561  agtgccvvvvvvvvvvvvvvvtttgagagactatcaaaccttataccaagtggccttatgga
22621  gactgataaccagagtacatggcatatcagtggcaaattgacttaaaatccatacccta
22681  ctattttaagaccattgtcctttggagcagagagacagactctcccattgagaggtcttg
22741  ctataagccttcatccggagagtgtagggtagagggcctgggttaagtatgcagattact
22801  gcagtgattttacatgtaaatgtccatttagATCAACTGGAATGGATGGTACAGCTGTG
22861  TGGTGCTTCTGTGGTGAAGGAGCTTTCATCATTCACCCTTGGCACAgtaagtattgggtg
22921  ccctgtcagtgtgggaggacacaatattctctcctgtgagcaagactggcacctgtcagt
22981  ccctatggatgcccctactgtagcctcagaagtcttctctgcccacatacctgtgccaaa
23041  agactccatvvvvvvvvvvvvvvvggtggtacgtgtctgtagttccagctacttgggaggct
23101  gagatggaaggattgcttgagcccaggaggcagaggtggnannttacgctgagatcacac
23161  cactgcactccagcctgggtgacagagcaagaccctgtctcaaaaacaaacaaaaaaaat
23221  gatgaagtgacagttccagtagtcctactttgacactttgaatgctctttccttcctggg
23281  gatccagGGTGTCCACCCAATTGTGGTTGTGCAGCCAGATGCCTGGACAGAGGACAATGG
23341  CTTCCATGgtaaggtgcctcgcatgtacctgtgctattagtggggtccttgtgcatgggt
23401  ttggtttatcactcattacctggtgcttgagtagcacagttcttggcacatttttaaata
23461  tttgttgaatgaatggctaaaatgtcttttgatgttttattgttatttgttttatatt
23521  gtaaaagtaatacatgaactgtttccatggggtgggagtaagatatgaatgttcatcacv
23581  vvvvvvvvvvvvcagtaatcctnagaactcatacgaccgggcccctggagtcgntgnttn
23641  gagcctagtccnggagaatgaattgacactaatctctgcttgtgttctctgtctccagCA
23701  ATTGGGCAGATGTGTGAGGCACCTGTGGTGACCCGAGAGTGGGTGTTGGACAGTGTAGCA
23761  CTCTACCAGTGCCAGGAGCTGGACACCTACCTGATACCCCAGATCCCCCACAGCCACTAC
23821  TGACTGCAGCCAGCCACAGGTACAGAGCCACAGGACCCCAAGAATGAGCTTACAAAGTGG
23881  CCTTTCCAGGCCCTGGGAGCTCCTCTCACTCTTCAGTCCTTCTACTGTCCTGGCTACTAA
23941  ATATTTTATGTACATCAGCCTGAAAAGGACTTCTGGCTATGCAAGGGTCCCTTAAAGATT
24001  TTCTGCTTGAAGTCTCCCTTGGAAAT
```

FIG. 10H

SEQUENCE LISTING ( 1 ) GENERAL INFORMATION:

( i i i ) NUMBER OF SEQUENCES: 85

( 2 ) INFORMATION FOR SEQ ID NO:1:

( i ) SEQUENCE CHARACTERISTICS:
( A ) LENGTH: 5914 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Homo sapiens ( i x ) FEATURE:
( A ) NAME/KEY: CDS
( B ) LOCATION: 120..5708

( x i ) SEQUENCE DESCRIPTION: SEQ ID NO:1:

AGCTCGCTGA GACTTCCTGG ACCCCGCACC AGGCTGTGGG GTTTCTCAGA TAACTGGGCC    60

```
CCTGCGCTCA GGAGGCCTTC ACCCTCTGCT CTGGGTAAAG TTCATTGGAA CAGAAAGAA                                      119

ATG GAT TTA TCT GCT CTT CGC GTT GAA GAA GTA CAA AAT GTC ATT AAT                                      167
Met Asp Leu Ser Ala Leu Arg Val Glu Glu Val Gln Asn Val Ile Asn
 1           5                    10                      15

GCT ATG CAG AAA ATC TTA GAG TGT CCC ATC TGT CTG GAG TTG ATC AAG                                      215
Ala Met Gln Lys Ile Leu Glu Cys Pro Ile Cys Leu Glu Leu Ile Lys
          20                  25                      30

GAA CCT GTC TCC ACA AAG TGT GAC CAC ATA TTT TGC AAA TTT TGC ATG                                      263
Glu Pro Val Ser Thr Lys Cys Asp His Ile Phe Cys Lys Phe Cys Met
              35                  40                  45

CTG AAA CTT CTC AAC CAG AAG AAA GGG CCT TCA CAG TGT CCT TTA TGT                                      311
Leu Lys Leu Leu Asn Gln Lys Lys Gly Pro Ser Gln Cys Pro Leu Cys
      50                  55                  60

AAG AAT GAT ATA ACC AAA AGG AGC CTA CAA GAA AGT ACG AGA TTT AGT                                      359
Lys Asn Asp Ile Thr Lys Arg Ser Leu Gln Glu Ser Thr Arg Phe Ser
 65                  70                  75                  80

CAA CTT GTT GAA GAG CTA TTG AAA ATC ATT TGT GCT TTT CAG CTT GAC                                      407
Gln Leu Val Glu Glu Leu Leu Lys Ile Ile Cys Ala Phe Gln Leu Asp
              85                  90                  95

ACA GGT TTG GAG TAT GCA AAC AGC TAT AAT TTT GCA AAA AAG GAA AAT                                      455
Thr Gly Leu Glu Tyr Ala Asn Ser Tyr Asn Phe Ala Lys Lys Glu Asn
                100                 105                 110

AAC TCT CCT GAA CAT CTA AAA GAT GAA GTT TCT ATC ATC CAA AGT ATG                                      503
Asn Ser Pro Glu His Leu Lys Asp Glu Val Ser Ile Ile Gln Ser Met
        115                 120                 125

GGC TAC AGA AAC CGT GCC AAA AGA CTT CTA CAG AGT GAA CCC GAA AAT                                      551
Gly Tyr Arg Asn Arg Ala Lys Arg Leu Leu Gln Ser Glu Pro Glu Asn
        130                 135                 140

CCT TCC TTG CAG GAA ACC AGT CTC AGT GTC CAA CTC TCT AAC CTT GGA                                      599
Pro Ser Leu Gln Glu Thr Ser Leu Ser Val Gln Leu Ser Asn Leu Gly
145                 150                 155                 160

ACT GTG AGA ACT CTG AGG ACA AAG CAG CGG ATA CAA CCT CAA AAG ACG                                      647
Thr Val Arg Thr Leu Arg Thr Lys Gln Arg Ile Gln Pro Gln Lys Thr
                165                 170                 175

TCT GTC TAC ATT GAA TTG GGA TCT GAT TCT TCT GAA GAT ACC GTT AAT                                      695
Ser Val Tyr Ile Glu Leu Gly Ser Asp Ser Ser Glu Asp Thr Val Asn
                180                 185                 190

AAG GCA ACT TAT TGC AGT GTG GGA GAT CAA GAA TTG TTA CAA ATC ACC                                      743
Lys Ala Thr Tyr Cys Ser Val Gly Asp Gln Glu Leu Leu Gln Ile Thr
        195                 200                 205

CCT CAA GGA ACC AGG GAT GAA ATC AGT TTG GAT TCT GCA AAA AAG GCT                                      791
Pro Gln Gly Thr Arg Asp Glu Ile Ser Leu Asp Ser Ala Lys Lys Ala
        210                 215                 220

GCT TGT GAA TTT TCT GAG ACG GAT GTA ACA AAT ACT GAA CAT CAT CAA                                      839
Ala Cys Glu Phe Ser Glu Thr Asp Val Thr Asn Thr Glu His His Gln
225                 230                 235                 240

CCC AGT AAT AAT GAT TTG AAC ACC ACT GAG AAG CGT GCA GCT GAG AGG                                      887
Pro Ser Asn Asn Asp Leu Asn Thr Thr Glu Lys Arg Ala Ala Glu Arg
                245                 250                 255

CAT CCA GAA AAG TAT CAG GGT AGT TCT GTT TCA AAC TTG CAT GTG GAG                                      935
His Pro Glu Lys Tyr Gln Gly Ser Ser Val Ser Asn Leu His Val Glu
        260                 265                 270

CCA TGT GGC ACA AAT ACT CAT GCC AGC TCA TTA CAG CAT GAG AAC AGC                                      983
Pro Cys Gly Thr Asn Thr His Ala Ser Ser Leu Gln His Glu Asn Ser
        275                 280                 285

AGT TTA TTA CTC ACT AAA GAC AGA ATG AAT GTA GAA AAG GCT GAA TTC                                     1031
Ser Leu Leu Leu Thr Lys Asp Arg Met Asn Val Glu Lys Ala Glu Phe
        290                 295                 300

TGT AAT AAA AGC AAA CAG CCT GGC TTA GCA AGG AGC CAA CAT AAC AGA                                     1079
```

|  |  |
|---|---|
| Cys Asn Lys Ser Lys Gln Pro Gly Leu Ala Arg Ser Gln His Asn Arg<br>305                    310                    315                    320 |  |
| TGG GCT GGA AGT AAG GAA ACA TGT AAT GAT AGG CGG ACT CCC AGC ACA<br>Trp Ala Gly Ser Lys Glu Thr Cys Asn Asp Arg Arg Thr Pro Ser Thr<br>                  325                    330                    335 | 1127 |
| GAA AAA AAG GTA GAT CTG AAT GCT GAT CCC CTG TGT GAG AGA AAA GAA<br>Glu Lys Lys Val Asp Leu Asn Ala Asp Pro Leu Cys Glu Arg Lys Glu<br>                    340                    345                    350 | 1175 |
| TGG AAT AAG CAG AAA CTG CCA TGC TCA GAG AAT CCT AGA GAT ACT GAA<br>Trp Asn Lys Gln Lys Leu Pro Cys Ser Glu Asn Pro Arg Asp Thr Glu<br>                355                    360                    365 | 1223 |
| GAT GTT CCT TGG ATA ACA CTA AAT AGC AGC ATT CAG AAA GTT AAT GAG<br>Asp Val Pro Trp Ile Thr Leu Asn Ser Ser Ile Gln Lys Val Asn Glu<br>            370                    375                    380 | 1271 |
| TGG TTT TCC AGA AGT GAT GAA CTG TTA GGT TCT GAT GAC TCA CAT GAT<br>Trp Phe Ser Arg Ser Asp Glu Leu Leu Gly Ser Asp Asp Ser His Asp<br>385                    390                    395                    400 | 1319 |
| GGG GAG TCT GAA TCA AAT GCC AAA GTA GCT GAT GTA TTG GAC GTT CTA<br>Gly Glu Ser Glu Ser Asn Ala Lys Val Ala Asp Val Leu Asp Val Leu<br>                            405                    410                    415 | 1367 |
| AAT GAG GTA GAT GAA TAT TCT GGT TCT TCA GAG AAA ATA GAC TTA CTG<br>Asn Glu Val Asp Glu Tyr Ser Gly Ser Ser Glu Lys Ile Asp Leu Leu<br>                    420                    425                    430 | 1415 |
| GCC AGT GAT CCT CAT GAG GCT TTA ATA TGT AAA AGT GAA AGA GTT CAC<br>Ala Ser Asp Pro His Glu Ala Leu Ile Cys Lys Ser Glu Arg Val His<br>            435                    440                    445 | 1463 |
| TCC AAA TCA GTA GAG AGT AAT ATT GAA GAC AAA ATA TTT GGG AAA ACC<br>Ser Lys Ser Val Glu Ser Asn Ile Glu Asp Lys Ile Phe Gly Lys Thr<br>            450                    455                    460 | 1511 |
| TAT CGG AAG AAG GCA AGC CTC CCC AAC TTA AGC CAT GTA ACT GAA AAT<br>Tyr Arg Lys Lys Ala Ser Leu Pro Asn Leu Ser His Val Thr Glu Asn<br>465                    470                    475                    480 | 1559 |
| CTA ATT ATA GGA GCA TTT GTT ACT GAG CCA CAG ATA ATA CAA GAG CGT<br>Leu Ile Ile Gly Ala Phe Val Thr Glu Pro Gln Ile Ile Gln Glu Arg<br>                            485                    490                    495 | 1607 |
| CCC CTC ACA AAT AAA TTA AAG CGT AAA AGG AGA CCT ACA TCA GGC CTT<br>Pro Leu Thr Asn Lys Leu Lys Arg Lys Arg Arg Pro Thr Ser Gly Leu<br>                500                    505                    510 | 1655 |
| CAT CCT GAG GAT TTT ATC AAG AAA GCA GAT TTG GCA GTT CAA AAG ACT<br>His Pro Glu Asp Phe Ile Lys Lys Ala Asp Leu Ala Val Gln Lys Thr<br>            515                    520                    525 | 1703 |
| CCT GAA ATG ATA AAT CAG GGA ACT AAC CAA ACG GAG CAG AAT GGT CAA<br>Pro Glu Met Ile Asn Gln Gly Thr Asn Gln Thr Glu Gln Asn Gly Gln<br>            530                    535                    540 | 1751 |
| GTG ATG AAT ATT ACT AAT AGT GGT CAT GAG AAT AAA ACA AAA GGT GAT<br>Val Met Asn Ile Thr Asn Ser Gly His Glu Asn Lys Thr Lys Gly Asp<br>545                    550                    555                    560 | 1799 |
| TCT ATT CAG AAT GAG AAA AAT CCT AAC CCA ATA GAA TCA CTC GAA AAA<br>Ser Ile Gln Asn Glu Lys Asn Pro Asn Pro Ile Glu Ser Leu Glu Lys<br>                    565                    570                    575 | 1847 |
| GAA TCT GCT TTC AAA ACG AAA GCT GAA CCT ATA AGC AGC AGT ATA AGC<br>Glu Ser Ala Phe Lys Thr Lys Ala Glu Pro Ile Ser Ser Ser Ile Ser<br>                580                    585                    590 | 1895 |
| AAT ATG GAA CTC GAA TTA AAT ATC CAC AAT TCA AAA GCA CCT AAA AAG<br>Asn Met Glu Leu Glu Leu Asn Ile His Asn Ser Lys Ala Pro Lys Lys<br>            595                    600                    605 | 1943 |
| AAT AGG CTG AGG AGG AAG TCT TCT ACC AGG CAT ATT CAT GCG CTT GAA<br>Asn Arg Leu Arg Arg Lys Ser Ser Thr Arg His Ile His Ala Leu Glu<br>610                      615                    620 | 1991 |
| CTA GTA GTC AGT AGA AAT CTA AGC CCA CCT AAT TGT ACT GAA TTG CAA | 2039 |

| | | | | | | | | | | | | | | | | |
|---|---|---|---|---|---|---|---|---|---|---|---|---|---|---|---|---|
|Leu|Val|Val|Ser|Arg|Asn|Leu|Ser|Pro|Pro|Asn|Cys|Thr|Glu|Leu|Gln| |
|625| | | |630| | | |635| | | |640| | | | |

| | | | | | | | | | | | | | | | | |
|---|---|---|---|---|---|---|---|---|---|---|---|---|---|---|---|---|
|ATT|GAT|AGT|TGT|TCT|AGC|AGT|GAA|GAG|ATA|AAG|AAA|AAA|AAG|TAC|AAC|2087|
|Ile|Asp|Ser|Cys|Ser|Ser|Ser|Glu|Glu|Ile|Lys|Lys|Lys|Lys|Tyr|Asn| |
| | | | |645| | | |650| | | | |655| | | |
|CAA|ATG|CCA|GTC|AGG|CAC|AGC|AGA|AAC|CTA|CAA|CTC|ATG|GAA|GGT|AAA|2135|
|Gln|Met|Pro|Val|Arg|His|Ser|Arg|Asn|Leu|Gln|Leu|Met|Glu|Gly|Lys| |
| | | |660| | | | |665| | | | |670| | | |
|GAA|CCT|GCA|ACT|GGA|GCC|AAG|AAG|AGT|AAC|AAG|CCA|AAT|GAA|CAG|ACA|2183|
|Glu|Pro|Ala|Thr|Gly|Ala|Lys|Lys|Ser|Asn|Lys|Pro|Asn|Glu|Gln|Thr| |
| | |675| | | |680| | | | |685| | | | | |
|AGT|AAA|AGA|CAT|GAC|AGC|GAT|ACT|TTC|CCA|GAG|CTG|AAG|TTA|ACA|AAT|2231|
|Ser|Lys|Arg|His|Asp|Ser|Asp|Thr|Phe|Pro|Glu|Leu|Lys|Leu|Thr|Asn| |
| |690| | | | |695| | | |700| | | | | | |
|GCA|CCT|GGT|TCT|TTT|ACT|AAG|TGT|TCA|AAT|ACC|AGT|GAA|CTT|AAA|GAA|2279|
|Ala|Pro|Gly|Ser|Phe|Thr|Lys|Cys|Ser|Asn|Thr|Ser|Glu|Leu|Lys|Glu| |
|705| | | |710| | | |715| | | |720| | | | |
|TTT|GTC|AAT|CCT|AGC|CTT|CCA|AGA|GAA|GAA|AAA|GAA|GAG|AAA|CTA|GAA|2327|
|Phe|Val|Asn|Pro|Ser|Leu|Pro|Arg|Glu|Glu|Lys|Glu|Glu|Lys|Leu|Glu| |
| | | | |725| | | |730| | | | |735| | | |
|ACA|GTT|AAA|GTG|TCT|AAT|AAT|GCT|GAA|GAC|CCC|AAA|GAT|CTC|ATG|TTA|2375|
|Thr|Val|Lys|Val|Ser|Asn|Asn|Ala|Glu|Asp|Pro|Lys|Asp|Leu|Met|Leu| |
| | | |740| | | |745| | | | |750| | | | |
|AGT|GGA|GAA|AGG|GTT|TTG|CAA|ACT|GAA|AGA|TCT|GTA|GAG|AGT|AGC|AGT|2423|
|Ser|Gly|Glu|Arg|Val|Leu|Gln|Thr|Glu|Arg|Ser|Val|Glu|Ser|Ser|Ser| |
| | |755| | | |760| | | | |765| | | | | |
|ATT|TCA|TTG|GTA|CCT|GGT|ACT|GAT|TAT|GGC|ACT|CAG|GAA|AGT|ATC|TCG|2471|
|Ile|Ser|Leu|Val|Pro|Gly|Thr|Asp|Tyr|Gly|Thr|Gln|Glu|Ser|Ile|Ser| |
| |770| | | | |775| | | |780| | | | | | |
|TTA|CTG|GAA|GTT|AGC|ACT|CTA|GGG|AAG|GCA|AAA|ACA|GAA|CCA|AAT|AAA|2519|
|Leu|Leu|Glu|Val|Ser|Thr|Leu|Gly|Lys|Ala|Lys|Thr|Glu|Pro|Asn|Lys| |
|785| | | |790| | | |795| | | |800| | | | |
|TGT|GTG|AGT|CAG|TGT|GCA|GCA|TTT|GAA|AAC|CCC|AAG|GGA|CTA|ATT|CAT|2567|
|Cys|Val|Ser|Gln|Cys|Ala|Ala|Phe|Glu|Asn|Pro|Lys|Gly|Leu|Ile|His| |
| | | | |805| | | |810| | | | |815| | | |
|GGT|TGT|TCC|AAA|GAT|AAT|AGA|AAT|GAC|ACA|GAA|GGC|TTT|AAG|TAT|CCA|2615|
|Gly|Cys|Ser|Lys|Asp|Asn|Arg|Asn|Asp|Thr|Glu|Gly|Phe|Lys|Tyr|Pro| |
| | | |820| | | |825| | | | |830| | | | |
|TTG|GGA|CAT|GAA|GTT|AAC|CAC|AGT|CGG|GAA|ACA|AGC|ATA|GAA|ATG|GAA|2663|
|Leu|Gly|His|Glu|Val|Asn|His|Ser|Arg|Glu|Thr|Ser|Ile|Glu|Met|Glu| |
| | |835| | | |840| | | | |845| | | | | |
|GAA|AGT|GAA|CTT|GAT|GCT|CAG|TAT|TTG|CAG|AAT|ACA|TTC|AAG|GTT|TCA|2711|
|Glu|Ser|Glu|Leu|Asp|Ala|Gln|Tyr|Leu|Gln|Asn|Thr|Phe|Lys|Val|Ser| |
| |850| | | | |855| | | |860| | | | | | |
|AAG|CGC|CAG|TCA|TTT|GCT|CCG|TTT|TCA|AAT|CCA|GGA|AAT|GCA|GAA|GAG|2759|
|Lys|Arg|Gln|Ser|Phe|Ala|Pro|Phe|Ser|Asn|Pro|Gly|Asn|Ala|Glu|Glu| |
|865| | | |870| | | |875| | | |880| | | | |
|GAA|TGT|GCA|ACA|TTC|TCT|GCC|CAC|TCT|GGG|TCC|TTA|AAG|AAA|CAA|AGT|2807|
|Glu|Cys|Ala|Thr|Phe|Ser|Ala|His|Ser|Gly|Ser|Leu|Lys|Lys|Gln|Ser| |
| | | | |885| | | |890| | | | |895| | | |
|CCA|AAA|GTC|ACT|TTT|GAA|TGT|GAA|CAA|AAG|GAA|GAA|AAT|CAA|GGA|AAG|2855|
|Pro|Lys|Val|Thr|Phe|Glu|Cys|Glu|Gln|Lys|Glu|Glu|Asn|Gln|Gly|Lys| |
| | | |900| | | |905| | | | |910| | | | |
|AAT|GAG|TCT|AAT|ATC|AAG|CCT|GTA|CAG|ACA|GTT|AAT|ATC|ACT|GCA|GGC|2903|
|Asn|Glu|Ser|Asn|Ile|Lys|Pro|Val|Gln|Thr|Val|Asn|Ile|Thr|Ala|Gly| |
| | |915| | | |920| | | | |925| | | | | |
|TTT|CCT|GTG|GTT|GGT|CAG|AAA|GAT|AAG|CCA|GTT|GAT|AAT|GCC|AAA|TGT|2951|
|Phe|Pro|Val|Val|Gly|Gln|Lys|Asp|Lys|Pro|Val|Asp|Asn|Ala|Lys|Cys| |
| |930| | | | |935| | | |940| | | | | | |
|AGT|ATC|AAA|GGA|GGC|TCT|AGG|TTT|TGT|CTA|TCA|TCT|CAG|TTC|AGA|GGC|2999|

```
Ser Ile Lys Gly Gly Ser Arg Phe Cys Leu Ser Ser Gln Phe Arg Gly
945                 950                 955                 960

AAC GAA ACT GGA CTC ATT ACT CCA AAT AAA CAT GGA CTT TTA CAA AAC         3047
Asn Glu Thr Gly Leu Ile Thr Pro Asn Lys His Gly Leu Leu Gln Asn
                965                 970                 975

CCA TAT CGT ATA CCA CCA CTT TTT CCC ATC AAG TCA TTT GTT AAA ACT         3095
Pro Tyr Arg Ile Pro Pro Leu Phe Pro Ile Lys Ser Phe Val Lys Thr
            980                 985                 990

AAA TGT AAG AAA AAT CTG CTA GAG GAA AAC TTT GAG GAA CAT TCA ATG         3143
Lys Cys Lys Lys Asn Leu Leu Glu Glu Asn Phe Glu Glu His Ser Met
        995                 1000                1005

TCA CCT GAA AGA GAA ATG GGA AAT GAG AAC ATT CCA AGT ACA GTG AGC         3191
Ser Pro Glu Arg Glu Met Gly Asn Glu Asn Ile Pro Ser Thr Val Ser
    1010                1015                1020

ACA ATT AGC CGT AAT AAC ATT AGA GAA AAT GTT TTT AAA GAA GCC AGC         3239
Thr Ile Ser Arg Asn Asn Ile Arg Glu Asn Val Phe Lys Glu Ala Ser
1025                1030                1035                1040

TCA AGC AAT ATT AAT GAA GTA GGT TCC AGT ACT AAT GAA GTG GGC TCC         3287
Ser Ser Asn Ile Asn Glu Val Gly Ser Ser Thr Asn Glu Val Gly Ser
                1045                1050                1055

AGT ATT AAT GAA ATA GGT TCC AGT GAT GAA AAC ATT CAA GCA GAA CTA         3335
Ser Ile Asn Glu Ile Gly Ser Ser Asp Glu Asn Ile Gln Ala Glu Leu
            1060                1065                1070

GGT AGA AAC AGA GGG CCA AAA TTG AAT GCT ATG CTT AGA TTA GGG GTT         3383
Gly Arg Asn Arg Gly Pro Lys Leu Asn Ala Met Leu Arg Leu Gly Val
        1075                1080                1085

TTG CAA CCT GAG GTC TAT AAA CAA AGT CTT CCT GGA AGT AAT TGT AAG         3431
Leu Gln Pro Glu Val Tyr Lys Gln Ser Leu Pro Gly Ser Asn Cys Lys
    1090                1095                1100

CAT CCT GAA ATA AAA AAG CAA GAA TAT GAA GAA GTA GTT CAG ACT GTT         3479
His Pro Glu Ile Lys Lys Gln Glu Tyr Glu Glu Val Val Gln Thr Val
1105                1110                1115                1120

AAT ACA GAT TTC TCT CCA TAT CTG ATT TCA GAT AAC TTA GAA CAG CCT         3527
Asn Thr Asp Phe Ser Pro Tyr Leu Ile Ser Asp Asn Leu Glu Gln Pro
                1125                1130                1135

ATG GGA AGT AGT CAT GCA TCT CAG GTT TGT TCT GAG ACA CCT GAT GAC         3575
Met Gly Ser Ser His Ala Ser Gln Val Cys Ser Glu Thr Pro Asp Asp
            1140                1145                1150

CTG TTA GAT GAT GGT GAA ATA AAG GAA GAT ACT AGT TTT GCT GAA AAT         3623
Leu Leu Asp Asp Gly Glu Ile Lys Glu Asp Thr Ser Phe Ala Glu Asn
        1155                1160                1165

GAC ATT AAG GAA AGT TCT GCT GTT TTT AGC AAA AGC GTC CAG AAA GGA         3671
Asp Ile Lys Glu Ser Ser Ala Val Phe Ser Lys Ser Val Gln Lys Gly
    1170                1175                1180

GAG CTT AGC AGG AGT CCT AGC CCT TTC ACC CAT ACA CAT TTG GCT CAG         3719
Glu Leu Ser Arg Ser Pro Ser Pro Phe Thr His Thr His Leu Ala Gln
1185                1190                1195                1200

GGT TAC CGA AGA GGG GCC AAG AAA TTA GAG TCC TCA GAA GAG AAC TTA         3767
Gly Tyr Arg Arg Gly Ala Lys Lys Leu Glu Ser Ser Glu Glu Asn Leu
                1205                1210                1215

TCT AGT GAG GAT GAA GAG CTT CCC TGC TTC CAA CAC TTG TTA TTT GGT         3815
Ser Ser Glu Asp Glu Glu Leu Pro Cys Phe Gln His Leu Leu Phe Gly
            1220                1225                1230

AAA GTA AAC AAT ATA CCT TCT CAG TCT ACT AGG CAT AGC ACC GTT GCT         3863
Lys Val Asn Asn Ile Pro Ser Gln Ser Thr Arg His Ser Thr Val Ala
        1235                1240                1245

ACC GAG TGT CTG TCT AAG AAC ACA GAG GAG AAT TTA TTA TCA TTG AAG         3911
Thr Glu Cys Leu Ser Lys Asn Thr Glu Glu Asn Leu Leu Ser Leu Lys
    1250                1255                1260

AAT AGC TTA AAT GAC TGC AGT AAC CAG GTA ATA TTG GCA AAG GCA TCT         3959
```

```
                                          -continued

Asn Ser Leu Asn Asp Cys Ser Asn Gln Val Ile Leu Ala Lys Ala Ser
1265                1270                1275                1280

CAG GAA CAT CAC CTT AGT GAG GAA ACA AAA TGT TCT GCT AGC TTG TTT        4007
Gln Glu His His Leu Ser Glu Glu Thr Lys Cys Ser Ala Ser Leu Phe
            1285                1290                1295

TCT TCA CAG TGC AGT GAA TTG GAA GAC TTG ACT GCA AAT ACA AAC ACC        4055
Ser Ser Gln Cys Ser Glu Leu Glu Asp Leu Thr Ala Asn Thr Asn Thr
        1300                1305                1310

CAG GAT CCT TTC TTG ATT GGT TCT TCC AAA CAA ATG AGG CAT CAG TCT        4103
Gln Asp Pro Phe Leu Ile Gly Ser Ser Lys Gln Met Arg His Gln Ser
            1315                1320                1325

GAA AGC CAG GGA GTT GGT CTG AGT GAC AAG GAA TTG GTT TCA GAT GAT        4151
Glu Ser Gln Gly Val Gly Leu Ser Asp Lys Glu Leu Val Ser Asp Asp
        1330                1335                1340

GAA GAA AGA GGA ACG GGC TTG GAA GAA AAT AAT CAA GAA GAG CAA AGC        4199
Glu Glu Arg Gly Thr Gly Leu Glu Glu Asn Asn Gln Glu Glu Gln Ser
1345                1350                1355                1360

ATG GAT TCA AAC TTA GGT GAA GCA GCA TCT GGG TGT GAG AGT GAA ACA        4247
Met Asp Ser Asn Leu Gly Glu Ala Ala Ser Gly Cys Glu Ser Glu Thr
            1365                1370                1375

AGC GTC TCT GAA GAC TGC TCA GGG CTA TCC TCT CAG AGT GAC ATT TTA        4295
Ser Val Ser Glu Asp Cys Ser Gly Leu Ser Ser Gln Ser Asp Ile Leu
        1380                1385                1390

ACC ACT CAG CAG AGG GAT ACC ATG CAA CAT AAC CTG ATA AAG CTC CAG        4343
Thr Thr Gln Gln Arg Asp Thr Met Gln His Asn Leu Ile Lys Leu Gln
            1395                1400                1405

CAG GAA ATG GCT GAA CTA GAA GCT GTG TTA GAA CAG CAT GGG AGC CAG        4391
Gln Glu Met Ala Glu Leu Glu Ala Val Leu Glu Gln His Gly Ser Gln
        1410                1415                1420

CCT TCT AAC AGC TAC CCT TCC ATC ATA AGT GAC TCT TCT GCC CTT GAG        4439
Pro Ser Asn Ser Tyr Pro Ser Ile Ile Ser Asp Ser Ser Ala Leu Glu
1425                1430                1435                1440

GAC CTG CGA AAT CCA GAA CAA AGC ACA TCA GAA AAA GCA GTA TTA ACT        4487
Asp Leu Arg Asn Pro Glu Gln Ser Thr Ser Glu Lys Ala Val Leu Thr
            1445                1450                1455

TCA CAG AAA AGT AGT GAA TAC CCT ATA AGC CAG AAT CCA GAA GGC CTT        4535
Ser Gln Lys Ser Ser Glu Tyr Pro Ile Ser Gln Asn Pro Glu Gly Leu
        1460                1465                1470

TCT GCT GAC AAG TTT GAG GTG TCT GCA GAT AGT TCT ACC AGT AAA AAT        4583
Ser Ala Asp Lys Phe Glu Val Ser Ala Asp Ser Ser Thr Ser Lys Asn
            1475                1480                1485

AAA GAA CCA GGA GTG GAA AGG TCA TCC CCT TCT AAA TGC CCA TCA TTA        4631
Lys Glu Pro Gly Val Glu Arg Ser Ser Pro Ser Lys Cys Pro Ser Leu
        1490                1495                1500

GAT GAT AGG TGG TAC ATG CAC AGT TGC TCT GGG AGT CTT CAG AAT AGA        4679
Asp Asp Arg Trp Tyr Met His Ser Cys Ser Gly Ser Leu Gln Asn Arg
1505                1510                1515                1520

AAC TAC CCA TCT CAA GAG GAG CTC ATT AAG GTT GTT GAT GTG GAG GAG        4727
Asn Tyr Pro Ser Gln Glu Glu Leu Ile Lys Val Val Asp Val Glu Glu
            1525                1530                1535

CAA CAG CTG GAA GAG TCT GGG CCA CAC GAT TTG ACG GAA ACA TCT TAC        4775
Gln Gln Leu Glu Glu Ser Gly Pro His Asp Leu Thr Glu Thr Ser Tyr
        1540                1545                1550

TTG CCA AGG CAA GAT CTA GAG GGA ACC CCT TAC CTG GAA TCT GGA ATC        4823
Leu Pro Arg Gln Asp Leu Glu Gly Thr Pro Tyr Leu Glu Ser Gly Ile
        1555                1560                1565

AGC CTC TTC TCT GAT GAC CCT GAA TCT GAT CCT TCT GAA GAC AGA GCC        4871
Ser Leu Phe Ser Asp Asp Pro Glu Ser Asp Pro Ser Glu Asp Arg Ala
        1570                1575                1580

CCA GAG TCA GCT CGT GTT GGC AAC ATA CCA TCT TCA ACC TCT GCA TTG        4919
```

```
          Pro Glu Ser Ala Arg Val Gly Asn Ile Pro Ser Ser Thr Ser Ala Leu
          1585                1590                1595                1600

AAA GTT CCC CAA TTG AAA GTT GCA GAA TCT GCC CAG AGT CCA GCT GCT            4967
Lys Val Pro Gln Leu Lys Val Ala Glu Ser Ala Gln Ser Pro Ala Ala
                    1605                1610                1615

GCT CAT ACT ACT GAT ACT GCT GGG TAT AAT GCA ATG GAA GAA AGT GTG            5015
Ala His Thr Thr Asp Thr Ala Gly Tyr Asn Ala Met Glu Glu Ser Val
            1620                1625                1630

AGC AGG GAG AAG CCA GAA TTG ACA GCT TCA ACA GAA AGG GTC AAC AAA            5063
Ser Arg Glu Lys Pro Glu Leu Thr Ala Ser Thr Glu Arg Val Asn Lys
        1635                1640                1645

AGA ATG TCC ATG GTG GTG TCT GGC CTG ACC CCA GAA GAA TTT ATG CTC            5111
Arg Met Ser Met Val Val Ser Gly Leu Thr Pro Glu Glu Phe Met Leu
    1650                1655                1660

GTG TAC AAG TTT GCC AGA AAA CAC CAC ATC ACT TTA ACT AAT CTA ATT            5159
Val Tyr Lys Phe Ala Arg Lys His His Ile Thr Leu Thr Asn Leu Ile
1665                1670                1675                1680

ACT GAA GAG ACT ACT CAT GTT GTT ATG AAA ACA GAT GCT GAG TTT GTG            5207
Thr Glu Glu Thr Thr His Val Val Met Lys Thr Asp Ala Glu Phe Val
                    1685                1690                1695

TGT GAA CGG ACA CTG AAA TAT TTT CTA GGA ATT GCG GGA GGA AAA TGG            5255
Cys Glu Arg Thr Leu Lys Tyr Phe Leu Gly Ile Ala Gly Gly Lys Trp
            1700                1705                1710

GTA GTT AGC TAT TTC TGG GTG ACC CAG TCT ATT AAA GAA AGA AAA ATG            5303
Val Val Ser Tyr Phe Trp Val Thr Gln Ser Ile Lys Glu Arg Lys Met
        1715                1720                1725

CTG AAT GAG CAT GAT TTT GAA GTC AGA GGA GAT GTG GTC AAT GGA AGA            5351
Leu Asn Glu His Asp Phe Glu Val Arg Gly Asp Val Val Asn Gly Arg
    1730                1735                1740

AAC CAC CAA GGT CCA AAG CGA GCA AGA GAA TCC CAG GAC AGA AAG ATC            5399
Asn His Gln Gly Pro Lys Arg Ala Arg Glu Ser Gln Asp Arg Lys Ile
1745                1750                1755                1760

TTC AGG GGG CTA GAA ATC TGT TGC TAT GGG CCC TTC ACC AAC ATG CCC            5447
Phe Arg Gly Leu Glu Ile Cys Cys Tyr Gly Pro Phe Thr Asn Met Pro
                    1765                1770                1775

ACA GAT CAA CTG GAA TGG ATG GTA CAG CTG TGT GGT GCT TCT GTG GTG            5495
Thr Asp Gln Leu Glu Trp Met Val Gln Leu Cys Gly Ala Ser Val Val
            1780                1785                1790

AAG GAG CTT TCA TCA TTC ACC CTT GGC ACA GGT GTC CAC CCA ATT GTG            5543
Lys Glu Leu Ser Ser Phe Thr Leu Gly Thr Gly Val His Pro Ile Val
        1795                1800                1805

GTT GTG CAG CCA GAT GCC TGG ACA GAG GAC AAT GGC TTC CAT GCA ATT            5591
Val Val Gln Pro Asp Ala Trp Thr Glu Asp Asn Gly Phe His Ala Ile
    1810                1815                1820

GGG CAG ATG TGT GAG GCA CCT GTG GTG ACC CGA GAG TGG GTG TTG GAC            5639
Gly Gln Met Cys Glu Ala Pro Val Val Thr Arg Glu Trp Val Leu Asp
1825                1830                1835                1840

AGT GTA GCA CTC TAC CAG TGC CAG GAG CTG GAC ACC TAC CTG ATA CCC            5687
Ser Val Ala Leu Tyr Gln Cys Gln Glu Leu Asp Thr Tyr Leu Ile Pro
                    1845                1850                1855

CAG ATC CCC CAC AGC CAC TAC TGA CTGCAGCCAG CCACAGGTAC AGAGCCACAG           5741
Gln Ile Pro His Ser His Tyr
            1860

GACCCCAAGA ATGAGCTTAC AAAGTGGCCT TTCCAGGCCC TGGGAGCTCC TCTCACTCTT          5801

CAGTCCTTCT ACTGTCCTGG CTACTAAATA TTTTATGTAC ATCAGCCTGA AAAGGACTTC          5861

TGGCTATGCA AGGGTCCCTT AAAGATTTTC TGCTTGAAGT CTCCCTTGGA AAT                 5914
```

( 2 ) INFORMATION FOR SEQ ID NO:2:

( i ) SEQUENCE CHARACTERISTICS:
  ( A ) LENGTH: 1863 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

```
Met Asp Leu Ser Ala Leu Arg Val Glu Glu Val Gln Asn Val Ile Asn
 1               5                  10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
            85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
            165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
            245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
            325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
370                 375                 380
```

| | | | | | | | | | | | | | | |
|---|---|---|---|---|---|---|---|---|---|---|---|---|---|---|
| Trp | Phe | Ser | Arg | Ser | Asp | Glu | Leu | Leu | Gly | Ser | Asp | Asp | Ser | His | Asp |
| 385 | | | | 390 | | | | | 395 | | | | | 400 |
| Gly | Glu | Ser | Glu | Ser | Asn | Ala | Lys | Val | Ala | Asp | Val | Leu | Asp | Val | Leu |
| | | | | 405 | | | | 410 | | | | | 415 | | |
| Asn | Glu | Val | Asp | Glu | Tyr | Ser | Gly | Ser | Ser | Glu | Lys | Ile | Asp | Leu | Leu |
| | | | 420 | | | | | 425 | | | | | 430 | | |
| Ala | Ser | Asp | Pro | His | Glu | Ala | Leu | Ile | Cys | Lys | Ser | Glu | Arg | Val | His |
| | | 435 | | | | | 440 | | | | | 445 | | | |
| Ser | Lys | Ser | Val | Glu | Ser | Asn | Ile | Glu | Asp | Lys | Ile | Phe | Gly | Lys | Thr |
| | 450 | | | | | 455 | | | | | 460 | | | | |
| Tyr | Arg | Lys | Lys | Ala | Ser | Leu | Pro | Asn | Leu | Ser | His | Val | Thr | Glu | Asn |
| 465 | | | | | 470 | | | | | 475 | | | | | 480 |
| Leu | Ile | Ile | Gly | Ala | Phe | Val | Thr | Glu | Pro | Gln | Ile | Ile | Gln | Glu | Arg |
| | | | | 485 | | | | | 490 | | | | | 495 | |
| Pro | Leu | Thr | Asn | Lys | Leu | Lys | Arg | Lys | Arg | Arg | Pro | Thr | Ser | Gly | Leu |
| | | | | 500 | | | | | 505 | | | | 510 | | |
| His | Pro | Glu | Asp | Phe | Ile | Lys | Lys | Ala | Asp | Leu | Ala | Val | Gln | Lys | Thr |
| | | | 515 | | | | 520 | | | | | 525 | | | |
| Pro | Glu | Met | Ile | Asn | Gln | Gly | Thr | Asn | Gln | Thr | Glu | Gln | Asn | Gly | Gln |
| | | 530 | | | | 535 | | | | | 540 | | | | |
| Val | Met | Asn | Ile | Thr | Asn | Ser | Gly | His | Glu | Asn | Lys | Thr | Lys | Gly | Asp |
| 545 | | | | | 550 | | | | | 555 | | | | | 560 |
| Ser | Ile | Gln | Asn | Glu | Lys | Asn | Pro | Asn | Pro | Ile | Glu | Ser | Leu | Glu | Lys |
| | | | | 565 | | | | | 570 | | | | | 575 | |
| Glu | Ser | Ala | Phe | Lys | Thr | Lys | Ala | Glu | Pro | Ile | Ser | Ser | Ser | Ile | Ser |
| | | | 580 | | | | | 585 | | | | | 590 | | |
| Asn | Met | Glu | Leu | Glu | Leu | Asn | Ile | His | Asn | Ser | Lys | Ala | Pro | Lys | Lys |
| | | 595 | | | | | 600 | | | | | 605 | | | |
| Asn | Arg | Leu | Arg | Arg | Lys | Ser | Thr | Arg | His | Ile | His | Ala | Leu | Glu |
| | 610 | | | | | 615 | | | | | 620 | | | | |
| Leu | Val | Val | Ser | Arg | Asn | Leu | Ser | Pro | Pro | Asn | Cys | Thr | Glu | Leu | Gln |
| 625 | | | | | 630 | | | | | 635 | | | | | 640 |
| Ile | Asp | Ser | Cys | Ser | Ser | Ser | Glu | Glu | Ile | Lys | Lys | Lys | Lys | Tyr | Asn |
| | | | | 645 | | | | | 650 | | | | | 655 | |
| Gln | Met | Pro | Val | Arg | His | Ser | Arg | Asn | Leu | Gln | Leu | Met | Glu | Gly | Lys |
| | | | 660 | | | | | 665 | | | | | 670 | | |
| Glu | Pro | Ala | Thr | Gly | Ala | Lys | Lys | Ser | Asn | Lys | Pro | Asn | Glu | Gln | Thr |
| | | | 675 | | | | 680 | | | | | 685 | | | |
| Ser | Lys | Arg | His | Asp | Ser | Asp | Thr | Phe | Pro | Glu | Leu | Lys | Leu | Thr | Asn |
| | 690 | | | | | 695 | | | | | 700 | | | | |
| Ala | Pro | Gly | Ser | Phe | Thr | Lys | Cys | Ser | Asn | Thr | Ser | Glu | Leu | Lys | Glu |
| 705 | | | | | 710 | | | | | 715 | | | | | 720 |
| Phe | Val | Asn | Pro | Ser | Leu | Pro | Arg | Glu | Glu | Lys | Glu | Glu | Lys | Leu | Glu |
| | | | | 725 | | | | | 730 | | | | | 735 | |
| Thr | Val | Lys | Val | Ser | Asn | Asn | Ala | Glu | Asp | Pro | Lys | Asp | Leu | Met | Leu |
| | | | 740 | | | | | 745 | | | | | 750 | | |
| Ser | Gly | Glu | Arg | Val | Leu | Gln | Thr | Glu | Arg | Ser | Val | Glu | Ser | Ser | Ser |
| | | | 755 | | | | | 760 | | | | | 765 | | |
| Ile | Ser | Leu | Val | Pro | Gly | Thr | Asp | Tyr | Gly | Thr | Gln | Glu | Ser | Ile | Ser |
| | | 770 | | | | | 775 | | | | | 780 | | | |
| Leu | Leu | Glu | Val | Ser | Thr | Leu | Gly | Lys | Ala | Lys | Thr | Glu | Pro | Asn | Lys |
| 785 | | | | | 790 | | | | | 795 | | | | | 800 |
| Cys | Val | Ser | Gln | Cys | Ala | Ala | Phe | Glu | Asn | Pro | Lys | Gly | Leu | Ile | His |

-continued

```
                    805                         810                         815
Gly  Cys  Ser  Lys  Asp  Asn  Arg  Asn  Asp  Thr  Glu  Gly  Phe  Lys  Tyr  Pro
               820                      825                      830
Leu  Gly  His  Glu  Val  Asn  His  Ser  Arg  Glu  Thr  Ser  Ile  Glu  Met  Glu
          835                      840                      845
Glu  Ser  Glu  Leu  Asp  Ala  Gln  Tyr  Leu  Gln  Asn  Thr  Phe  Lys  Val  Ser
     850                      855                      860
Lys  Arg  Gln  Ser  Phe  Ala  Pro  Phe  Ser  Asn  Pro  Gly  Asn  Ala  Glu  Glu
865                           870                      875                      880
Glu  Cys  Ala  Thr  Phe  Ser  Ala  His  Ser  Gly  Ser  Leu  Lys  Lys  Gln  Ser
                    885                      890                          895
Pro  Lys  Val  Thr  Phe  Glu  Cys  Glu  Gln  Lys  Glu  Glu  Asn  Gln  Gly  Lys
               900                      905                      910
Asn  Glu  Ser  Asn  Ile  Lys  Pro  Val  Gln  Thr  Val  Asn  Ile  Thr  Ala  Gly
          915                      920                      925
Phe  Pro  Val  Val  Gly  Gln  Lys  Asp  Lys  Pro  Val  Asp  Asn  Ala  Lys  Cys
     930                      935                      940
Ser  Ile  Lys  Gly  Gly  Ser  Arg  Phe  Cys  Leu  Ser  Ser  Gln  Phe  Arg  Gly
945                           950                      955                      960
Asn  Glu  Thr  Gly  Leu  Ile  Thr  Pro  Asn  Lys  His  Gly  Leu  Leu  Gln  Asn
                    965                      970                          975
Pro  Tyr  Arg  Ile  Pro  Pro  Leu  Phe  Pro  Ile  Lys  Ser  Phe  Val  Lys  Thr
               980                      985                      990
Lys  Cys  Lys  Lys  Asn  Leu  Leu  Glu  Glu  Asn  Phe  Glu  Glu  His  Ser  Met
          995                      1000                     1005
Ser  Pro  Glu  Arg  Glu  Met  Gly  Asn  Glu  Asn  Ile  Pro  Ser  Thr  Val  Ser
     1010                     1015                     1020
Thr  Ile  Ser  Arg  Asn  Asn  Ile  Arg  Glu  Asn  Val  Phe  Lys  Glu  Ala  Ser
1025                          1030                     1035                     1040
Ser  Ser  Asn  Ile  Asn  Glu  Val  Gly  Ser  Ser  Thr  Asn  Glu  Val  Gly  Ser
                    1045                     1050                     1055
Ser  Ile  Asn  Glu  Ile  Gly  Ser  Ser  Asp  Glu  Asn  Ile  Gln  Ala  Glu  Leu
               1060                     1065                     1070
Gly  Arg  Asn  Arg  Gly  Pro  Lys  Leu  Asn  Ala  Met  Leu  Arg  Leu  Gly  Val
          1075                     1080                     1085
Leu  Gln  Pro  Glu  Val  Tyr  Lys  Gln  Ser  Leu  Pro  Gly  Ser  Asn  Cys  Lys
     1090                     1095                     1100
His  Pro  Glu  Ile  Lys  Lys  Gln  Glu  Tyr  Glu  Glu  Val  Val  Gln  Thr  Val
1105                          1110                     1115                     1120
Asn  Thr  Asp  Phe  Ser  Pro  Tyr  Leu  Ile  Ser  Asp  Asn  Leu  Glu  Gln  Pro
                    1125                     1130                     1135
Met  Gly  Ser  Ser  His  Ala  Ser  Gln  Val  Cys  Ser  Glu  Thr  Pro  Asp  Asp
               1140                     1145                     1150
Leu  Leu  Asp  Asp  Gly  Glu  Ile  Lys  Glu  Asp  Thr  Ser  Phe  Ala  Glu  Asn
          1155                     1160                     1165
Asp  Ile  Lys  Glu  Ser  Ser  Ala  Val  Phe  Ser  Lys  Ser  Val  Gln  Lys  Gly
     1170                     1175                     1180
Glu  Leu  Ser  Arg  Ser  Pro  Ser  Pro  Phe  Thr  His  Thr  His  Leu  Ala  Gln
1185                          1190                     1195                     1200
Gly  Tyr  Arg  Arg  Gly  Ala  Lys  Lys  Leu  Glu  Ser  Ser  Glu  Glu  Asn  Leu
                    1205                     1210                     1215
Ser  Ser  Glu  Asp  Glu  Glu  Leu  Pro  Cys  Phe  Gln  His  Leu  Leu  Phe  Gly
               1220                     1225                     1230
```

Lys Val Asn Asn Ile Pro Ser Gln Ser Thr Arg His Ser Thr Val Ala
1235                 1240                 1245

Thr Glu Cys Leu Ser Lys Asn Thr Glu Glu Asn Leu Leu Ser Leu Lys
1250                 1255                 1260

Asn Ser Leu Asn Asp Cys Ser Asn Gln Val Ile Leu Ala Lys Ala Ser
1265                 1270                 1275                 1280

Gln Glu His His Leu Ser Glu Glu Thr Lys Cys Ser Ala Ser Leu Phe
                 1285                 1290                 1295

Ser Ser Gln Cys Ser Glu Leu Glu Asp Leu Thr Ala Asn Thr Asn Thr
                 1300                 1305                 1310

Gln Asp Pro Phe Leu Ile Gly Ser Ser Lys Gln Met Arg His Gln Ser
                 1315                 1320                 1325

Glu Ser Gln Gly Val Gly Leu Ser Asp Lys Glu Leu Val Ser Asp Asp
1330                 1335                 1340

Glu Glu Arg Gly Thr Gly Leu Glu Glu Asn Asn Gln Glu Glu Gln Ser
1345                 1350                 1355                 1360

Met Asp Ser Asn Leu Gly Glu Ala Ala Ser Gly Cys Glu Ser Glu Thr
                 1365                 1370                 1375

Ser Val Ser Glu Asp Cys Ser Gly Leu Ser Ser Gln Ser Asp Ile Leu
                 1380                 1385                 1390

Thr Thr Gln Gln Arg Asp Thr Met Gln His Asn Leu Ile Lys Leu Gln
                 1395                 1400                 1405

Gln Glu Met Ala Glu Leu Glu Ala Val Leu Glu Gln His Gly Ser Gln
1410                 1415                 1420

Pro Ser Asn Ser Tyr Pro Ser Ile Ile Ser Asp Ser Ser Ala Leu Glu
1425                 1430                 1435                 1440

Asp Leu Arg Asn Pro Glu Gln Ser Thr Ser Glu Lys Ala Val Leu Thr
                 1445                 1450                 1455

Ser Gln Lys Ser Ser Glu Tyr Pro Ile Ser Gln Asn Pro Glu Gly Leu
                 1460                 1465                 1470

Ser Ala Asp Lys Phe Glu Val Ser Ala Asp Ser Ser Thr Ser Lys Asn
                 1475                 1480                 1485

Lys Glu Pro Gly Val Glu Arg Ser Ser Pro Ser Lys Cys Pro Ser Leu
1490                 1495                 1500

Asp Asp Arg Trp Tyr Met His Ser Cys Ser Gly Ser Leu Gln Asn Arg
1505                 1510                 1515                 1520

Asn Tyr Pro Ser Gln Glu Glu Leu Ile Lys Val Val Asp Val Glu Glu
                 1525                 1530                 1535

Gln Gln Leu Glu Glu Ser Gly Pro His Asp Leu Thr Glu Thr Ser Tyr
                 1540                 1545                 1550

Leu Pro Arg Gln Asp Leu Glu Gly Thr Pro Tyr Leu Glu Ser Gly Ile
                 1555                 1560                 1565

Ser Leu Phe Ser Asp Asp Pro Glu Ser Asp Pro Ser Glu Asp Arg Ala
                 1570                 1575                 1580

Pro Glu Ser Ala Arg Val Gly Asn Ile Pro Ser Ser Thr Ser Ala Leu
1585                 1590                 1595                 1600

Lys Val Pro Gln Leu Lys Val Ala Glu Ser Ala Gln Ser Pro Ala Ala
                 1605                 1610                 1615

Ala His Thr Thr Asp Thr Ala Gly Tyr Asn Ala Met Glu Glu Ser Val
                 1620                 1625                 1630

Ser Arg Glu Lys Pro Glu Leu Thr Ala Ser Thr Glu Arg Val Asn Lys
1635                 1640                 1645

Arg Met Ser Met Val Val Ser Gly Leu Thr Pro Glu Glu Phe Met Leu
1650                 1655                 1660

Val Tyr Lys Phe Ala Arg Lys His His Ile Thr Leu Thr Asn Leu Ile
1665               1670              1675              1680

Thr Glu Glu Thr Thr His Val Val Met Lys Thr Asp Ala Glu Phe Val
                1685              1690              1695

Cys Glu Arg Thr Leu Lys Tyr Phe Leu Gly Ile Ala Gly Gly Lys Trp
            1700              1705              1710

Val Val Ser Tyr Phe Trp Val Thr Gln Ser Ile Lys Glu Arg Lys Met
        1715              1720              1725

Leu Asn Glu His Asp Phe Glu Val Arg Gly Asp Val Val Asn Gly Arg
        1730              1735              1740

Asn His Gln Gly Pro Lys Arg Ala Arg Glu Ser Gln Asp Arg Lys Ile
1745              1750              1755              1760

Phe Arg Gly Leu Glu Ile Cys Cys Tyr Gly Pro Phe Thr Asn Met Pro
                1765              1770              1775

Thr Asp Gln Leu Glu Trp Met Val Gln Leu Cys Gly Ala Ser Val Val
            1780              1785              1790

Lys Glu Leu Ser Ser Phe Thr Leu Gly Thr Gly Val His Pro Ile Val
        1795              1800              1805

Val Val Gln Pro Asp Ala Trp Thr Glu Asp Asn Gly Phe His Ala Ile
        1810              1815              1820

Gly Gln Met Cys Glu Ala Pro Val Val Thr Arg Glu Trp Val Leu Asp
1825              1830              1835              1840

Ser Val Ala Leu Tyr Gln Cys Gln Glu Leu Asp Thr Tyr Leu Ile Pro
                1845              1850              1855

Gln Ile Pro His Ser His Tyr
                1860

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Homo sapiens ( v i i ) IMMEDIATE SOURCE:
    ( B ) CLONE: s754A ( x i ) SEQUENCE DESCRIPTION: SEQ ID NO:3:

CTAGCCTGGG CAACAAACGA     20

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Homo sapiens ( v i i ) IMMEDIATE SOURCE:

(B) CLONE: s754 B (x i) SEQUENCE DESCRIPTION: SEQ ID NO:4:

GCAGGAAGCA GGAATGGAAC    20

(2) INFORMATION FOR SEQ ID NO:5:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (i i) MOLECULE TYPE: DNA (genomic)

(i i i) HYPOTHETICAL: NO (v i) ORIGINAL SOURCE:
  (A) ORGANISM: Homo sapiens (v i i) IMMEDIATE SOURCE:
  (B) CLONE: s975 A (x i) SEQUENCE DESCRIPTION: SEQ ID NO:5:

TAGGAGATGG ATTATTGGTG    20

(2) INFORMATION FOR SEQ ID NO:6:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (i i) MOLECULE TYPE: DNA (genomic)

(i i i) HYPOTHETICAL: NO (v i) ORIGINAL SOURCE:
  (A) ORGANISM: Homo sapiens (v i i) IMMEDIATE SOURCE:
  (B) CLONE: s975 B (x i) SEQUENCE DESCRIPTION: SEQ ID NO:6:

AGGCAACTTT GCAATGAGTG    20

(2) INFORMATION FOR SEQ ID NO:7:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (i i) MOLECULE TYPE: DNA (genomic)

(i i i) HYPOTHETICAL: NO (v i) ORIGINAL SOURCE:
  (A) ORGANISM: Homo sapiens (v i i) IMMEDIATE SOURCE:
  (B) CLONE: tdj1474 A (x i) SEQUENCE DESCRIPTION: SEQ ID NO:7:

CAGAGTGAGA CCTTGTCTCA AA    22

(2) INFORMATION FOR SEQ ID NO:8:

(i) SEQUENCE CHARACTERISTICS:
  (A) LENGTH: 23 base pairs ( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Homo sapiens ( v i i ) IMMEDIATE SOURCE:
( B ) CLONE: tdj1474 B ( x i ) SEQUENCE DESCRIPTION: SEQ ID NO:8:

TTCTGCAAAC ACCTTAAACT CAG 23

( 2 ) INFORMATION FOR SEQ ID NO:9:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Homo sapiens ( v i i ) IMMEDIATE SOURCE:
( B ) CLONE: tdj1239 A ( x i ) SEQUENCE DESCRIPTION: SEQ ID NO:9:

AACCTGGAAG GCAGAGGTTG 20

( 2 ) INFORMATION FOR SEQ ID NO:10:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Homo sapiens ( v i i ) IMMEDIATE SOURCE:
( B ) CLONE: tdj1239 B ( x i ) SEQUENCE DESCRIPTION: SEQ ID NO:10:

TCTGTACCTG CTAAGCAGTG G 21

( 2 ) INFORMATION FOR SEQ ID NO:11:

( i ) SEQUENCE CHARACTERISTICS:
( A ) LENGTH: 111 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( v i ) ORIGINAL SOURCE:
( A ) ORGANISM: Homo sapiens ( i x ) FEATURE:
    ( A ) NAME/KEY: CDS
    ( B ) LOCATION: 2..111

( x i ) SEQUENCE DESCRIPTION: SEQ ID NO:11:

```
G GKC TTA CTC TGT TGT CCC AGC TGG AGT ACA GWG TGC GAT CAT GAG          46
  Xaa Leu Leu Cys Cys Pro Ser Trp Ser Thr Xaa Cys Asp His Glu
  1865            1870                1875
GCT TAC TGT TGC TTG ACT CCT AGG CTC AAG CGA TCC TAT CAC CTC AGT        94
Ala Tyr Cys Cys Leu Thr Pro Arg Leu Lys Arg Ser Tyr His Leu Ser
1880            1885                1890                1895
CTC CAA GTA GCT GGA    CT                                              111
Leu Gln Val Ala Gly
                1900
```

( 2 ) INFORMATION FOR SEQ ID NO:12:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Xaa Leu Leu Cys Cys Pro Ser Trp Ser Thr Xaa Cys Asp His Glu Ala
1               5                   10                  15
Tyr Cys Cys Leu Thr Pro Arg Leu Lys Arg Ser Tyr His Leu Ser Leu
                20                  25                  30
Gln Val Ala Gly
            35
```

( 2 ) INFORMATION FOR SEQ ID NO:13:

( i ) SEQUENCE CHARACTERISTICS:
        ( A ) LENGTH: 1534 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:13:

```
GAGGCTAGAG GGCAGGCACT TTATGGCAAA CTCAGGTAGA ATTCTTCCTC TTCCGTCTCT    60
TTCCTTTTAC GTCATCGGGG AGACTGGGTG GCAATCGCAG CCCGAGAGAC GCATGGCTCT   120
TTCTGCCCTC CATCCTCTGA TGTACCTTGA TTTCGTATTC TGAGAGGCTG CTGCTTAGCG   180
GTAGCCCCTT GGTTTCCGTG GCAACGGAAA AGCGCGGGAA TTACAGATAA ATTAAAACTG   240
CGACTGCGCG GCGTGAGCTC GCTGAGACTT CCTGGACCCC GCACCAGGCT GTGGGGTTTC   300
TCAGATAACT GGGCCCCTGC GCTCAGGAGG CCTTCACCCT CTGCTCTGGG TAAAGGTAGT   360
AGAGTCCCGG GAAAGGGACA GGGGGCCCAA GTGATGCTCT GGGGTACTGG CGTGGGAGAG   420
TGGATTTCCG AAGCTGACAG ATGGGTATTC TTTGACGGGG GGTAGGGGCG GAACCTGAGA   480
GGCGTAAGGC GTTGTGAACC CTGGGGAGGG GGGCAGTTTG TAGGTCGCGA GGGAAGCGCT   540
GAGGATCAGG AAGGGGGCAC TGAGTGTCCG TGGGGGAATC CTCGTGATAG GAACTGGAAT   600
```

```
ATGCCTTGAG  GGGGACACTA  TGTCTTTAAA  AACGTCGGCT  GGTCATGAGG  TCAGGAGTTC      660

CAGACCAGCC  TGACCAACGT  GGTGAAACTC  CGTCTCTACT  AAAAATACNA  AAATTAGCCG      720

GGCGTGGTGC  CGCTCCAGCT  ACTCAGGAGG  CTGAGGCAGG  AGAATCGCTA  GAACCCGGGA      780

GGCGGAGGTT  GCAGTGAGCC  GAGATCGCGC  CATTGCACTC  CAGCCTGGGC  GACAGAGCGA      840

GACTGTCTCA  AAACAAAACA  AAACAAAACA  AAACAAAAAA  CACCGGCTGG  TATGTATGAG      900

AGGATGGGAC  CTTGTGGAAG  AAGAGGTGCC  AGGAATATGT  CTGGGAAGGG  GAGGAGACAG      960

GATTTTGTGG  GAGGGAGAAC  TTAAGAACTG  GATCCATTTG  CGCCATTGAG  AAAGCGCAAG     1020

AGGGAAGTAG  AGGAGCGTCA  GTAGTAACAG  ATGCTGCCGG  CAGGGATGTG  CTTGAGGAGG     1080

ATCCAGAGAT  GAGAGCAGGT  CACTGGGAAA  GGTTAGGGGC  GGGGAGGCCT  TGATTGGTGT     1140

TGGTTTGGTC  GTTGTTGATT  TTGGTTTTAT  GCAAGAAAAA  GAAAACAACC  AGAAACATTG     1200

GAGAAAGCTA  AGGCTACCAC  CACCTACCCG  GTCAGTCACT  CCTCTGTAGC  TTTCTCTTTC     1260

TTGGAGAAAG  GAAAAGACCC  AAGGGGTTGG  CAGCGATATG  TGAAAAAATT  CAGAATTTAT     1320

GTTGTCTAAT  TACAAAAAGC  AACTTCTAGA  ATCTTTAAAA  ATAAGGACG   TTGTCATTAG     1380

TTCTTCTGGT  TTGTATTATT  CTAAAACCTT  CCAAATCTTC  AAATTTACTT  TATTTTAAAA     1440

TGATAAAATG  AAGTTGTCAT  TTTATAAACC  TTTTAAAAAG  ATATATATAT  ATGTTTTCT      1500

AATGTGTTAA  AGTTCATTGG  AACAGAAAGA  AATG                                   1534

( 2 ) INFORMATION FOR SEQ ID NO:14:

( i ) SEQUENCE CHARACTERISTICS:
                 ( A ) LENGTH: 1924 base pairs
                 ( B ) TYPE: nucleic acid
                 ( C ) STRANDEDNESS: double
                 ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                 ( A ) ORGANISM: Homo sapiens ( x i ) SEQUENCE DESCRIPTION: SEQ ID NO:14:

GAGGCTAGAG  GGCAGGCACT  TTATGGCAAA  CTCAGGTAGA  ATTCTTCCTC  TTCCGTCTCT       60

TTCCTTTTAC  GTCATCGGGG  AGACTGGGTG  GCAATCGCAG  CCCGAGAGAC  GCATGGCTCT      120

TTCTGCCCTC  CATCCTCTGA  TGTACCTTGA  TTTCGTATTC  TGAGAGGCTG  CTGCTTAGCG      180

GTAGCCCCTT  GGTTTCCGTG  GCAACGGAAA  AGCGCGGGAA  TTACAGATAA  ATTAAAACTG      240

CGACTGCGCG  GCGTGAGCTC  GCTGAGACTT  CCTGGACCCC  GCACCAGGCT  GTGGGTTTC      300

TCAGATAACT  GGGCCCCTGC  GCTCAGGAGG  CCTTCACCCT  CTGCTCTGGG  TAAAGGTAGT      360

AGAGTCCCGG  GAAAGGGACA  GGGGCCCAA   GTGATGCTCT  GGGTACTGG   CGTGGAGAG      420

TGGATTTCCG  AAGCTGACAG  ATGGGTATTC  TTTGACGGGG  GGTAGGGGCG  GAACCTGAGA      480

GGCGTAAGGC  GTTGTGAACC  CTGGGAGGG   GGGCAGTTTG  TAGGTCGCGA  GGGAAGCGCT      540

GAGGATCAGG  AAGGGGCAC   TGAGTGTCCG  TGGGGAATC   CTCGTGATAG  GAACTGGAAT      600

ATGCCTTGAG  GGGGACACTA  TGTCTTTAAA  AACGTCGGCT  GGTCATGAGG  TCAGGAGTTC      660

CAGACCAGCC  TGACCAACGT  GGTGAAACTC  CGTCTCTACT  AAAAATACNA  AAATTAGCCG      720

GGCGTGGTGC  CGCTCCAGCT  ACTCAGGAGG  CTGAGGCAGG  AGAATCGCTA  GAACCCGGGA      780

GGCGGAGGTT  GCAGTGAGCC  GAGATCGCGC  CATTGCACTC  CAGCCTGGGC  GACAGAGCGA      840
```

```
GACTGTCTCA AAACAAAACA AAACAAAACA AAACAAAAAA CACCGGCTGG TATGTATGAG      900
AGGATGGGAC CTTGTGGAAG AAGAGGTGCC AGGAATATGT CTGGGAAGGG GAGGAGACAG      960
GATTTTGTGG GAGGGAGAAC TTAAGAACTG GATCCATTTG CGCCATTGAG AAAGCGCAAG     1020
AGGGAAGTAG AGGAGCGTCA GTAGTAACAG ATGCTGCCGG CAGGGATGTG CTTGAGGAGG     1080
ATCCAGAGAT GAGAGCAGGT CACTGGGAAA GGTTAGGGGC GGGGAGGCCT TGATTGGTGT     1140
TGGTTTGGTC GTTGTTGATT TTGGTTTTAT GCAAGAAAAA GAAACAACC AGAAACATTG      1200
GAGAAAGCTA AGGCTACCAC CACCTACCCG GTCAGTCACT CCTCTGTAGC TTTCTCTTTC     1260
TTGGAGAAAG GAAAAGACCC AAGGGGTTGG CAGCGATATG TGAAAAAATT CAGAATTTAT     1320
GTTGTCTAAT TACAAAAAGC AACTTCTAGA ATCTTAAAA ATAAAGGACG TTGTCATTAG      1380
TTCTTCTGGT TTGTATTATT CTAAAACCTT CCAAATCTTC AAATTTACTT TATTTTAAAA     1440
TGATAAAATG AAGTTGTCAT TTTATAAACC TTTTAAAAAG ATATATATAT ATGTTTTTCT     1500
AATGTGTTAA AGTTCATTGG AACAGAAAGA AATGGATTTA TCTGCTCTTC GCGTTGAAGA     1560
AGTACAAAAT GTCATTAATG CTATGCAGAA AATCTTAGAG TGTCCATCT GGTAAGTCAG      1620
CACAAGAGTG TATTAATTTG GGATTCCTAT GATTATCTCC TATGCAAATG AACAGAATTG     1680
ACCTTACATA CTAGGGAAGA AAAGACATGT CTAGTAAGAT TAGGCTATTG TAATTGCTGA     1740
TTTTCTTAAC TGAAGAACTT TAAAAATATA GAAATGATT CCTTGTTCTC CATCCACTCT      1800
GCCTCTCCCA CTCCTCTCCT TTTCAACACA ATCCTGTGGT CCGGGAAAGA CAGGGCTCTG     1860
TCTTGATTGG TTCTGCACTG GGCAGGATCT GTTAGATACT GCATTGCTT TCTCCAGCTC      1920
TAAA                                                                 1924
```

( 2 ) INFORMATION FOR SEQ ID NO:15:

( i ) SEQUENCE CHARACTERISTICS:
        ( A ) LENGTH: 631 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:15:

```
AAATGCTGAT GATAGTATAG AGTATTGAAG GGATCAATAT AATTCTGTTT TGATATCTGA       60
AAGCTCACTG AAGGTAAGGA TCGTATTCTC TGCTGTATTC TCAGTTCCTG ACACAGCAGA      120
CATTTAATAA ATATTGAACG AACTTGAGGC CTTATGTTGA CTCAGTCATA ACAGCTCAAA      180
GTTGAACTTA TTCACTAAGA ATAGCTTTAT TTTTAAATAA ATTATTGAGC CTCATTTATT      240
TTCTTTTTCT CCCCCCCCTA CCCTGCTAGT CTGGAGTTGA TCAAGGAACC TGTCTCCACA      300
AAGTGTGACC ACATATTTTG CAAGTAAGTT TGAATGTGTT ATGTGGCTCC ATTATTAGCT      360
TTTGTTTTTG TCCTTCATAA CCCAGGAAAC ACCTAACTTT ATAGAAGCTT TACTTTCTTC      420
AATTAAGTGA GAACGAAAAT CCAACTCCAT TTCATTCTTT CTCAGAGAGT ATATAGTTAT      480
CAAAAGTTGG TTGTAATCAT AGTTCCTGGT AAAGTTTTGA CATATATTAT CTTTTTTTTT      540
TTTGAGACA AGTCTCGCTC TGTCGCCCAG GCTGGAGTGC AGTGGCATGA GGCTTGCTCA       600
CTGCACCTCC GCCCCCGAGT TCAGCGACTC T                                    631
```

( 2 ) INFORMATION FOR SEQ ID NO:16:

( i ) SEQUENCE CHARACTERISTICS:
        ( A ) LENGTH: 481 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:16:

```
TGAGATCTAG ACCACATGGT CAAAGAGATA GAATGTGAGC AATAAATGAA CCTTAAATTT      60
TTCAACAGCT ACTTTTTTTT TTTTTTTTG  AGACAGGGKC TTACTCTGTT GTCCCAGCTG     120
GAGTACAGWG TGCGATCATG AGGCTTACTG TTGCTTGACT CCTAGGCTCA AGCGATCCTA     180
TCACCTCAGT CTCCAAGTAG CTGGACTGTA AGTGCACACC ACCATATCCA GCTAAATTTT     240
GTGTTTTCTG TAGAGACGGG GTTTCGCCAT GTTTCCCAGG CTGGTCTTGA ACTTTGGGCT     300
TAACCCGTCT GCCCACCTAG GCATCCCAAA GTGCTAGGAT TACAGGTGTG AGTCATCATG     360
CCTGGCCAGT ATTTTAGTTA GCTCTGTCTT TTCAAGTCAT ATACAAGTTC ATTTTCTTTT     420
AAGTTTAGTT AACAACCTTA TATCATGTAT TCTTTCTAG  CATAAAGAAA GATTCGAGGC     480
C                                                                     481
```

( 2 ) INFORMATION FOR SEQ ID NO:17:

( i ) SEQUENCE CHARACTERISTICS:
        ( A ) LENGTH: 522 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:17:

```
TGTGATCATA ACAGTAAGCC ATATGCATGT AAGTTCAGTT TTCATAGATC ATTGCTTATG      60
TAGTTTAGGT TTTTGCTTAT GCAGCATCCA AAAACAATTA GGAAACTATT GCTTGTAATT     120
CACCTGCCAT TACTTTTTAA ATGGCTCTTA AGGGCAGTTG TGAGATTATC TTTTCATGGC     180
TATTTGCCTT TTGAGTATTC TTTCTACAAA AGGAAGTAAA TTAAATTGTT CTTTCTTTCT     240
TTATAATTTA TAGATTTTGC ATGCTGAAAC TTCTCAACCA GAAGAAAGGG CCTTCACAGT     300
GTCCTTTATG TAAGAATGAT ATAACCAAAA GGTATATAAT TTGGTAATGA TGCTAGGTTG     360
GAAGCAACCA CAGTAGGAAA AAGTAGAAAT TATTTAATAA CATAGCGTTC CTATAAAACC     420
ATTCATCAGA AAAATTTATA AAAGAGTTTT TAGCACACAG TAAATTATTT CCAAAGTTAT     480
TTTCCTGAAA GTTTATGGG  CATCTGCCTT ATACAGGTAT TG                        522
```

( 2 ) INFORMATION FOR SEQ ID NO:18:

( i ) SEQUENCE CHARACTERISTICS:

( A ) LENGTH: 465 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Homo sapiens ( x i ) SEQUENCE DESCRIPTION: SEQ ID NO:18:

```
GGTAGGCTTA AATGAATGAC AAAAAGTTAC TAAATCACTG CCATCACACG GTTTATACAG      60
ATGTCAATGA TGTATTGATT ATAGAGGTTT TCTACTGTTG CTGCATCTTA TTTTTATTTG     120
TTTACATGTC TTTTCTTATT TTAGTGTCCT TAAAAGGTTG ATAATCACTT GCTGAGTGTG     180
TTTCTCAAAC AATTTAATTT CAGGAGCCTA CAAGAAAGTA CGAGATTTAG TCAACTTGTT     240
GAAGAGCTAT TGAAAATCAT TTGTGCTTTT CAGCTTGACA CAGGTTTGGA GTGTAAGTGT     300
TGAATATCCC AAGAATGACA CTCAAGTGCT GTCCATGAAA ACTCAGGAAG TTTGCACAAT     360
TACTTTCTAT GACGTGGTGA TAAGACCTTT TAGTCTAGGT TAATTTTAGT TCTGTATCTG     420
TAATCTATTT TAAAAAATTA CTCCCACTGG TCTCACACCT TATTT                    465
```

( 2 ) INFORMATION FOR SEQ ID NO:19:

( i ) SEQUENCE CHARACTERISTICS:
( A ) LENGTH: 513 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Homo sapiens ( x i ) SEQUENCE DESCRIPTION: SEQ ID NO:19:

```
AAAAAATCAC AGGTAACCTT AATGCATTGT CTTAACACAA CAAAGAGCAT ACATAGGGTT      60
TCTCTTGGTT TCTTTGATTA TAATTCATAC ATTTTTCTCT AACTGCAAAC ATAATGTTTT     120
CCCTTGTATT TTACAGATGC AAACAGCTAT AATTTGCAA AAAAGGAAAA TAACTCTCCT      180
GAACATCTAA AAGATGAAGT TTCTATCATC CAAAGTATGG GCTACAGAAA CCGTGCCAAA     240
AGACTTCTAC AGAGTGAACC CGAAAATCCT TCCTTGGTAA AACCATTTGT TTTCTTCTTC     300
TTCTTCTTCT TCTTTTCTTT TTTTTTCTT TTTTTTTTG AGATGGAGTC TTGCTCTGTG       360
GCCCAGGCTA GAAGCAGTCC TCCTGCCTTA GCCNCCTTAG TAGCTGGGAT TACAGGCACG     420
CGCACCATGC CAGGCTAATT TTTGTATTTT TAGTAGAGAC GGGGTTTCAT CATGTTGGCC     480
AGGCTGGTCT CGAACTCCTA ACCTCAGGTG ATC                                 513
```

( 2 ) INFORMATION FOR SEQ ID NO:20:

( i ) SEQUENCE CHARACTERISTICS:
( A ) LENGTH: 6769 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:20:

```
ATGATGGAGA TCTTAAAAAG TAATCATTCT GGGGCTGGGC GTAGTAGCTT GCACCTGTAA      60
TCCCAGCACT TCGGGAGGCT GAGGCAGGCA GATAATTTGA GGTCAGGAGT TTGAGACCAG     120
CCTGGCCAAC ATGGTGAAAC CCATCTCTAC TAAAAATACA AAAATTAGCT GGGTGTGGTG     180
GCACGTACCT GTAATCCCAG CTACTCGGGA GGCGGAGGCA CAAGAATTGC TTGAACCTAG     240
GACGCGGAGG TTGCAGCGAG CCAAGATCGC GCCACTGCAC TCCAGCCTGG GCCGTAGAGT     300
GAGACTCTGT CTCAAAAAAG AAAAAAAAGT AATTGTTCTA GCTGGGCGCA GTGGCTCTTG     360
CCTGTAATCC CAGCACTTTG GGAGGCCAAG GCGGGTGGAT CTCGAGTCCT AGAGTTCAAG     420
ACCAGCCTAG GCAATGTGGT GAAACCCCAT CGCTACAAAA AATACAAAAA TTAGCCAGGC     480
ATGGTGGCGT GCGCATGTAG TCCCAGCTCC TTGGGAGGCT GAGGTGGGAG GATCACTTGA     540
ACCCAGGAGA CAGAGGTTGC AGTGAACCGA GATCACGCCA CCACGCTCCA GCCTGGGCAA     600
CAGAACAAGA CTCTGTCTAA AAAATACAA ATAAATAAA AGTAGTTCTC ACAGTACCAG      660
CATTCATTTT TCAAAGATA TAGAGCTAAA AAGGAAGGAA AAAAAAGTA ATGTTGGGCT      720
TTTAAATACT CGTTCCTATA CTAAATGTTC TTAGGAGTGC TGGGGTTTTA TTGTCATCAT     780
TTATCCTTTT TAAAAATGTT ATTGGCCAGG CACGGTGGCT CATGGCTGTA ATCCCAGCAC     840
TTTGGGAGGC CGAGGCAGGC AGATCACCTG AGGTCAGGAG TGTGAGACCA GCCTGGCCAA     900
CATGGCGAAA CCTGTCTCTA CTAAAATAC AAAAATTAAC TAGGCGTGGT GGTGTACGCC      960
TGTAGTCCCA GCTACTCGGG AGGCTGAGGC AGGAGAATCA ACTGAACCAG GGAGGTGGAG    1020
GTTGCAGTGT GCCGAGATCA CGCCACTGCA CTCTAGCCTG GCAACAGAGC AAGATTCTGT    1080
CTCAAAAAAA AAAAACATAT ATACACATAT ATCCCAAAGT GCTGGGATTA CATATATATA    1140
TATATATATA TATTATATAT ATATATATAT ATATATGTGA TATATATGTG ATATATATAT    1200
AACATATATA TATGTAATAT ATATGTGATA TATATATAAT ATATATATGT AATATATATG    1260
TGATATATAT ATATACACAC ACACACACAT ATATATGTAT GTGTGTGTAC ACACACACAC    1320
ACAAATTAGC CAGGCATAGT TGCACACGCT TGGTAGACCC AGCTACTCAG GAGGCTGAGG    1380
GAGGAGAATC TCTTGAACTT AGGAGGCGGA GGTTGCAGTG AGCTGAGATT GCGCCACTGC    1440
ACTCCAGCCT GGGTGACAGA GCAGGACTCT GTACACCCCC CAAAACAAAA AAAAAAGTTA    1500
TCAGATGTGA TTGGAATGTA TATCAAGTAT CAGCTTCAAA ATATGCTATA TTAATACTTC    1560
AAAAATTACA CAAATAATAC ATAATCAGGT TTGAAAAATT TAAGACAACM SAARAAAAA     1620
W Y CMAATCAC AMATATCCCA CACATTTTAT TATTMCTMCT MCWATTATTT TGWAGAGMCT    1680
GGGTCTCAC Y  C Y KTTGCTWA TGCTG-
GTCTT TGAAC Y CC Y K GCC Y CAARCA RTCCTSCTCC  1740
ABCCTCCCAA RGTGCTGGGG ATWATAGGCA TGARCTAACC GCACCCAGCC CCAGACATTT    1800
TAGTGTGTAA ATTCCTGGGC ATTTTTTCAA GGCATCATAC ATGTTAGCTG ACTGATGATG    1860
GTCAATTTAT TTTGTCCATG GTGTCAAGTT TCTCTTCAGG AGGAAAAGCA CAGAACTGGC    1920
CAACAATTGC TTGACTGTTC TTTACCATAC TGTTTAGCAG GAAACCAGTC TCAGTGTCCA    1980
ACTCTCTAAC CTTGGAACTG TGAGAACTCT GAGGACAAAG CAGCGGATAC AACCTCAAAA    2040
GACGTCTGTC TACATTGAAT TGGGTAAGGG TCTCAGGTTT TTAAGTATT TAATAATAAT    2100
```

```
TGCTGGATTC CTTATCTTAT AGTTTTGCCA AAAATCTTGG TCATAATTTG TATTTGTGGT     2160
AGGCAGCTTT GGGAAGTGAA TTTTATGAGC CCTATGGTGA GTTATAAAAA ATGTAAAAGA     2220
CGCAGTTCCC ACCTTGAAGA ATCTTACTTT AAAAGGGAG CAAAAGAGGC CAGGCATGGT      2280
GGCTCACACC TGTAATCCCA GCACTTTGGG AGGCCAAAGT GGGTGGATCA CCTGAGGTCG     2340
GGAGTTCGAG ACCAGCCTAG CCAACATGGA GAAACTCTGT CTGTACCAAA AATAAAAAA     2400
TTAGCCAGGT GTGGTGGCAC ATAACTGTAA TCCCAGCTAC TCGGGAGGCT GAGGCAGGAG     2460
AATCACTTGA ACCCGGGAGG TGGAGGTTGC GGTGAACCGA GATCGCACCA TTGCACTCCA     2520
GCCTGGGCAA AAATAGCGAA ACTCCATCTA AAAAAAAAA AGAGAGCAAA AGAAAGAMTM     2580
TCTGGTTTTA AMTMTGTGTA AATATGTTTT TGGAAAGATG GAGAGTAGCA ATAAGAAAAA     2640
ACATGATGGA TTGCTACAGT ATTTAGTTCC AAGATAAATT GTACTAGATG AGGAAGCCTT     2700
TTAAGAAGAG CTGAATTGCC AGGCGCAGTG GCTCACGCCT GTAATCCCAG CACTTTGGGA     2760
GGCCGAGGTG GGCGGATCAC CTGAGGTCGG GAGTTCAAGA CCAGCCTGAC CAACATGGAG     2820
AAACCCCATC TCTACTAAAA AAAAAAAAA AAAATTAGC CGGGGTGGTG GCTTATGCCT       2880
GTAATCCCAG CTACTCAGGA GGCTGAGGCA GGAGAATCGC TTGAACCCAG GAAGCAGAGG     2940
TTGCAGTGAG CCAAGATCGC ACCATTGCAC TCCAGCCTAG GCAACAAGAG TGAAACTCCA     3000
TCTCAAAAAA AAAAAAAAG AGCTGAATCT GGCTGGGCA GGATGGCTCG TGCCTGTAAT       3060
CCTAACGCTT TGGAAGACCG AGGCAGAAGG ATTGGTTGAG TCCACGAGTT TAAGACCAGC     3120
CTGGCCAACA TAGGGGAACC CTGTCTCTAT TTTTAAAATA ATAATACATT TTTGGCCGGT     3180
GCGGTGGCTC ATGCCTGTAA TCCCAATACT TTGGGAGGCT GAGGCAGGTA GATCACCTGA     3240
GGTCAGAGTT CGAGACCAGC CTGGATAACC TGGTGAAACC CCTCTTTACT AAAAATACAA     3300
AAAAAAAAA AAATTAGCTG GGTGTGGTAG CACATGCTTG TAATCCCAGC TACTTGGGAG      3360
GCTGAGGCAG GAGAATCGCT TGAACCAGGG AGGCGGAGGT TACAATGAGC CAACACTACA     3420
CCACTGCACT CCAGCCTGGG CAATAGAGTG AGACTGCATC TCAAAAAAT AATAATTTTT      3480
AAAAATAATA AATTTTTTA AGCTTATAAA AAGAAAGTT GAGGCCAGCA TAGTAGCTCA       3540
CATCTGTAAT CTCAGCAGTG GCAGAGGATT GCTTGAAGCC AGGAGTTTGA GACCAGCCTG     3600
GGCAACATAG CAAGACCTCA TCTCTACAAA AAAATTTCTT TTTAAATTA GCTGGGTGTG      3660
GTGGTGTGCA TCTGTAGTCC CAGCTACTCA GGAGGCAGAG GTGAGTGGAT ACATTGAACC     3720
CAGGAGTTTG AGGCTGTAGT GAGCTATGAT CATGCCACTG CACTCCAACC TGGGTGACAG     3780
AGCAAGACCT CCAAAAAAAA AAAAAAAGA GCTGCTGAGC TCAGAATTCA AACTGGGCTC      3840
TCAAATTGGA TTTTCTTTTA GAATATATTT ATAATTAAAA AGGATAGCCA TCTTTTGAGC     3900
TCCCAGGCAC CACCATCTAT TTATCATAAC ACTTACTGTT TTCCCCCTT ATGATCATAA      3960
ATTCCTAGAC AACAGGCATT GTAAAAATAG TTATAGTAGT TGATATTTAG GAGCACTTAA     4020
CTATATTCCA GGCACTATTG TGCTTTTCTT GTATAACTCA TTAGATGCTT GTCAGACCTC     4080
TGAGATTGTT CCTATTATAC TTATTTTACA GATGAGAAAA TTAAGGCACA GAGAAGTTAT     4140
GAAATTTTTC CAAGGTATTA AACCTAGTAA GTGGCTGAGC CATGATTCAA ACCTAGGAAG     4200
TTAGATGTCA GAGCCTGTGC TTTTTTTTG TTTTGTTTT TGTTTCAGT AGAAACGGGG        4260
GTCTCACTTT GTTGGCCAGG CTGGTCTTGA ACTCCTAACC TCAAATAATC CACCCATCTC     4320
GGCCTCCTCA AGTGCTGGGA TTACAGGTGA GAGCCACTGT GCCTGGCGAA GCCCATGCCT     4380
TTAACCACTT CTCTGTATTA CATACTAGCT AACTAGCAT TGTACCTGCC ACAGTAGATG      4440
CTCAGTAAAT ATTTCTAGTT GAATATCTGT TTTTCAACAA GTACATTTTT TTAACCCTTT     4500
```

```
TAATTAAGAA AACTTTTATT GATTTATTTT TTGGGGGGAA ATTTTTTAGG ATCTGATTCT      4560
TCTGAAGATA CCGTTAATAA GGCAACTTAT GCAGGTGAG TCAAAGAGAA CCTTTGTCTA       4620
TGAAGCTGGT ATTTTCCTAT TTAGTTAATA TTAAGGATTG ATGTTTCTCT CTTTTTAAAA      4680
ATATTTTAAC TTTTATTTTA GGTTCAGGGA TGTATGTGCA GTTTGTTATA TAGGTAAACA      4740
CACGACTTGG GATTGGTGT ATAGATTTTT TTCATCATCC GGGTACTAAG CATACCCCAC       4800
AGTTTTTTGT TTGCTTTCTT TCTGAATTTC TCCCTCTTCC CACCTTCCTC CCTCAAGTAG      4860
GCTGGTGTTT CTCCAGACTA GAATCATGGT ATTGGAAGAA ACCTTAGAGA TCATCTAGTT      4920
TAGTTCTCTC ATTTTATAGT GGAGGAAATA CCCTTTTTGT TTGTTGGATT TAGTTATTAG      4980
CACTGTCCAA AGGAATTTAG GATAACAGTA GAACTCTGCA CATGCTTGCT TCTAGCAGAT      5040
TGTTCTCTAA GTTCCTCATA TACAGTAATA TTGACACAGC AGTAATTGTG ACTGATGAAA      5100
ATGTTCAAGG ACTTCATTTT CAACTCTTTC TTTCCTCTGT TCCTTATTTC CACATATCTC      5160
TCAAGCTTTG TCTGTATGTT ATATAATAAA CTACAAGCAA CCCCAACTAT GTTACCTACC      5220
TTCCTTAGGA ATTATTGCTT GACCCAGGTT TTTTTTTTT TTTTTTGGA GACGGGTCT         5280
TGCCCTGTTG CCAGGATGGA GTGTAGTGGC GCCATCTCGG CTCACTGCAA TCTCCAACTC      5340
CCTGGTTCAA GCGATTCTCC TGTCTCAATC TCACGAGTAG CTGGGACTAC AGGTATACAC      5400
CACCACGCCC GGTTAATTGA CCATTCCATT TCTTTCTTTC TCTCTTTTTT TTTTTTTTT       5460
TTGAGACAGA GTCTTGCTCT GTTGCCCAGG CTGGAGTACA GAGGTGTGAT CTCACCTCTC      5520
CGCAACGTCT GCCTCCCAGG TTGAAGCCAT ACTCCTGCCT CAGCCTCTCT AGTAGCTGGG      5580
ACTACAGGCG CGCGCCACCA CACCCGGCTA ATTTTGTAT TTTTAGTAGA GATGGGGTTT       5640
CACCATGTTG GCCAGGCTGG TCTTGAACTC ATGACCTCAA GTGGTCCACC CGCCTCAGCC      5700
TCCCAAAGTG CTGGAATTAC AGGCTTGAGC CACCGTGCCC AGCAACCATT TCATTTCAAC      5760
TAGAAGTTTC TAAAGGAGAG AGCAGCTTTC ACTAACTAAA TAAGATTGGT CAGCTTTCTG      5820
TAATCGAAAG AGCTAAAATG TTTGATCTTG GTCATTTGAC AGTTCTGCAT ACATGTAACT      5880
AGTGTTTCTT ATTAGGACTC TGTCTTTTCC CTATAGTGTG GGAGATCAAG AATTGTTACA      5940
AATCACCCCT CAAGGAACCA GGGATGAAAT CAGTTTGGAT TCTGCAAAAA AGGGTAATGG      6000
CAAAGTTTGC CAACTTAACA GGCACTGAAA AGAGAGTGGG TAGATACAGT ACTGTAATTA      6060
GATTATTCTG AAGACCATTT GGGACCTTTA CAACCCACAA AATCTCTTGG CAGAGTTAGA      6120
GTATCATTCT CTGTCAAATG TCGTGGTATG GTCTGATAGA TTTAAATGGT ACTAGACTAA      6180
TGTACCTATA ATAAGACCTT CTTGTAACTG ATTGTTGCCC TTTCGCTTTT TTTTTGTTT      6240
GTTTGTTTGT TTTTTTTTGA GATGGGGTCT CACTCTGTTG CCCAGGCTGG AGTGCAGTGA      6300
TGCAATCTTG GCTCACTGCA ACCTCCACCT CCAAAGGCTC AAGCTATCCT CCCACTTCAG      6360
CCTCCTGAGT AGCTGGGACT ACAGGCGCAT GCCACCACAC CCGGTTAATT TTTGTGGTT      6420
TTATAGAGAT GGGGTTTCAC CATGTTACCG AGGCTGGTCT CAAACTCCTG GACTCAAGCA      6480
GTCTGCCCAC TTCAGCCTCC CAAAGTGCTG CAGTTACAGG CTTGAGCCAC TGTGCCTGGC      6540
CTGCCCTTTA CTTTTAATTG GTGTATTTGT GTTTCATCTT TTACCTACTG GTTTTAAAT      6600
ATAGGGAGTG GTAAGTCTGT AGATAGAACA GAGTATTAAG TAGACTTAAT GGCCAGTAAT      6660
CTTTAGAGTA CATCAGAACC AGTTTTCTGA TGGCCAATCT GCTTTTAATT CACTCTTAGA      6720
CGTTAGAGAA ATAGGTGTGG TTTCTGCATA GGGAAAATTC TGAAATTAA                  6769
```

( 2 ) INFORMATION FOR SEQ ID NO:21:

(i) SEQUENCE CHARACTERISTICS:
    (A) LENGTH: 4249 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:21:

```
GATCCTAAGT GGAAATAATC TAGGTAAATA GGAATTAAAT GAAAGAGTAT GAGCTACATC    60
TTCAGTATAC TTGGTAGTTT ATGAGGTTAG TTTCTCTAAT ATAGCCAGTT GGTTGATTTC   120
CACCTCCAAG GTGTATGAAG TATGTATTTT TTTAATGACA ATTCAGTTTT TGAGTACCTT   180
GTTATTTTTG TATATTTTCA GCTGCTTGTG AATTTCTGA  GACGGATGTA ACAAATACTG   240
AACATCATCA ACCCAGTAAT AATGATTTGA ACACCACTGA GAAGCGTGCA GCTGAGAGGC   300
ATCCAGAAAA GTATCAGGGT AGTTCTGTTT CAAACTTGCA TGTGGAGCCA TGTGGCACAA   360
ATACTCATGC CAGCTCATTA CAGCATGAGA ACAGCAGTTT ATTACTCACT AAAGACAGAA   420
TGAATGTAGA AAAGGCTGAA TTCTGTAATA AAGCAAACA  GCCTGGCTTA GCAAGGAGCC   480
AACATAACAG ATGGGCTGGA AGTAAGGAAA CATGTAATGA TAGGCGGACT CCCAGCACAG   540
AAAAAAAGGT AGATCTGAAT GCTGATCCCC TGTGTGAGAG AAAAGAATGG AATAAGCAGA   600
AACTGCCATG CTCAGAGAAT CCTAGAGATA CTGAAGATGT TCCTTGGATA ACACTAAATA   660
GCAGCATTCA GAAAGTTAAT GAGTGGTTTT CCAGAAGTGA TGAACTGTTA GGTTCTGATG   720
ACTCACATGA TGGGGAGTCT GAATCAAATG CCAAAGTAGC TGATGTATTG GACGTTCTAA   780
ATGAGGTAGA TGAATATTCT GGTTCTTCAG AGAAATAGA  CTTACTGGCC AGTGATCCTC   840
ATGAGGCTTT AATATGTAAA AGTGAAAGAG TTCACTCCAA ATCAGTAGAG AGTAATATTG   900
AAGGCCAAAT ATTTGGGAAA ACCTATCGGA AGAAGGCAAG CCTCCCCAAC TTAAGCCATG   960
TAACTGAAAA TCTAATTATA GGAGCATTTG TTACTGAGCC ACAGATAATA CAAGAGCGTC  1020
CCCTCACAAA TAAATTAAAG CGTAAAAGGA GACCTACATC AGGCCTTCAT CCTGAGGATT  1080
TTATCAAGAA AGCAGATTTG GCAGTTCAAA AGACTCCTGA AATGATAAAT CAGGGAACTA  1140
ACCAAACGGA GCAGAATGGT CAAGTGATGA ATATTACTAA TAGTGGTCAT GAGAATAAAA  1200
CAAAAGGTGA TTCTATTCAG AATGAGAAAA ATCCTAACCC AATAGAATCA CTCGAAAAAG  1260
AATCTGCTTT CAAAACGAAA GCTGAACCTA TAAGCAGCAG TATAAGCAAT ATGGAACTCG  1320
AATTAAATAT CCACAATTCA AAAGCACCTA AAAAGAATAG GCTGAGGAGG AAGTCTTCTA  1380
CCAGGCATAT TCATGCGCTT GAACTAGTAG TCAGTAGAAA TCTAAGCCCA CCTAATTGTA  1440
CTGAATTGCA AATTGATAGT TGTTCTAGCA GTGAAGAGAT AAAGAAAAAA AAGTACAACC  1500
AAATGCCAGT CAGGCACAGC AGAAACCTAC AACTCATGGA AGGTAAAGAA CCTGCAACTG  1560
GAGCCAAGAA GAGTAACAAG CCAAATGAAC AGACAAGTAA AAGACATGAC AGCGATACTT  1620
TCCCAGAGCT GAAGTTAACA AATGCACCTG GTTCTTTTAC TAAGTGTTCA ATACCAGTG   1680
AACTTAAAGA ATTTGTCAAT CCTAGCCTTC CAAGAGAAGA AAAAGAAGAG AACTAGAAAC  1740
AGTTAAAGTG TCTAATAATG CTGAAGACCC CAAAGATCTC ATGTTAAGTG GAGAAAGGGT  1800
TTTGCAAACT GAAAGATCTG TAGAGAGTAG CAGTATTTCA TTGGTACCTG GTACTGATTA  1860
TGGCACTCAG GAAAGTATCT CGTTACTGGA AGTTAGCACT CTAGGGAAGG CAAAAACAGA  1920
```

| | | | | | |
|---|---|---|---|---|---|
| ACCAAATAAA | TGTGTGAGTC | AGTGTGCAGC | ATTTGAAAAC | CCCAAGGGAC | TAATTCATGG | 1980 |
| TTGTTCCAAA | GATAATAGAA | ATGACACAGA | AGGCTTTAAG | TATCCATTGG | GACATGAAGT | 2040 |
| TAACCACAGT | CGGGAAACAA | GCATAGAAAT | GGAAGAAAGT | GAACTTGATG | CTCAGTATTT | 2100 |
| GCAGAATACA | TTCAAGGTTT | CAAAGCGCCA | GTCATTTGCT | CCGTTTTCAA | ATCCAGGAAA | 2160 |
| TGCAGAAGAG | GAATGTGCAA | CATTCTCTGC | CCACTCTGGG | TCCTTAAAGA | AACAAAGTCC | 2220 |
| AAAAGTCACT | TTTGAATGTG | AACAAAAGGA | AGAAAATCAA | GGAAAGAATG | AGTCTAATAT | 2280 |
| CAAGCCTGTA | CAGACAGTTA | ATATCACTGC | AGGCTTTCCT | GTGGTTGGTC | AGAAAGATAA | 2340 |
| GCCAGTTGAT | AATGCCAAAT | GTAGTATCAA | AGGAGGCTCT | AGGTTTTGTC | TATCATCTCA | 2400 |
| GTTCAGAGGC | AACGAAACTG | GACTCATTAC | TCCAAATAAA | CATGGACTTT | TACAAAACCC | 2460 |
| ATATCGTATA | CCACCACTTT | TTCCCATCAA | GTCATTTGTT | AAAACTAAAT | GTAAGAAAAA | 2520 |
| TCTGCTAGAG | GAAAACTTTG | AGGAACATTC | AATGTCACCT | GAAAGAGAAA | TGGGAAATGA | 2580 |
| GAACATTCCA | AGTACAGTGA | GCACAATTAG | CCGTAATAAC | ATTAGAGAAA | ATGTTTTTAA | 2640 |
| AGAAGCCAGC | TCAAGCAATA | TTAATGAAGT | AGGTTCCAGT | ACTAATGAAG | TGGGCTCCAG | 2700 |
| TATTAATGAA | ATAGGTTCCA | GTGATGAAAA | CATTCAAGCA | GAACTAGGTA | GAAACAGAGG | 2760 |
| GCCAAAATTG | AATGCTATGC | TTAGATTAGG | GGTTTGCAA | CCTGAGGTCT | ATAAACAAAG | 2820 |
| TCTTCCTGGA | AGTAATTGTA | AGCATCCTGA | AATAAAAAAG | CAAGAATATG | AAGAAGTAGT | 2880 |
| TCAGACTGTT | AATACAGATT | TCTCTCCATA | TCTGATTTCA | GATAACTTAG | AACAGCCTAT | 2940 |
| GGGAAGTAGT | CATGCATCTC | AGGTTTGTTC | TGAGACACCT | GATGACCTGT | TAGATGATGG | 3000 |
| TGAAATAAAG | GAAGATACTA | GTTTTGCTGA | AAATGACATT | AAGGAAAGTT | CTGCTGTTTT | 3060 |
| TAGCAAAAGC | GTCCAGAAAG | GAGAGCTTAG | CAGGAGTCCT | AGCCCTTTCA | CCCATACACA | 3120 |
| TTTGGCTCAG | GGTTACCGAA | GAGGGGCCAA | GAAATTAGAG | TCCTCAGAAG | AGAACTTATC | 3180 |
| TAGTGAGGAT | GAAGAGCTTC | CCTGCTTCCA | ACACTTGTTA | TTTGGTAAAG | TAAACAATAT | 3240 |
| ACCTTCTCAG | TCTACTAGGC | ATAGCACCGT | TGCTACCGAG | TGTCTGTCTA | AGAACACAGA | 3300 |
| GGAGAATTTA | TTATCATTGA | AGAATAGCTT | AAATGACTGC | AGTAACCAGG | TAATATTGGC | 3360 |
| AAAGGCATCT | CAGGAACATC | ACCTTAGTGA | GGAAACAAAA | TGTTCTGCTA | GCTTGTTTTC | 3420 |
| TTCACAGTGC | AGTGAATTGG | AAGACTTGAC | TGCAAATACA | AACACCCAGG | ATCCTTTCTT | 3480 |
| GATTGGTTCT | TCCAAACAAA | TGAGGCATCA | GTCTGAAAGC | CAGGGAGTTG | GTCTGAGTGA | 3540 |
| CAAGGAATTG | GTTTCAGATG | ATGAAGAAAG | AGGAACGGGC | TTGGAAGAAA | ATAATCAAGA | 3600 |
| AGAGCAAAGC | ATGGATTCAA | ACTTAGGTAT | GGAACCAGG | TTTTGTGTT | TGCCCCAGTC | 3660 |
| TATTTATAGA | AGTGAGCTAA | ATGTTTATGC | TTTTGGGAG | CACATTTTAC | AAATTTCCAA | 3720 |
| GTATAGTTAA | AGGAACTGCT | TCTTAAACTT | GAAACATGTT | CCTCCTAAGG | TGCTTTTCAT | 3780 |
| AGAAAAAAGT | CCTTCACACA | GCTAGGACGT | CATCTTTGAC | TGAATGAGCT | TTAACATCCT | 3840 |
| AATTACTGGT | GGACTTACTT | CTGGTTTCAT | TTTATAAAGC | AAATCCCGGT | GTCCCAAAGC | 3900 |
| AAGGAATTTA | ATCATTTTGT | GTGACATGAA | AGTAAATCCA | GTCCTGCCAA | TGAGAAGAAA | 3960 |
| AAGACACAGC | AAGTTGCAGC | GTTTATAGTC | TGCTTTTACA | TCTGAACCTC | TGTTTTTGTT | 4020 |
| ATTTAAGGTG | AAGCAGCATC | TGGGTGTGAG | AGTGAAACAA | GCGTCTCTGA | AGACTGCTCA | 4080 |
| GGGCTATCCT | CTCAGAGTGA | CATTTTAACC | ACTCAGGTAA | AAAGCGTGTG | TGTGTGTGCA | 4140 |
| CATGCGTGTG | TGTGGTGTCC | TTTGCATTCA | GTAGTATGTA | TCCCACATTC | TTAGGTTTGC | 4200 |
| TGACATCATC | TCTTTGAATT | AATGGCACAA | TTGTTTGTGG | TTCATTGTC | | 4249 |

( 2 ) INFORMATION FOR SEQ ID NO:22:

( i ) SEQUENCE CHARACTERISTICS:
        ( A ) LENGTH: 710 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:22:

```
NGNGAATGTA ATCCTAATAT TTCNCNCCNA CTTAAAAGAA TACCACTCCA ANGGCATCNC    60
AATACATCAA TCAATTGGGG AATTGGGATT TTCCCTCNCT AACATCANTG GAATAATTTC   120
ATGGCATTAA TTGCATGAAT GTGGTTAGAT TAAAAGGTGT TCATGCTAGA ACTTGTAGTT   180
CCATACTAGG TGATTTCAAT TCCTGTGCTA AAATTAATTT GTATGATATA TTNTCATTTA   240
ATGGAAAGCT TCTCAAAGTA TTTCATTTTC TTGGTACCAT TTATCGTTTT TGAAGCAGAG   300
GGATACCATG CAACATAACC TGATAAAGCT CCAGCAGGAA ATGGCTGAAC TAGAAGCTGT   360
GTTAGAACAG CATGGGAGCC AGCCTTCTAA CAGCTACCCT TCCATCATAA GTGACTCTTC   420
TGCCCTTGAG GACCTGCGAA ATCCAGAACA AGCACATCA GAAAAGGTG TGTATTGTTG     480
GCCAAACACT GATATCTTAA GCAAATTCT TTCCTTCCCC TTTATCTCCT TCTGAAGAGT    540
AAGGACCTAG CTCCAACATT TTATGATCCT TGCTCAGCAC ATGGGTAATT ATGGAGCCTT   600
GGTTCTTGTC CCTGCTCACA ACTAATATAC CAGTCAGAGG GACCCAAGGC AGTCATTCAT   660
GTTGTCATCT GAGATACCTA CAACAAGTAG ATGCTATGGG GAGCCCATGG              710
```

( 2 ) INFORMATION FOR SEQ ID NO:23:

( i ) SEQUENCE CHARACTERISTICS:
        ( A ) LENGTH: 473 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:23:

```
CCATTGGTGC TAGCATCTGT CTGTTGCATT GCTTGTGTTT ATAAAATTCT GCCTGATATA    60
CTTGTTAAAA ACCAATTTGT GTATCATAGA TTGATGCTTT TGAAAAAAAT CAGTATTCTA   120
ACCTGAATTA TCACTATCAG AACAAAGCAG TAAAGTAGAT TTGTTTCTC ATTCCATTTA    180
AAGCAGTATT AACTTCACAG AAAAGTAGTG AATACCCTAT AAGCCAGAAT CCAGAAGGCC   240
TTTCTGCTGA CAAGTTTGAG GTGTCTGCAG ATAGTTCTAC CAGTAAAAAT AAAGAACCAG   300
GAGTGGAAAG GTAAGAAACA TCAATGTAAA GATGCTGTGG TATCTGACAT CTTTATTTAT   360
ATTGAACTCT GATTGTTAAT TTTTTCACC ATACTTTCTC CAGTTTTTTT GCATACAGGC    420
ATTTATACAC TTTTATTGCT CTAGGATACT TCTTTTGTTT AATCCTATAT AGG          473
```

(2) INFORMATION FOR SEQ ID NO:24:

(i) SEQUENCE CHARACTERISTICS:
        (A) LENGTH: 421 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:24:

```
GGATAAGNTC AAGAGATATT TTGATAGGTG ATGCAGTGAT NAATTGNGAA AATTTNCTGC    60
CTGCTTTTAA TCTTCCCCCG TTCTTTCTTC CTNCCTCCCT CCCTTCCTNC CTCCCGTCCT   120
TNCCTTTCCT TTCCCTCCCT TCCNCCTTCT TTCCNTCTNT CTTTCCTTTC TTTCCTGTCT   180
ACCTTTCTTT CCTTCCTCCC TTCCTTTTCT TTTCTTTCTT TCCTTTCCTT TTCTTTCCTT   240
TCTTTCCTTT CCTTTCTTTC TTGACAGAGT CTTGCTCTGT CACTCAGGCT GGAGTGCAGT   300
GGCGTGATCT CGNCTCACTG CAACCTCTGT CTCCCAGGTT CAAGCAATTT TCCTGCCTCA   360
GCCTCCCGAG TAGCTGAGAT TACAGGCGCC AGCCACCACA CCCAGCTACT GACCTGCTTT   420
T                                                                  421
```

(2) INFORMATION FOR SEQ ID NO:25:

(i) SEQUENCE CHARACTERISTICS:
        (A) LENGTH: 997 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:25:

```
AAACAGCTGG GAGATATGGT GCCTCAGACC AACCCCATGT TATATGTCAA CCCTGACATA    60
TTGGCAGGCA ACATGAATCC AGACTTCTAG GCTGTCATGC GGGCTCTTTT TTGCCAGTCA   120
TTTCTGATCT CTCTGACATG AGCTGTTTCA TTTATGCTTT GGCTGCCCAG CAAGTATGAT   180
TTGTCCTTTC ACAATTGGTG GCGATGGTTT TCTCCTTCCA TTTATCTTTC TAGGTCATCC   240
CCTTCTAAAT GCCCATCATT AGATGATAGG TGGTACATGC ACAGTTGCTC TGGGAGTCTT   300
CAGAATAGAA ACTACCCATC TCAAGAGGAG CTCATTAAGG TTGTTGATGT GGAGGAGCAA   360
CAGCTGGAAG AGTCTGGGCC ACACGATTTG ACGGAAACAT CTTACTTGCC AAGGCAAGAT   420
CTAGGTAATA TTTCATCTGC TGTATTGGAA CAAACACT YT GATTTACTC TGAATCCTAC   480
ATAAAGATAT TCTGGTTAAC CAACTTTTAG ATGTACTAGT CTATCATGGA CACTTTTGTT   540
ATACTTAATT AAGCCCACTT TAGAAAAATA GCTCAAGTGT TAATCAAGGT TTACTTGAAA   600
ATTATTGAAA CTGTTAATCC ATCTATATTT TAATTAATGG TTTAACTAAT GATTTGAGG    660
ATGWGGGAGT CKTGGTGTAC TCTAMATGTA TTATTTCAGG CCAGGCATAG TGGCTCACGC   720
CTGGTAATCC CAGTA Y YCMR GAGCCCGAGG CAGGTGGAGC CAGCTGAGGT CAGGAGTTCA   780
```

| | | | | | |
|---|---|---|---|---|---|
| AGACCTGTCT | TGGCCAACAT | GGGNGAAACC | CTGTCTTCTT | CTTAAAAAAN | ACAAAAAAA | 840 |
| TTAACTGGGT | TGTGCTTAGG | TGNATGCCCC | GNATCCTAGT | TNTTCTTGNG | GGTTGAGGGA | 900 |
| GGAGATCACN | TTGGACCCCG | GAGGGGNGGG | TGGGGGNGAG | CAGGNCAAAA | CACNGACCCA | 960 |
| GCTGGGGTGG | AAGGGAAGCC | CACTCNAAAA | AANNTTN | | | 997 |

(2) INFORMATION FOR SEQ ID NO:26:

(i) SEQUENCE CHARACTERISTICS:
        (A) LENGTH: 639 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:26:

| | | | | | |
|---|---|---|---|---|---|
| TTTTTAGGAA | ACAAGCTACT | TTGGATTTCC | ACCAACACCT | GTATTCATGT | ACCCATTTTT | 60 |
| CTCTTAACCT | AACTTTATTG | GTCTTTTTAA | TTCTTAACAG | AGACCAGAAC | TTTGTAATTC | 120 |
| AACATTCATC | GTTGTGTAAA | TTAAACTTCT | CCCATTCCTT | TCAGAGGGAA | CCCCTTACCT | 180 |
| GGAATCTGGA | ATCAGCCTCT | TCTCTGATGA | CCCTGAATCT | GATCCTTCTG | AAGACAGAGC | 240 |
| CCCAGAGTCA | GCTCGTGTTG | GCAACATACC | ATCTTCAACC | TCTGCATTGA | AAGTTCCCCA | 300 |
| ATTGAAAGTT | GCAGAATCTG | CCCAGAGTCC | AGCTGCTGCT | CATACTACTG | ATACTGCTGG | 360 |
| GTATAATGCA | ATGGAAGAAA | GTGTGAGCAG | GGAGAAGCCA | GAATTGACAG | CTTCAACAGA | 420 |
| AAGGGTCAAC | AAAAGAATGT | CCATGGTGGT | GTCTGGCCTG | ACCCAGAAG | AATTTGTGAG | 480 |
| TGTATCCATA | TGTATCTCCC | TAATGACTAA | GACTTAACAA | CATTCTGGAA | AGAGTTTTAT | 540 |
| GTAGGTATTG | TCAATTAATA | ACCTAGAGGA | AGAAATCTAG | AAAACAATCA | CAGTTCTGTG | 600 |
| TAATTTAATT | TCGATTACTA | ATTTCTGAAA | ATTAGAA Y | | | 639 |

(2) INFORMATION FOR SEQ ID NO:27:

(i) SEQUENCE CHARACTERISTICS:
        (A) LENGTH: 922 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:27:

| | | | | | |
|---|---|---|---|---|---|
| NCCCNNCCCC | CNAATCTGAA | ATGGGGGTAA | CCCCCCCCCA | ACCGANACNT | GGGTNGCNTA | 60 |
| GAGANTTTAA | TGGCCCNTTC | TGAGGNACAN | AAGCTTAAGC | CAGGNGACGT | GGANCNATGN | 120 |
| GTTGTTTNTT | GTTTGGTTAC | CTCCAGCCTG | GGTGACAGAG | CAAGACTCTG | TCTAAAAAAA | 180 |
| AAAAAAAAA | AAATCGACTT | TAAATAGTTC | CAGGACACGT | GTAGAACGTG | CAGGATTGCT | 240 |
| ACGTAGGTAA | ACATATGCCA | TGGTGGGATA | ACTAGTATTC | TGAGCTGTGT | GCTAGAGGTA | 300 |

| ACTCATGATA | ATGGAATATT | TGATTTAATT | TCAGATGCTC | GTGTACAAGT | TTGCCAGAAA | 360 |
| ACACCACATC | ACTTTAACTA | ATCTAATTAC | TGAAGAGACT | ACTCATGTTG | TTATGAAAAC | 420 |
| AGGTATACCA | AGAACCTTTA | CAGAATACCT | TGCATCTGCT | GCATAAAACC | ACATGAGGCG | 480 |
| AGGCACGGTG | GCGCATGCCT | GTAATCGCAG | CACTTTGGGA | GGCCGAGGCG | GCAGATCAC | 540 |
| GAGATTAGGA | GATCGAGACC | ATCCTGGCCA | GCATGGTGAA | ACCCGTCTC | TACTANNAAA | 600 |
| TGGNAAAATT | ANCTGGGTGT | GGTCGCGTGC | NCCTGTAGTC | CCAGCTACTC | GTGAGGCTGA | 660 |
| GGCAGGAGAA | TCACTTGAAC | CGGGGAAATG | GAGGTTTCAG | TGAGCAGAGA | TCATNCCCCT | 720 |
| NCATTCCAGC | CTGGCGACAG | AGCAAGGCTC | CGTCNCCNAA | AAAATAAAAA | AAAACGTGAA | 780 |
| CAAATAAGAA | TATTTGTTGA | GCATAGCATG | GATGATAGTC | TTCTAATAGT | CAATCAATTA | 840 |
| CTTTATGAAA | GACAAATAAT | AGTTTGCTG | CTTCCTTACC | TCCTTTTGTT | TTGGGTTAAG | 900 |
| ATTTGGAGTG | TGGGCCAGGC | AC | | | | 922 |

( 2 ) INFORMATION FOR SEQ ID NO:28:

( i ) SEQUENCE CHARACTERISTICS:
        ( A ) LENGTH: 867 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:28:

| GATCTATAGC | TAGCCTTGGC | GTCTAGAAGA | TGGGTGTTGA | GAAGAGGGAG | TGGAAAGATA | 60 |
| TTTCCTCTGG | TCTTAACTTC | ATATCAGCCT | CCCCTAGACT | TCCAAATATC | CATACCTGCT | 120 |
| GGTTATAATT | AGTGGTGTTT | TCAGCCTCTG | ATTCTGTCAC | CAGGGGTTTT | AGAATCATAA | 180 |
| ATCCAGATTG | ATCTTGGGAG | TGTAAAAAAC | TGAGGCTCTT | TAGCTTCTTA | GGACAGCACT | 240 |
| TCCTGATTTT | GTTTCAACT | TCTAATCCTT | TGAGTGTTTT | TCATTCTGCA | GATGCTGAGT | 300 |
| TTGTGTGTGA | ACGGACACTG | AAATATTTTC | TAGGAATTGC | GGGAGGAAAA | TGGGTAGTTA | 360 |
| GCTATTTCTG | TAAGTATAAT | ACTATTTCTC | CCCTCCTCCC | TTTAACACCT | CAGAATTGCA | 420 |
| TTTTTACACC | TAACATTTAA | CACCTAAGGT | TTTTGCTGAT | GCTGAGTCTG | AGTTACCAAA | 480 |
| AGGTCTTTAA | ATTGTAATAC | TAAACTACTT | TTATCTTTAA | TATCACTTTG | TTCAAGATAA | 540 |
| GCTGGTGATG | CTGGGAAAAT | GGGTCTCTTT | TATAACTAAT | AGGACCTAAT | CTGCTCCTAG | 600 |
| CAATGTTAGC | ATATGAGCTA | GGGATTTATT | TAATAGTCGG | CAGGAATCCA | TGTGCARCAG | 660 |
| NCAAACTTAT | AATGTTTAAA | TTAAACATCA | ACTCTGTCTC | CAGAAGGAAA | CTGCTGCTAC | 720 |
| AAGCCTTATT | AAAGGGCTGT | GGCTTTAGAG | GGAAGGACCT | CTCCTCTGTC | ATTCTTCCTG | 780 |
| TGCTCTTTTG | TGAATCGCTG | ACCTCTCTAT | CTCCGTGAAA | AGAGCACGTT | CTTCTGCTGT | 840 |
| ATGTAACCTG | TCTTTTCTAT | GATCTCT | | | | 867 |

( 2 ) INFORMATION FOR SEQ ID NO:29:

( i ) SEQUENCE CHARACTERISTICS:
        ( A ) LENGTH: 561 base pairs
        ( B ) TYPE: nucleic acid
        ( C ) STRANDEDNESS: double 5,747,282

123                                                                                                          124

-continued ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:29:

| | | | | | | |
|---|---|---|---|---|---|---|
| NAAAAACGGG | GNNGGGANTG | GGCCTTAAAN | CCAAAGGGCN | AACTCCCCAA | CCATTNAAAA | 60 |
| ANTGACNGGG | GATTATTAAA | ANCGGCGGGA | AACATTTCAC | NGCCCAACTA | ATATTGTTAA | 120 |
| ATTAAAACCA | CCACCNCTGC | NCCAAGGAGG | GAAACTGCTG | CTACAAGCCT | TATTAAAGGG | 180 |
| CTGTGGCTTT | AGAGGGAAGG | ACCTCTCCTC | TGTCATTCTT | CCTGTGCTCT | TTTGTGAATC | 240 |
| GCTGACCTCT | CTATGTCCGT | GAAAAGAGCA | CGTTCTTCGT | CTGTATGTAA | CCTGTCTTTT | 300 |
| CTATGATCTC | TTTAGGGGTG | ACCCAGTCTA | TTAAAGAAAG | AAAAATGCTG | AATGAGGTAA | 360 |
| GTACTTGATG | TTACAAACTA | ACCAGAGATA | TTCATTCAGT | CATATAGTTA | AAAATGTATT | 420 |
| TGCTTCCTTC | CATCAATGCA | CCACTTTCCT | TAACAATGCA | CAAATTTTCC | ATGATAATGA | 480 |
| GGATCATCAA | GAATTATGCA | GGCCTGCACT | GTGGCTCATA | CCTATAATCC | CAGCGCTTTG | 540 |
| GGAGGCTGAG | GCGCTTGGAT | C | | | | 561 |

( 2 ) INFORMATION FOR SEQ ID NO:30:

( i ) SEQUENCE CHARACTERISTICS:
        ( A ) LENGTH: 567 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:30:

| | | | | | | |
|---|---|---|---|---|---|---|
| AATTTTTTGT | ATTTTTAGTA | GAGATGAGGT | TCACCATGTT | GGTCTAGATC | TGGTGTCGAA | 60 |
| CGTCCTGACC | TCAAGTGATC | TGCCAGCCTC | AGTCTCCCAA | AGTGCTAGGA | TTACAGGGGT | 120 |
| GAGCCACTGC | GCCTGGCCTG | AATGCCTAAA | ATATGACGTG | TCTGCTCCAC | TTCCATTGAA | 180 |
| GGAAGCTTCT | CTTTCTCTTA | TCCTGATGGG | TTGTGTTTGG | TTTCTTTCAG | CATGATTTTG | 240 |
| AAGTCAGAGG | AGATGTGGTC | AATGGAAGAA | ACCACCAAGG | TCCAAAGCGA | GCAAGAGAAT | 300 |
| CCCAGGACAG | AAAGGTAAAG | CTCCCTCCCT | CAAGTTGACA | AAAATCTCAC | CCCACCACTC | 360 |
| TGTATTCCAC | TCCCCTTTGC | AGAGATGGGC | CGCTTCATTT | TGTAAGACTT | ATTACATACA | 420 |
| TACACAGTGC | TAGATACTTT | CACACAGGTT | CTTTTTTCAC | TCTTCCATCC | CAACCACATA | 480 |
| AATAAGTATT | GTCTCTACTT | TATGAATGAT | AAAACTAAGA | GATTTAGAGA | GGCTGTGTAA | 540 |
| TTTGGATTCC | CGTCTCGGGT | TCAGATC | | | | 567 |

( 2 ) INFORMATION FOR SEQ ID NO:31:

( i ) SEQUENCE CHARACTERISTICS:
        ( A ) LENGTH: 633 base pairs
        ( B ) TYPE: nucleic acid
        ( C ) STRANDEDNESS: double ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:31:

| | | | | | | |
|---|---|---|---|---|---|---|
| TTGGCCTGAT | TGGTGACAAA | AGTGAGATGC | TCAGTCCTTG | AATGACAAAG | AATGCCTGTA | 60 |
| GAGTTGCAGG | TCCAACTACA | TATGCACTTC | AAGAAGATCT | TCTGAAATCT | AGTAGTGTTC | 120 |
| TGGACATTGG | ACTGCTTGTC | CCTGGGAAGT | AGCAGCAGAA | ATGATCGGTG | GTGAACAGAA | 180 |
| GAAAAAGAAA | AGCTCTTCCT | TTTTGAAAGT | CTGTTTTTTG | AATAAAAGCC | AATATTCTTT | 240 |
| TATAACTAGA | TTTTCCTTCT | CTCCATTCCC | CTGTCCCTCT | CTCTTCCTCT | CTTCTTCCAG | 300 |
| ATCTTCAGGG | GGCTAGAAAT | CTGTTGCTAT | GGGCCCTTCA | CCAACATGCC | CACAGGTAAG | 360 |
| AGCCTGGGAG | AACCCCAGAG | TTCCAGCACC | AGCCTTTGTC | TTACATAGTG | GAGTATTATA | 420 |
| AGCAAGGTCC | CACGATGGGG | GTTCCTCAGA | TTGCTGAAAT | GTTCTAGAGG | CTATTCTATT | 480 |
| TCTCTACCAC | TCTCCAAACA | AAACAGCACC | TAAATGTTAT | CCTATGGCAA | AAAAAAACTA | 540 |
| TACCTTGTCC | CCCTTCTCAA | GAGCATGAAG | GTGGTTAATA | GTTAGGATTC | AGTATGTTAT | 600 |
| GTGTTCAGAT | GGCGTTGAGC | TGCTGTTAGT | GCC | | | 633 |

( 2 ) INFORMATION FOR SEQ ID NO:32:

( i ) SEQUENCE CHARACTERISTICS:
        ( A ) LENGTH: 470 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:32:

| | | | | | | |
|---|---|---|---|---|---|---|
| TTTGAGAGAC | TATCAAACCT | TATACCAAGT | GGCCTTATGG | AGACTGATAA | CCAGAGTACA | 60 |
| TGGCATATCA | GTGGCAAATT | GACTTAAAAT | CCATACCCCT | ACTATTTTAA | GACCATTGTC | 120 |
| CTTTGGAGCA | GAGAGACAGA | CTCTCCCATT | GAGAGGTCTT | GCTATAAGCC | TTCATCCGGA | 180 |
| GAGTGTAGGG | TAGAGGGCCT | GGGTTAAGTA | TGCAGATTAC | TGCAGTGATT | TTACATGTAA | 240 |
| ATGTCCATTT | TAGATCAACT | GGAATGGATG | GTACAGCTGT | GTGGTGCTTC | TGTGGTGAAG | 300 |
| GAGCTTTCAT | CATTCACCCT | TGGCACAGTA | AGTATTGGGT | GCCCTGTCAG | TGTGGGAGGA | 360 |
| CACAATATTC | TCTCCTGTGA | GCAAGACTGG | CACCTGTCAG | TCCCTATGGA | TGCCCCTACT | 420 |
| GTAGCCTCAG | AAGTCTTCTC | TGCCCACATA | CCTGTGCCAA | AAGACTCCAT | | 470 |

( 2 ) INFORMATION FOR SEQ ID NO:33:

( i ) SEQUENCE CHARACTERISTICS:
        ( A ) LENGTH: 517 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:33:

| | | | | | |
|---|---|---|---|---|---|
| GGTGGTACGT | GTCTGTAGTT | CCAGCTACTT | GGGAGGCTGA | GATGGAAGGA | TTGCTTGAGC | 60
| CCAGGAGGCA | GAGGTGGNAN | NTTACGCTGA | GATCACACCA | CTGCACTCCA | GCCTGGGTGA | 120
| CAGAGCAAGA | CCCTGTCTCA | AAAACAAACA | AAAAAAATGA | TGAAGTGACA | GTTCCAGTAG | 180
| TCCTACTTTG | ACACTTTGAA | TGCTCTTTCC | TTCCTGGGGA | TCCAGGGTGT | CCACCCAATT | 240
| GTGGTTGTGC | AGCCAGATGC | CTGGACAGAG | GACAATGGCT | TCCATGGTAA | GGTGCCTCGC | 300
| ATGTACCTGT | GCTATTAGTG | GGGTCCTTGT | GCATGGGTTT | GGTTTATCAC | TCATTACCTG | 360
| GTGCTTGAGT | AGCACAGTTC | TTGGCACATT | TTTAAATATT | TGTTGAATGA | ATGGCTAAAA | 420
| TGTCTTTTTG | ATGTTTTTAT | TGTTATTTGT | TTTATATTGT | AAAAGTAATA | CATGAACTGT | 480
| TTCCATGGGG | TGGAGTAAG | ATATGAATGT | TCATCAC | | | 517

( 2 ) INFORMATION FOR SEQ ID NO:34:

( i ) SEQUENCE CHARACTERISTICS:
        ( A ) LENGTH: 434 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:34:

| | | | | | |
|---|---|---|---|---|---|
| CAGTAATCCT | NAGAACTCAT | ACGACCGGGC | CCCTGGAGTC | GNTGNTTNGA | GCCTAGTCCN | 60
| GGAGAATGAA | TTGACACTAA | TCTCTGCTTG | TGTTCTCTGT | CTCCAGCAAT | TGGGCAGATG | 120
| TGTGAGGCAC | CTGTGGTGAC | CCGAGAGTGG | GTGTTGGACA | GTGTAGCACT | CTACCAGTGC | 180
| CAGGAGCTGG | ACACCTACCT | GATACCCCAG | ATCCCCACA | GCCACTACTG | ACTGCAGCCA | 240
| GCCACAGGTA | CAGAGCCACA | GGACCCCAAG | AATGAGCTTA | CAAAGTGGCC | TTTCCAGGCC | 300
| CTGGGAGCTC | CTCTCACTCT | TCAGTCCTTC | TACTGTCCTG | GCTACTAAAT | ATTTTATGTA | 360
| CATCAGCCTG | AAAAGGACTT | CTGGCTATGC | AAGGGTCCCT | TAAAGATTTT | CTGCTTGAAG | 420
| TCTCCCTTGG | AAAT | | | | | 434

( 2 ) INFORMATION FOR SEQ ID NO:35:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Homo sapiens ( x i ) SEQUENCE DESCRIPTION: SEQ ID NO:35:

GATAAATTAA AACTGCGACT GCGCGGCGTG                         30

( 2 ) INFORMATION FOR SEQ ID NO:36:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:36:

GTAGTAGAGT CCCGGGAAAG GGACAGGGGG                         30

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:37:

ATATATATAT GTTTTTCTAA TGTGTTAAAG                         30

( 2 ) INFORMATION FOR SEQ ID NO:38:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:38:

GTAAGTCAGC ACAAGAGTGT ATTAATTTGG                         30

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:39:

TTTCTTTTTC TCCCCCCCCT ACCCTGCTAG    30

( 2 ) INFORMATION FOR SEQ ID NO:40:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:40:

GTAAGTTTGA ATGTGTTATG TGGCTCCATT    30

( 2 ) INFORMATION FOR SEQ ID NO:41:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:41:

AGCTACTTTT TTTTTTTTTT TTTGAGACAG    30

( 2 ) INFORMATION FOR SEQ ID NO:42:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:42:

GTAAGTGCAC ACCACCATAT CCAGCTAAAT    30

( 2 ) INFORMATION FOR SEQ ID NO:43:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:43:

AATTGTTCTT TCTTTCTTTA TAATTTATAG 30

( 2 ) INFORMATION FOR SEQ ID NO:44:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:44:

GTATATAATT TGGTAATGAT GCTAGGTTGG 30

( 2 ) INFORMATION FOR SEQ ID NO:45:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:45:

GAGTGTGTTT CTCAAACAAT TTAATTTCAG 30

( 2 ) INFORMATION FOR SEQ ID NO:46:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:46:

GTAAGTGTTG AATATCCCAA GAATGACACT 30

( 2 ) INFORMATION FOR SEQ ID NO:47:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens

135

-continued ( x i ) SEQUENCE DESCRIPTION: SEQ ID NO:47:

AAACATAATG TTTTCCCTTG TATTTTACAG                              30

( 2 ) INFORMATION FOR SEQ ID NO:48:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:48:

GTAAAACCAT TTGTTTTCTT CTTCTTCTTC                              30

( 2 ) INFORMATION FOR SEQ ID NO:49:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:49:

TGCTTGACTG TTCTTTACCA TACTGTTTAG                              30

( 2 ) INFORMATION FOR SEQ ID NO:50:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:50:

GTAAGGGTCT CAGGTTTTTT AAGTATTTAA                              30

( 2 ) INFORMATION FOR SEQ ID NO:51:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:51:

TGATTTATTT TTTGGGGGA AATTTTTTAG           30

( 2 ) INFORMATION FOR SEQ ID NO:52:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:52:

GTGAGTCAAA GAGAACCTTT GTCTATGAAG           30

( 2 ) INFORMATION FOR SEQ ID NO:53:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:53:

TCTTATTAGG ACTCTGTCTT TTCCCTATAG           30

( 2 ) INFORMATION FOR SEQ ID NO:54:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:54:

GTAATGGCAA AGTTTGCCAA CTTAACAGGC           30

( 2 ) INFORMATION FOR SEQ ID NO:55:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:55:

GAGTACCTTG TTATTTTTGT ATATTTTCAG                     30

( 2 ) INFORMATION FOR SEQ ID NO:56:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( v i ) ORIGINAL SOURCE:
      ( A ) ORGANISM: Homo sapiens ( x i ) SEQUENCE DESCRIPTION: SEQ ID NO:56:

GTATTGGAAC CAGGTTTTTG TGTTTGCCCC                     30

( 2 ) INFORMATION FOR SEQ ID NO:57:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( v i ) ORIGINAL SOURCE:
      ( A ) ORGANISM: Homo sapiens ( x i ) SEQUENCE DESCRIPTION: SEQ ID NO:57:

ACATCTGAAC CTCTGTTTTT GTTATTTAAG                     30

( 2 ) INFORMATION FOR SEQ ID NO:58:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( v i ) ORIGINAL SOURCE:
      ( A ) ORGANISM: Homo sapiens ( x i ) SEQUENCE DESCRIPTION: SEQ ID NO:58:

AGGTAAAAAG CGTGTGTGTG TGTGCACATG                     30

( 2 ) INFORMATION FOR SEQ ID NO:59:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( v i ) ORIGINAL SOURCE:
      ( A ) ORGANISM: Homo sapiens ( x i ) SEQUENCE DESCRIPTION: SEQ ID NO:59:

CATTTTCTTG GTACCATTTA TCGTTTTTGA 30

( 2 ) INFORMATION FOR SEQ ID NO:60:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Homo sapiens ( x i ) SEQUENCE DESCRIPTION: SEQ ID NO:60:

GTGTGTATTG TTGGCCAAAC ACTGATATCT 30

( 2 ) INFORMATION FOR SEQ ID NO:61:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Homo sapiens ( x i ) SEQUENCE DESCRIPTION: SEQ ID NO:61:

AGTAGATTTG TTTTCTCATT CCATTTAAAG 30

( 2 ) INFORMATION FOR SEQ ID NO:62:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Homo sapiens ( x i ) SEQUENCE DESCRIPTION: SEQ ID NO:62:

GTAAGAAACA TCAATGTAAA GATGCTGTGG 30

( 2 ) INFORMATION FOR SEQ ID NO:63:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Homo sapiens ( x i ) SEQUENCE DESCRIPTION: SEQ ID NO:63:

ATGGTTTTCT CCTTCCATTT ATCTTTCTAG 30

( 2 ) INFORMATION FOR SEQ ID NO:64:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:64:

GTAATATTTC ATCTGCTGTA TTGGAACAAA 30

( 2 ) INFORMATION FOR SEQ ID NO:65:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:65:

TGTAAATTAA ACTTCTCCCA TTCCTTTCAG 30

( 2 ) INFORMATION FOR SEQ ID NO:66:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:66:

GTGAGTGTAT CCATATGTAT CTCCCTAATG 30

( 2 ) INFORMATION FOR SEQ ID NO:67:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:67:

ATGATAATGG AATATTTGAT TTAATTTCAG 30

( 2 ) INFORMATION FOR SEQ ID NO:68:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:68:

GTATACCAAG AACCTTTACA GAATACCTTG 30

( 2 ) INFORMATION FOR SEQ ID NO:69:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:69:

CTAATCCTTT GAGTGTTTTT CATTCTGCAG 30

( 2 ) INFORMATION FOR SEQ ID NO:70:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:70:

GTAAGTATAA TACTATTTCT CCCCTCCTCC 30

( 2 ) INFORMATION FOR SEQ ID NO:71:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:71:

TGTAACCTGT CTTTTCTATG ATCTCTTTAG　　　　　　　　　　　　　　　　　　30

( 2 ) INFORMATION FOR SEQ ID NO:72:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:72:

GTAAGTACTT GATGTTACAA ACTAACCAGA　　　　　　　　　　　　　　　　　　30

( 2 ) INFORMATION FOR SEQ ID NO:73:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:73:

TCCTGATGGG TTGTGTTTGG TTTCTTTCAG　　　　　　　　　　　　　　　　　　30

( 2 ) INFORMATION FOR SEQ ID NO:74:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:74:

GTAAAGCTCC CTCCCTCAAG TTGACAAAAA　　　　　　　　　　　　　　　　　　30

( 2 ) INFORMATION FOR SEQ ID NO:75:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:75:

CTGTCCTCT CTCTTCCTCT CTTCTTCCAG 30

( 2 ) INFORMATION FOR SEQ ID NO:76:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:76:

GTAAGAGCCT GGGAGAACCC CAGAGTTCCA 30

( 2 ) INFORMATION FOR SEQ ID NO:77:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:77:

AGTGATTTTA CATGTAAATG TCCATTTTAG 30

( 2 ) INFORMATION FOR SEQ ID NO:78:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:78:

GTAAGTATTG GGTGCCCTGT CAGTGTGGGA 30

( 2 ) INFORMATION FOR SEQ ID NO:79:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:79:

TTGAATGCTC TTTCCTTCCT GGGGATCCAG                                    30

( 2 ) INFORMATION FOR SEQ ID NO:80:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Homo sapiens ( x i ) SEQUENCE DESCRIPTION: SEQ ID NO:80:

GTAAGGTGCC TCGCATGTAC CTGTGCTATT                                    30

( 2 ) INFORMATION FOR SEQ ID NO:81:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Homo sapiens ( x i ) SEQUENCE DESCRIPTION: SEQ ID NO:81:

CTAATCTCTG CTTGTGTTCT CTGTCTCCAG                                    30

( 2 ) INFORMATION FOR SEQ ID NO:82:

( i ) SEQUENCE CHARACTERISTICS:
    ( A ) LENGTH: 42 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Homo sapiens ( x i ) SEQUENCE DESCRIPTION: SEQ ID NO:82:

```
Cys Pro Ile Cys Leu Glu Leu Ile Lys Glu Pro Val Ser Thr Lys Cys
 1               5                  10                  15
Asp His Ile Phe Cys Lys Phe Cys Met Leu Lys Leu Leu Asn Gln Lys
                20                  25                  30
Lys Gly Pro Ser Gln Cys Pro Leu Cys Lys
                35                  40
```

( 2 ) INFORMATION FOR SEQ ID NO:83:

( i ) SEQUENCE CHARACTERISTICS:
    ( A ) LENGTH: 45 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( x i ) SEQUENCE DESCRIPTION: SEQ ID NO:83:

```
Cys Pro Ile Cys Leu Glu Leu Leu Lys Glu Pro Val Ser Ala Asp Cys
1               5                   10                  15

Asn His Ser Phe Cys Arg Ala Cys Ile Thr Leu Asn Tyr Glu Ser Asn
                20                  25                  30

Arg Asn Thr Asp Gly Lys Gly Asn Cys Pro Val Cys Arg
            35                  40                  45
```

( 2 ) INFORMATION FOR SEQ ID NO:84:

( i ) SEQUENCE CHARACTERISTICS:
        ( A ) LENGTH: 41 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO:84:

```
Cys Pro Ile Cys Leu Asp Met Leu Lys Asn Thr Met Thr Thr Lys Glu
1               5                   10                  15

Cys Leu His Arg Phe Cys Ser Asp Cys Ile Val Thr Ala Leu Arg Ser
                20                  25                  30

Gly Asn Lys Glu Cys Pro Thr Cys Arg
            35                  40
```

( 2 ) INFORMATION FOR SEQ ID NO:85:

( i ) SEQUENCE CHARACTERISTICS:
        ( A ) LENGTH: 42 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO:85:

```
Cys Pro Val Cys Leu Gln Tyr Phe Ala Glu Pro Met Met Leu Asp Cys
1               5                   10                  15

Gly His Asn Ile Cys Cys Ala Cys Leu Ala Arg Cys Trp Gly Thr Ala
                20                  25                  30

Cys Thr Asn Val Ser Cys Pro Gln Cys Arg
            35                  40
```

17Q-LINKED BREAST AND OVARIAN CANCER SUSCEPTIBILITY GENE

CROSS REFERENCE TO RELATED APPLICATIONS

This application is a continuation-in-part of application Ser. No. 08/409,305 filed on 24 Mar. 1995, abandoned, which is a continuation-in-part of application Ser. No. 08/348,824 filed on 29 Nov. 1994, abandoned, which is a continuation-in-part of application Ser. No. 08/308,104 filed on 16 Sep. 1994, which is a continuation-in-part of application Ser. No. 08/300,266, filed on 2 Sep. 1994, abandoned, which is a continuation-in-part of application Ser. No. 08/289,221, filed on 12 Aug. 1994, abandoned, all incorporated herein by reference.

FIELD OF THE INVENTION

The present invention relates generally to the field of human genetics. Specifically, the present invention relates to methods and materials used to isolate and detect a human breast and ovarian cancer predisposing gene (BRCA1), some mutant alleles of which cause susceptibility to cancer, in particular, breast and ovarian cancer. More specifically, the invention relates to germline mutations in the BRCA1 gene and their use in the diagnosis of predisposition to breast and ovarian cancer. The present invention further relates to somatic mutations in the BRCA1 gene in human breast and ovarian cancer and their use in the diagnosis and prognosis of human breast and ovarian cancer. Additionally, the invention relates to somatic mutations in the BRCA1 gene in other human cancers and their use in the diagnosis and prognosis of human cancers. The invention also relates to the therapy of human cancers which have a mutation in the BRCA1 gene, including gene therapy, protein replacement therapy and protein mimetics. The invention further relates to the screening of drugs for cancer therapy. Finally, the invention relates to the screening of the BRCA1 gene for mutations, which are useful for diagnosing the predisposition to breast and ovarian cancer.

The publications and other materials used herein to illuminate the background of the invention, and in particular, cases to provide additional details respecting the practice, are incorporated herein by reference, and for convenience, are referenced by author and date in the following text and respectively grouped in the appended List of References.

BACKGROUND OF THE INVENTION

The genetics of cancer is complicated, involving multiple dominant, positive regulators of the transformed state (oncogenes) as well as multiple recessive, negative regulators (tumor suppressor genes). Over one hundred oncogenes have been characterized. Fewer than a dozen tumor suppressor genes have been identified, but the number is expected to increase beyond fifty (Knudson, 1993).

The involvement of so many genes underscores the complexity of the growth control mechanisms that operate in cells to maintain the integrity of normal tissue. This complexity is manifest in another way. So far, no single gene has been shown to participate in the development of all, or even the majority of human cancers. The most common oncogenic mutations are in the H-ras gene, found in 10–15% of all solid tumors (Anderson et al., 1992). The most frequently mutated tumor suppressor genes are the TP53 gene, homozygously deleted in roughly 50% of all tumors, and CDKN2, which was homozygously deleted in 46% of tumor cell lines examined (Kamb et al., 1994). Without a target that is common to all transformed cells, the dream of a "magic bullet" that can destroy or revert cancer cells while leaving normal tissue unharmed is improbable. The hope for a new generation of specifically targeted antitumor drugs may rest on the ability to identify tumor suppressor genes or oncogenes that play general roles in control of cell division.

The tumor suppressor genes which have been cloned and characterized influence susceptibility to: 1) Retinoblastoma (RB1); 2) Wilms' tumor (WT1); 3) Li-Fraumeni (TP53); 4) Familial adenomatus polyposis (APC); 5) Neurofibromatosis type 1 (NF1); 6) Neurofibromatosis type 2 (NF2); 7) von Hippel-Lindau syndrome (VHL); 8) Multiple endocrine neoplasia type 2A (MEN2A); and 9) Melanoma (CDKN2).

Tumor suppressor loci that have been mapped genetically but not yet isolated include genes for: Multiple endocrine neoplasia type 1 (MEN1); Lynch cancer family syndrome 2 (LCFS2); Neuroblastoma (NB); Basal cell nevus syndrome (BCNS); Beckwith-Wiedemann syndrome (BWS); Renal cell carcinoma (RCC); Tuberous sclerosis 1 (TSC1); and Tuberous sclerosis 2 (TSC2). The tumor suppressor genes that have been characterized to date encode products with similarities to a variety of protein types, including DNA binding proteins (WT1), ancillary transcription regulators (RB1), GTPase activating proteins or GAPs (NF1), cytoskeletal components (NF2), membrane bound receptor kinases (MEN2A), cell cycle regulators (CDKN2) and others with no obvious similarity to known proteins (APC and VHL).

In many cases, the tumor suppressor gene originally identified through genetic studies has been shown to be lost or mutated in some sporadic tumors. This result suggests that regions of chromosomal aberration may signify the position of important tumor suppressor genes involved both in genetic predisposition to cancer and in sporadic cancer.

One of the hallmarks of several tumor suppressor genes characterized to date is that they are deleted at high frequency in certain tumor types. The deletions often involve loss of a single allele, a so-called loss of heterozygosity (LOH), but may also involve homozygous deletion of both alleles. For LOH, the remaining allele is presumed to be nonfunctional, either because of a preexisting inherited mutation, or because of a secondary sporadic mutation.

Breast cancer is one of the most significant diseases that affects women. At the current rate, American women have a 1 in 8 risk of developing breast cancer by age 95 (American Cancer Society, 1992). Treatment of breast cancer at later stages is often futile and disfiguring, making early detection a high priority in medical management of the disease. Ovarian cancer, although less frequent than breast cancer is often rapidly fatal and is the fourth most common cause of cancer mortality in American women. Genetic factors contribute to an ill-defined proportion of breast cancer incidence, estimated to be about 5% of all cases but approximately 25% of cases diagnosed before age 40 (Claus et al., 1991). Breast cancer has been subdivided into two types, early-age onset and late-age onset, based on an inflection in the age-specific incidence curve around age 50. Mutation of one gene, BRCA1, is thought to account for approximately 45% of familial breast cancer, but at least 80% of families with both breast and ovarian cancer (Easton et al., 1993).

Intense efforts to isolate the BRCA1 gene have proceeded since it was first mapped in 1990 (Hall et al., 1990; Narod et al., 1991). A second locus, BRCA2, has recently been mapped to chromosome 13q (Wooster et al., 1994) and appears to account for a proportion of early-onset breast cancer roughly equal to BRCA1, but confers a lower risk of ovarian cancer. The remaining susceptibility to early-onset breast cancer is divided between as yet unmapped genes for familial cancer, and rarer germline mutations in genes such as TP53 (Malkin et al., 1990). It has also been suggested that heterozygote carriers for defective forms of the Ataxia-Telangectasia gene are at higher risk for breast cancer (Swift et al., 1976; Swift et al., 1991). Late-age onset breast cancer is also often familial although the risks in relatives are not as high as those for early-onset breast cancer (Cannon-Albright et al., 1994; Mettlin et al., 1990). However, the percentage of such cases due to genetic susceptibility is unknown.

Breast cancer has long been recognized to be, in part, a familial disease (Anderson, 1972). Numerous investigators have examined the evidence for genetic inheritance and concluded that the data are most consistent with dominant inheritance for a major susceptibility locus or loci (Bishop and Gardner, 1980; Go et al., 1983; Williams and Anderson, 1984; Bishop et al., 1988; Newman et al., 1988; Claus et al., 1991). Recent results demonstrate that at least three loci exist which convey susceptibility to breast cancer as well as other cancers. These loci are the TP53 locus on chromosome 17p (Malkin et al., 1990), a 17q-linked susceptibility locus known as BRCA1 (Hall et al., 1990), and one or more loci responsible for the unmapped residual. Hall et al. (1990) indicated that the inherited breast cancer susceptibility in kindreds with early age onset is linked to chromosome 17q21; although subsequent studies by this group using a more appropriate genetic model partially refuted the limitation to early onset breast cancer (Margaritte et al., 1992).

Most strategies for cloning the 17q-linked breast cancer predisposing gene (BRCA1) require precise genetic localization studies. The simplest model for the functional role of BRCA1 holds that alleles of BRCA1 that predispose to cancer are recessive to wild type alleles; that is, cells that contain at least one wild type BRCA1 allele are not cancerous. However, cells that contain one wild type BRCA1 allele and one predisposing allele may occasionally suffer loss of the wild type allele either by random mutation or by chromosome loss during cell division (nondisjunction). All the progeny of such a mutant cell lack the wild type function of BRCA1 and may develop into tumors. According to this model, predisposing alleles of BRCA1 are recessive, yet susceptibility to cancer is inherited in a dominant fashion: women who possess one predisposing allele (and one wild type allele) risk developing cancer, because their mammary epithelial cells may spontaneously lose the wild type BRCA1 allele. This model applies to a group of cancer susceptibility loci known as tumor suppressors or antioncogenes, a class of genes that includes the retinoblastoma gene and neurofibromatosis gene. By inference this model may also explain the BRCA1 function, as has recently been suggested (Smith et al., 1992).

A second possibility is that BRCA1 predisposing alleles are truly dominant; that is, a wild type allele of BRCA1 cannot overcome the tumor forming role of the predisposing allele. Thus, a cell that carries both wild type and mutant alleles would not necessarily lose the wild type copy of BRCA1 before giving rise to malignant cells. Instead, mammary cells in predisposed individuals would undergo some other stochastic change(s) leading to cancer.

If BRCA1 predisposing alleles are recessive, the BRCA1 gene is expected to be expressed in normal mammary tissue but not functionally expressed in mammary tumors. In contrast, if BRCA1 predisposing alleles are dominant, the wild type BRCA1 gene may or may not be expressed in normal mammary tissue. However, the predisposing allele will likely be expressed in breast tumor cells.

The 17q linkage of BRCA1 was independently confirmed in three of five kindreds with both breast cancer and ovarian cancer (Narod et al., 1991). These studies claimed to localize the gene within a very large region, 15 centiMorgans (cM), or approximately 15 million base pairs, to either side of the linked marker pCMM86 (D17S74). However, attempts to define the region further by genetic studies, using markers surrounding pCMMS6, proved unsuccessful. Subsequent studies indicated that the gene was considerably more proximal (Easton et al., 1993) and that the original analysis was flawed (Margaritte et al., 1992). Hall et al. (1992) recently localized the BRCA1 gene to an approximately 8 cM interval (approximately 8 million base pairs) bounded by Mfd15 (D17S250) on the proximal side and the human GIP gene on the distal side. A slightly narrower interval for the BRCA1 locus, based on publicly available data, was agreed upon at the Chromosome 17 workshop in March of 1992 (Fain, 1992). The size of these regions and the uncertainty associated with them has made it exceedingly difficult to design and implement physical mapping and/or cloning strategies for isolating the BRCA1 gene.

Identification of a breast cancer susceptibility locus would permit the early detection of susceptible individuals and greatly increase our ability to understand the initial steps which lead to cancer. As susceptibility loci are often altered during tumor progression, cloning these genes could also be important in the development of better diagnostic and prognostic products, as well as better cancer therapies.

SUMMARY OF THE INVENTION

The present invention relates generally to the field of human genetics. Specifically, the present invention relates to methods and materials used to isolate and detect a human breast cancer predisposing gene (BRCA1), some alleles of which cause susceptibility to cancer, in particular breast and ovarian cancer. More specifically, the present invention relates to germline mutations in the BRCA1 gene and their use in the diagnosis of predisposition to breast and ovarian cancer. The invention further relates to somatic mutations in the BRCA1 gene in human breast cancer and their use in the diagnosis and prognosis of human breast and ovarian cancer. Additionally, the invention relates to somatic mutations in the BRCA1 gene in other human cancers and their use in the diagnosis and prognosis of human cancers. The invention also relates to the therapy of human cancers which have a mutation in the BRCA1 gene, including gene therapy, protein replacement therapy and protein mimetics. The invention further relates to the screening of drugs for cancer therapy. Finally, the invention relates to the screening of the BRCA1 gene for mutations, which are useful for diagnosing the predisposition to breast and ovarian cancer.

BRIEF DESCRIPTION OF THE DRAWINGS

FIG. 1 is reproduced from Fain, 1992.

FIG. 10A-10H show genomic sequence of BRCA1. The lower case letters denote intron sequence while the upper case letters denote exon sequence. Indefinite intervals within introns are designated with vvvvvvvvvvvvv. Known polymorphic sites are shown as underlined and boldface type.

DETAILED DESCRIPTION OF THE INVENTION

Figure 1:
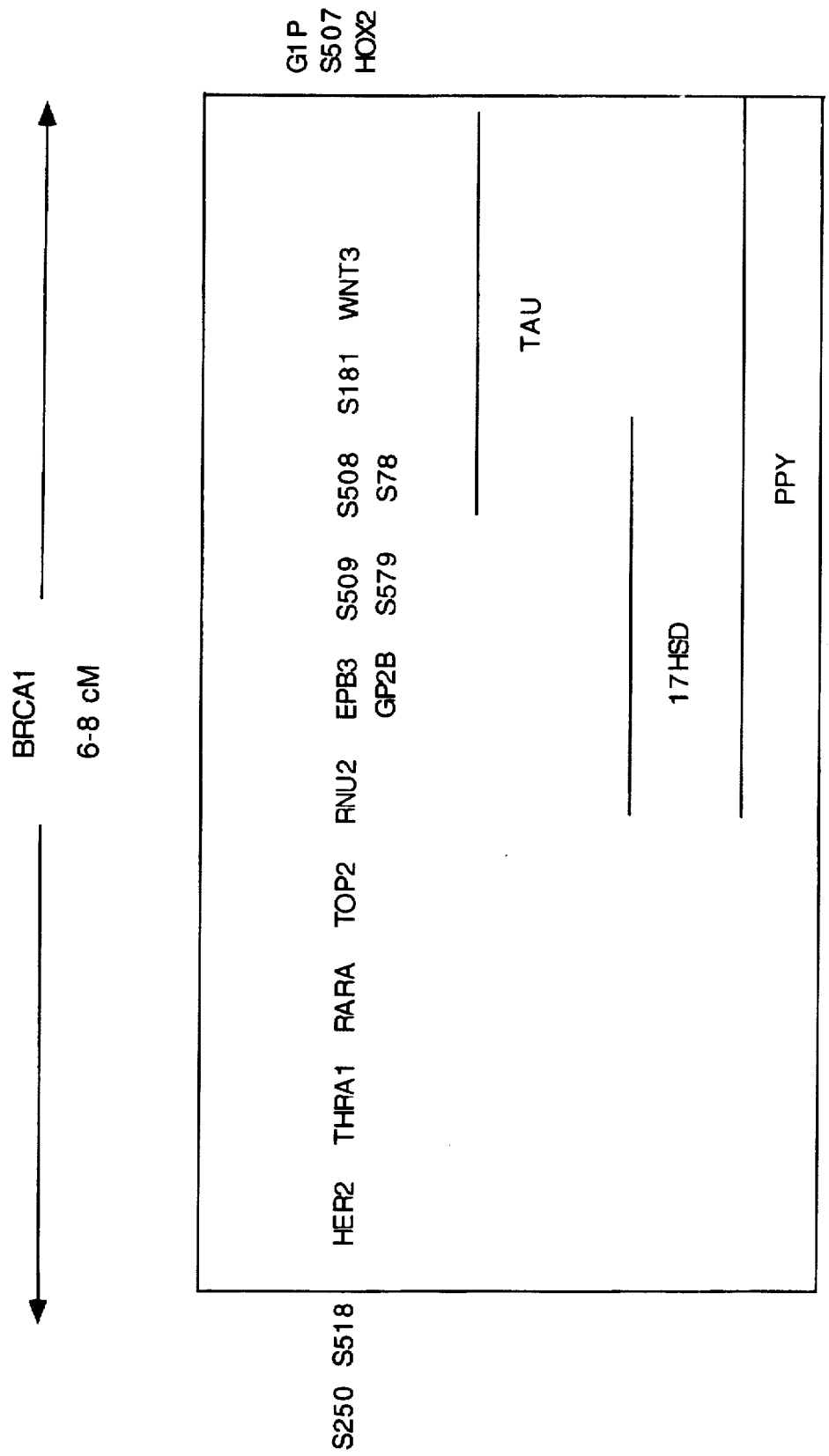
FIG. 1 is a diagram showing the order of loci neighboring BRCA1 as determined by the chromosome 17 workshop.

The present invention relates generally to the field of human genetics. Specifically, the present invention relates to methods and materials used to isolate and detect a human breast cancer predisposing gene (BRCA1), some alleles of which cause susceptibility to cancer, in particular breast and ovarian cancer. More specifically, the present invention relates to germline mutations in the BRCA1 gene and their use in the diagnosis of predisposition to breast and ovarian cancer. The invention further relates to somatic mutations in the BRCA1 gene in human breast cancer and their use in the diagnosis and prognosis of human breast and ovarian cancer. Additionally, the invention relates to somatic mutations in the BRCA1 gene in other human cancers and their use in the diagnosis and prognosis of human cancers. The invention also relates to the therapy of human cancers which have a mutation in the BRCA1 gene, including gene therapy, protein replacement therapy and protein mimetics. The invention further relates to the screening of drugs for cancer therapy. Finally, the invention relates to the screening of the BRCA1 gene for mutations, which are useful for diagnosing the predisposition to breast and ovarian cancer.

The present invention provides an isolated polynucleotide comprising all, or a portion of the BRCA1 locus or of a mutated BRCA1 locus, preferably at least eight bases and not more than about 100 kb in length. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the BRCA1 locus or its expression product in an analyte. Such methods may further comprise the step of amplifying the portion of the BRCA1 locus, and may further include a step of providing a set of polynucleotides which are primers for amplification of said portion of the BRCA1 locus. The method is useful for either diagnosis of the predisposition to cancer or the diagnosis or prognosis of cancer.

The present invention also provides isolated antibodies, preferably monoclonal antibodies, which specifically bind to an isolated polypeptide comprised of at least five amino acid residues encoded by the BRCA1 locus.

The present invention also provides kits for detecting in an analyte a polynucleotide comprising a portion of the BRCA1 locus, the kits comprising a polynucleotide complementary to the portion of the BRCA1 locus packaged in a suitable container, and instructions for its use.

The present invention further provides methods of preparing a polynucleotide comprising polymerizing nucleotides to yield a sequence comprised of at least eight consecutive nucleotides of the BRCA1 locus; and methods of preparing a polypeptide comprising polymerizing amino acids to yield a sequence comprising at least five amino acids encoded within the BRCA1 locus.

The present invention further provides methods of screening the BRCA1 gene to identify mutations. Such methods may further comprise the step of amplifying a portion of the BRCA1 locus, and may further include a step of providing a set of polynucleotides which are primers for amplification of said portion of the BRCA1 locus. The method is useful for identifying mutations for use in either diagnosis of the predisposition to cancer or the diagnosis or prognosis of cancer.

The present invention further provides methods of screening suspected BRCA1 mutant alleles to identify mutations in the BRCA1 gene.

In addition, the present invention provides methods of screening drugs for cancer therapy to identify suitable drugs for restoring BRCA1 gene product function.

Finally, the present invention provides the means necessary for production of gene-based therapies directed at cancer cells. These therapeutic agents may take the form of polynucleotides comprising all or a portion of the BRCA1 locus placed in appropriate vectors or delivered to target cells in more direct ways such that the function of the BRCA1 protein is reconstituted. Therapeutic agents may also take the form of polypeptides based on either a portion of, or the entire protein sequence of BRCA1. These may functionally replace the activity of BRCA1 in vivo.

It is a discovery of the present invention that the BRCA1 locus which predisposes individuals to breast cancer and ovarian cancer, is a gene encoding a BRCA1 protein, which has been found to have no significant homology with known protein or DNA sequences. This gene is termed BRCA1 herein. It is a discovery of the present invention that mutations in the BRCA1 locus in the germline are indicative of a predisposition to breast cancer and ovarian cancer. Finally, it is a discovery of the present invention that somatic mutations in the BRCA1 locus are also associated with breast cancer, ovarian cancer and other cancers, which represents an indicator of these cancers or of the prognosis of these cancers. The mutational events of the BRCA1 locus can involve deletions, insertions and point mutations within the coding sequence and the non-coding sequence.

Starting from a region on the long arm of human chromosome 17 of the human genome, 17q, which has a size estimated at about 8 million base pairs, a region which contains a genetic locus, BRCA1, which causes susceptibility to cancer, including breast and ovarian cancer, has been identified.

The region containing the BRCA1 locus was identified using a variety of genetic techniques. Genetic mapping techniques initially defined the BRCA1 region in terms of recombination with genetic markers. Based upon studies of large extended families ("kindreds") with multiple cases of breast cancer (and ovarian cancer cases in some kindreds), a chromosomal region has been pinpointed that contains the BRCA1 gene as well as other putative susceptibility alleles in the BRCA1 locus. Two meiotic breakpoints have been discovered on the distal side of the BRCA1 locus which are expressed as recombinants between genetic markers and the disease, and one recombinant on the proximal side of the BRCA1 locus. Thus, a region which contains the BRCA1 locus is physically bounded by these markers.

The use of the genetic markers provided by this invention allowed the identification of clones which cover the region from a human yeast artificial chromosome (YAC) or a human bacterial artificial chromosome (BAC) library. It also allowed for the identification and preparation of more easily manipulated cosmid, P1 and BAC clones from this region and the construction of a contig from a subset of the clones. These cosmids, P1s, YACs and BACs provide the basis for cloning the BRCA1 locus and provide the basis for developing reagents effective, for example, in the diagnosis and treatment of breast and/or ovarian cancer. The BRCA1 gene and other potential susceptibility genes have been isolated from this region. The isolation was done using software trapping (a computational method for identifying sequences likely to contain coding exons, from contiguous or discontinuous genomic DNA sequences), hybrid selection techniques and direct screening, with whole or partial cDNA inserts from cosmids, P1s and BACs, in the region to screen cDNA libraries. These methods were used to obtain sequences of loci expressed in breast and other tissue. These candidate loci were analyzed to identify sequences which confer cancer susceptibility. We have discovered that there are mutations in the coding sequence of the BRCA1 locus in kindreds which are responsible for the 17q-linked cancer susceptibility known as BRCA1. This gene was not known to be in this region. The present invention not only facilitates the early detection of certain cancers, so vital to patient survival, but also permits the detection of susceptible individuals before they develop cancer.

Population Resources

Large, well-documented Utah kindreds are especially important in providing good resources for human genetic studies. Each large kindred independently provides the power to detect whether a BRCA1 susceptibility allele is segregating in that family. Recombinants informative for localization and isolation of the BRCA1 locus could be obtained only from kindreds large enough to confirm the presence of a susceptibility allele. Large sibships are especially important for studying breast cancer, since penetrance of the BRCA1 susceptibility allele is reduced both by age and sex, making informative sibships difficult to find. Furthermore, large sibships are essential for constructing haplotypes of deceased individuals by inference from the haplotypes of their close relatives.

While other populations may also provide beneficial information, such studies generally require much greater effort, and the families are usually much smaller and thus less informative. Utah's age-adjusted breast cancer incidence is 20% lower than the average U.S. rate. The lower incidence in Utah is probably due largely to an early age at first pregnancy, increasing the probability that cases found in Utah kindreds carry a genetic predisposition.

Genetic Mapping

Given a set of informative families, genetic markers are essential for linking a disease to a region of a chromosome. Such markers include restriction fragment length polymorphisms (RFLPs) (Botstein et al., 1980), markers with a variable number of tandem repeats (VNTRs) (Jeffreys et al., 1985; Nakamura et al., 1987), and an abundant class of DNA polymorphisms based on short tandem repeats (STRs), especially repeats of CpA (Weber and May, 1989; Litt et al., 1989). To generate a genetic map, one selects potential genetic markers and tests them using DNA extracted from members of the kindreds being studied.

Genetic markers useful in searching for a genetic locus associated with a disease can be selected on an ad hoc basis, by densely covering a specific chromosome, or by detailed analysis of a specific region of a chromosome. A preferred method for selecting genetic markers linked with a disease involves evaluating the degree of informativeness of kindreds to determine the ideal distance between genetic markers of a given degree of polymorphism, then selecting markers from known genetic maps which are ideally spaced for maximal efficiency. Informativeness of kindreds is measured by the probability that the markers will be heterozygous in unrelated individuals. It is also most efficient to use STR markers which are detected by amplification of the target nucleic acid sequence using PCR; such markers are highly informative, easy to assay (Weber and May, 1989), and can be assayed simultaneously using multiplexing strategies (Skolnick and Wallace, 1988), greatly reducing the number of experiments required.

Once linkage has been established, one needs to find markers that flank the disease locus, i.e., one or more markers proximal to the disease locus, and one or more markers distal to the disease locus. Where possible, candidate markers can be selected from a known genetic map. Where none is known, new markers can be identified by the STR technique, as shown in the Examples.

Genetic mapping is usually an iterative process. In the present invention, it began by defining flanking genetic markers around the BRCA1 locus, then replacing these flanking markers with other markers that were successively closer to the BRCA1 locus. As an initial step, recombination events, defined by large extended kindreds, helped specifically to localize the BRCA1 locus as either distal or proximal to a specific genetic marker (Goldgar et al., 1994).

Figure 3:
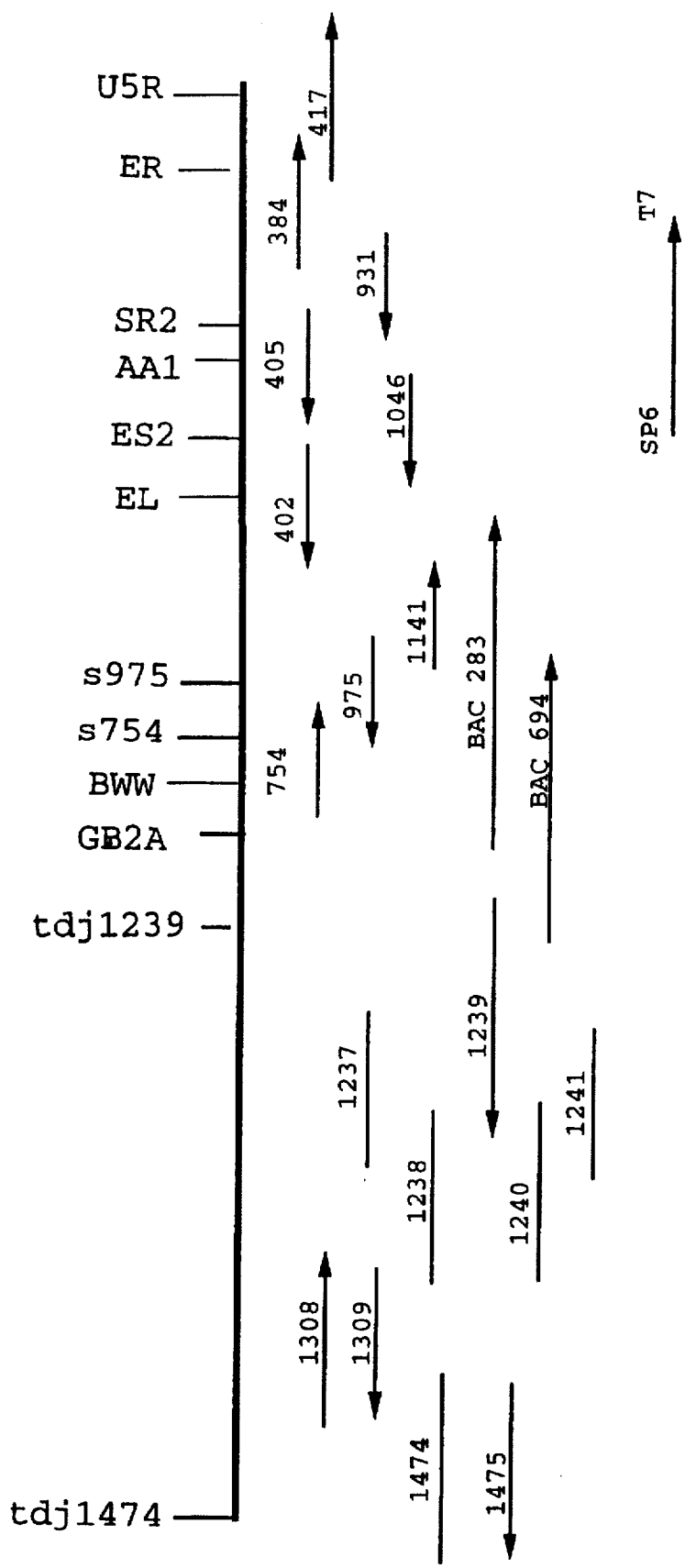
FIG. 3 is a schematic map of STSs, P1s and BACs in the BRCA1 region.

The region surrounding BRCA1, until the disclosure of the present invention, was not well mapped and there were few markers. Therefore, short repetitive sequences on cosmids subcloned from YACs, which had been physically mapped, were analyzed in order to develop new genetic markers. Using this approach, one marker of the present invention, 42D6, was discovered which replaced pCMM86 as the distal flanking marker for the BRCA1 region. Since 42D6 is approximately 14 cM from pCMM86, the BRCA1 region was thus reduced by approximately 14 centiMorgans (Easton et al., 1993). The present invention thus began by finding a much more closely linked distal flanking marker of the BRCA1 region. BRCA1 was then discovered to be distal to the genetic marker Mfd15. Therefore, BRCA1 was shown to be in a region of 6 to 10 million bases bounded by Mfd15 and 42D6. Marker Mfd191was subsequently discovered to be distal to Mfd15 and proximal to BRCA1. Thus, Mfd15 was replaced with Mfd191 as the closest proximal genetic marker. Similarly, it was discovered that genetic marker Mfd188 could replace genetic marker 42D6, narrowing the region containing the BRCA1 locus to approximately 1.5 million bases. Then the marker Mfd191 was replaced with tdj1474 as the proximal marker and Mfd188 was replaced with U5R as the distal marker, further narrowing the BRCA1 region to a small enough region to allow isolation and characterization of the BRCA1 locus (see FIG. 3), using techniques known in the art and described herein.

Physical Mapping

Three distinct methods were employed to physically map the region. The first was the use of yeast artificial chromosomes (YACs) to clone the region which is flanked by tdj1474 and U5R. The second was the creation of a set of P1, BAC and cosmid clones which cover the region containing the BRCA1 locus.

Yeast Artificial Chromosomes (YACs). Once a sufficiently small region containing the BRCA1 locus was identified, physical isolation of the DNA in the region proceeded by identifying a set of overlapping YACs which covers the region. Useful YACs can be isolated from known libraries, such as the St. Louis and CEPH YAC libraries, which are widely distributed and contain approximately 50,000 YACs each. The YACs isolated were from these publicly accessible libraries and can be obtained from a number of sources including the Michigan Genome Center. Clearly, others who had access to these YACs, without the disclosure of the present invention, would not have known the value of the specific YACs we selected since they would not have known which YACs were within, and which YACs outside of, the smallest region containing the BRCA1 locus.

Cosmid, P1 and BAC Clones. In the present invention, it is advantageous to proceed by obtaining cosmid, P1, and BAC clones to cover this region. The smaller size of these inserts, compared to YAC inserts, makes them more useful as specific hybridization probes. Furthermore, having the cloned DNA in bacterial cells, rather than in yeast cells, greatly increases the ease with which the DNA of interest can be manipulated, and improves the signal-to-noise ratio of hybridization assays. For cosmid subclones of YACs, the DNA is partially digested with the restriction enzyme Sau3A and cloned into the BamHI site of the pWE15 cosmid vector (Stratagene, cat. #1251201). The cosmids containing human sequences are screened by hybridization with human repetitive DNA (e.g., Gibco/BRL, Human $C_ot-1$ DNA, cat. 5279SA), and then fingerprinted by a variety of techniques, as detailed in the Examples.

P1 and BAC clones are obtained by screening libraries constructed from the total human genome with specific sequence tagged sites (STSs) derived from the YACs, cosmids or P1s and BACs, isolated as described herein.

These P1, BAC and cosmid clones can be compared by interspersed repetitive sequence (IRS) PCR and/or restriction enzyme digests followed by gel electrophoresis and comparison of the resulting DNA fragments ("fingerprints") (Maniatis et al., 1982). The clones can also be characterized by the presence of STSs. The fingerprints are used to define an overlapping contiguous set of clones which covers the region but is not excessively redundant, referred to herein as a "minimum tiling path". Such a minimum tiling path forms the basis for subsequent experiments to identify cDNAs which may originate from the BRCA1 locus.

Coverage of the Gap with P1 and BAC Clones. To cover any gaps in the BRCA1 contig between the identified cosmids with genomic clones, clones in P1 and BAC vectors which contain inserts of genomic DNA roughly twice as large as cosmids for P1s and still greater for BACs (Sternberg, 1990; Sternberg et al., 1990; Pierce et al., 1992; Shizuya et al., 1992) were used. P1 clones were isolated by Genome Sciences using PCR primers provided by us for screening. BACs were provided by hybridization techniques in Dr. Mel Simon's laboratory. The strategy of using P1 clones also permitted the covering of the genomic region with an independent set of clones not derived from YACs. This guards against the possibility of other deletions in YACs that have not been detected. These new sequences derived from the P1 clones provide the material for further screening for candidate genes, as described below.

Gene Isolation.

There are many techniques for testing genomic clones for the presence of sequences likely to be candidates for the coding sequence of a locus one is attempting to isolate, including but not limited to:

a. zoo blots b. identifying HTF islands c. exon trapping d. hybridizing cDNA to cosmids or YACs.

e. screening cDNA libraries.

(a) Zoo blots. The first technique is to hybridize cosmids to Southern blots to identify DNA sequences which are evolutionarily conserved, and which therefore give positive hybridization signals with DNA from species of varying degrees of relationship to humans (such as monkey, cow, chicken, pig, mouse and rat). Southern blots containing such DNA from a variety of species are commercially available (Clonetech, Cat. 7753-1).

(b) Identifying HTF islands. The second technique involves finding regions rich in the nucleotides C and G, which often occur near or within coding sequences. Such sequences are called HTF (HpaI tiny fragment) or CpG islands, as restriction enzymes specific for sites which contain CpG dimers cut frequently in these regions (Lindsay et al., 1987).

(c) Exon trapping. The third technique is exon trapping, a method that identifies sequences in genomic DNA which contain splice junctions and therefore are likely to comprise coding sequences of genes. Exon amplification (Buckler et al., 1991) is used to select and amplify exons from DNA clones described above. Exon amplification is based on the selection of RNA sequences which are flanked by functional 5' and/or 3' splice sites. The products of the exon amplification are used to screen the breast cDNA libraries to identify a manageable number of candidate genes for further study. Exon trapping can also be performed on small segments of sequenced DNA using computer programs or by software trapping.

(d) Hybridizing cDNA to Cosmids, P1s, BACs or YACs. The fourth technique is a modification of the selective enrichment technique which utilizes hybridization of cDNA to cosmids, P1s, BACs or YACs and permits transcribed sequences to be identified in, and recovered from cloned genomic DNA (Kandpal et al, 1990). The selective enrichment technique, as modified for the present purpose, involves binding DNA from the region of BRCA1 present in a YAC to a column matrix and selecting cDNAs from the relevant libraries which hybridize with the bound DNA, followed by amplification and purification of the bound DNA, resulting in a great enrichment for cDNAs in the region represented by the cloned genomic DNA.

(e) Identification of cDNAs. The fifth technique is to identify cDNAs that correspond to the BRCA1 locus. Hybridization probes containing putative coding sequences, selected using any of the above techniques, are used to screen various libraries, including breast tissue cDNA libraries, ovarian cDNA libraries, and any other necessary libraries.

Another variation on the theme of direct selection of cDNA was also used to find candidate genes for BRCA1 (Lovett et al., 1991; Futreal, 1993). This method uses cosmid, P1 or BAC DNA as the probe. The probe DNA is digested with a blunt cutting restriction enzyme such as HaeIII. Double stranded adapters are then ligated onto the DNA and serve as binding sites for primers in subsequent PCR amplification reactions using biotinylated primers. Target cDNA is generated from mRNA derived from tissue samples, e.g., breast tissue, by synthesis of either random primed or oligo(dT) primed first strand followed by second strand synthesis. The cDNA ends are rendered blunt and ligated onto double-stranded adapters. These adapters serve as amplification sites for PCR. The target and probe sequences are denatured and mixed with human $C_ot-1$ DNA to block repetitive sequences.

Solution hybridization is carried out to high $C_ot-\frac{1}{2}$ values to ensure hybridization of rare target cDNA molecules. The annealed material is then captured on avidin beads, washed at high stringency and the retained cDNAs are eluted and amplified by PCR. The selected cDNA is subjected to further rounds of enrichment before cloning into a plasmid vector for analysis.

Testing the cDNA for Candidacy

Proof that the cDNA is the BRCA1 locus is obtained by finding sequences in DNA extracted from affected kindred members which create abnormal BRCA1 gene products or abnormal levels of BRCA1 gene product. Such BRCA1 susceptibility alleles will co-segregate with the disease in large kindreds. They will also be present at a much higher frequency in non-kindred individuals with breast and ovarian cancer then in individuals in the general population. Finally, since tumors often mutate somatically at loci which are in other instances mutated in the germline, we expect to see normal germline BRCA1 alleles mutated into sequences which are identical or similar to BRCA1 susceptibility alleles in DNA extracted from tumor tissue. Whether one is comparing BRCA1 sequences from tumor tissue to BRCA1 alleles from the germline of the same individuals, or one is comparing germline BRCA1 alleles from cancer cases to those from unaffected individuals, the key is to find mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary, tertiary or quaternary protein structure. Silent mutations or those resulting in conservative amino acid substitutions would not generally be expected to disrupt protein function.

According to the diagnostic and prognostic method of the present invention, alteration of the wild-type BRCA1 locus is detected. In addition, the method can be performed by detecting the wild-type BRCA1 locus and confirming the lack of a predisposition to cancer at the BRCA1 locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. However, if both alleles are somatically mutated, then a late neoplastic state is indicated. The finding of BRCA1 mutations thus provides both diagnostic and prognostic information. A BRCA1 allele which is not deleted (e.g., found on the sister chromosome to a chromosome carrying a BRCA1 deletion) can be screened for other mutations, such as insertions, small deletions, and point mutations. It is believed that many mutations found in tumor tissues will be those leading to decreased expression of the BRCA1 gene product. However, mutations leading to nonfunctional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the BRCA1 gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below.

Predisposition to cancers, such as breast and ovarian cancer, and the other cancers identified herein, can be ascertained by testing any tissue of a human for mutations of the BRCA1 gene. For example, a person who has inherited a germline BRCA1 mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the BRCA1 gene. Alteration of a wild-type BRCA1 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. For a gene as large as BRCA1, manual sequencing is very labor-intensive, but under optimal conditions, mutations in the coding sequence of a gene are rarely missed. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation.

In order to detect the alteration of the wild-type BRCA1 gene in a tissue, it is helpful to isolate the tissue free from surrounding normal tissues. Means for enriching tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of cancer cases, tumors, or both. Southern blots displaying hybridizing fragments (differing in length from control DNA when probed with sequences near or including the BRCA1 locus) indicate a possible mutation. If restriction enzymes which produce very large restriction fragments are used, then pulsed field gel electrophoresis (PFGE) is employed.

Detection of point mutations may be accomplished by molecular cloning of the BRCA1 allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined.

There are six well known methods for a more complete, yet still indirect, test for confirming the presence of a susceptibility allele: 1) single stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Rano & Kidd, 1989). For allele-specific PCR, primers are used which hybridize at their 3' ends to a particular BRCA1 mutation. If the particular BRCA1 mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the BRCA1 mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type BRCA1 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the BRCA1 mRNA or gene but can be a segment of either. If the riboprobe comprises only a segment of the BRCA1 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the BRCA1 gene can also be detected using Southern hybridization, especially if the changes are gross rearrangements, such as deletions and insertions.

DNA sequences of the BRCA1 gene which have been amplified by use of PCR may also be screened using allele-specific probes. These probes are nucleic acid oligomers, each of which contains a region of the BRCA1 gene sequence harboring a known mutation. For example, one oligomer may be about 30 nucleotides in length, corresponding to a portion of the BRCA1 gene sequence. By use of a battery of such allele-specific probes, PCR amplification products can be screened to identify the presence of a previously identified mutation in the BRCA1 gene. Hybridization of allele-specific probes with amplified BRCA1 sequences can be performed, for example, on a nylon filter. Hybridization to a particular probe under stringent hybridization conditions indicates the presence of the same mutation in the tumor tissue as in the allele-specific probe.

The most definitive test for mutations in a candidate locus is to directly compare genomic BRCA1 sequences from cancer patients with those from a control population. Alternatively, one could sequence messenger RNA after amplification, e.g., by PCR, thereby eliminating the necessity of determining the exon structure of the candidate gene.

Mutations from cancer patients falling outside the coding region of BRCA1 can be detected by examining the non-coding regions, such as introns and regulatory sequences near or within the BRCA1 gene. An early indication that mutations in noncoding regions are important may come from Northern blot experiments that reveal messenger RNA molecules of abnormal size or abundance in cancer patients as compared to control individuals.

Alteration of BRCA1 mRNA expression can be detected by any techniques known in the art. These include Northern blot analysis, PCR amplification and RNase protection. Diminished mRNA expression indicates an alteration of the wild-type BRCA1 gene. Alteration of wild-type BRCA1 genes can also be detected by screening for alteration of wild-type BRCA1 protein. For example, monoclonal antibodies immunoreactive with BRCA1 can be used to screen a tissue. Lack of cognate antigen would indicate a BRCA1 mutation. Antibodies specific for products of mutant alleles could also be used to detect mutant BRCA1 gene product. Such immunological assays can be done in any convenient formats known in the art. These include Western blots, immunohistochemical assays and ELISA assays. Any means for detecting an altered BRCA1 protein can be used to detect alteration of wild-type BRCA1 genes. Functional assays, such as protein binding determinations, can be used. In addition, assays can be used which detect BRCA1 biochemical function. Finding a mutant BRCA1 gene product indicates alteration of a wild-type BRCA1 gene.

Mutant BRCA1 genes or gene products can also be detected in other human body samples, such as serum, stool, urine and sputum. The same techniques discussed above for detection of mutant BRCA1 genes or gene products in tissues can be applied to other body samples. Cancer cells are sloughed off from tumors and appear in such body samples. In addition, the BRCA1 gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant BRCA1 genes or gene products.

The methods of diagnosis of the present invention are applicable to any tumor in which BRCA1 has a role in tumorigenesis. The diagnostic method of the present invention is useful for clinicians, so they can decide upon an appropriate course of treatment.

The primer pairs of the present invention are useful for determination of the nucleotide sequence of a particular BRCA1 allele using PCR. The pairs of single-stranded DNA primers can be annealed to sequences within or surrounding the BRCA1 gene on chromosome 17q21 in order to prime amplifying DNA synthesis of the BRCA1 gene itself. A complete set of these primers allows synthesis of all of the nucleotides of the BRCA1 gene coding sequences, i.e., the exons. The set of primers preferably allows synthesis of both intron and exon sequences. Allele-specific primers can also be used. Such primers anneal only to particular BRCA1 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from BRCA1 sequences or sequences adjacent to BRCA1, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the BRCA1 open reading frame shown in SEQ ID NO: 1, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the BRCA1 gene or mRNA using other techniques.

It has been discovered that individuals with the wild-type BRCA1 gene do not have cancer which results from the BRCA1 allele. However, mutations which interfere with the function of the BRCA1 protein are involved in the pathogenesis of cancer. Thus, the presence of an altered (or a mutant) BRCA1 gene which produces a protein having a loss of function, or altered function, directly correlates to an increased risk of cancer. In order to detect a BRCA1 gene mutation, a biological sample is prepared and analyzed for a difference between the sequence of the BRCA1 allele being analyzed and the sequence of the wild-type BRCA1 allele. Mutant BRCA1 alleles can be initially identified by any of the techniques described above. The mutant alleles are then sequenced to identify the specific mutation of the particular mutant allele. Alternatively, mutant BRCA1 alleles can be initially identified by identifying mutant (altered) BRCA1 proteins, using conventional techniques. The mutant alleles are then sequenced to identify the specific mutation for each allele. The mutations, especially those which lead to an altered function of the BRCA1 protein, are then used for the diagnostic and prognostic methods of the present invention.

DEFINITIONS

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu et al., 1989a (for LCR). Reagents and hardware for conducting PCR are commercially available. Primers useful to amplify sequences from the BRCA1 region are preferably complementary to, and hybridize specifically to sequences in the BRCA1 region or in regions that flank a target region therein. BRCA1 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the BRCA1 polypeptides and fragments thereof or to polynucleotide sequences from the BRCA1 region, particularly from the BRCA1 locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the BRCA1 polypeptide or fragment. Monoclonal antibodies may be made by injecting mice with the protein polypeptides, fusion proteins or fragments thereof. Monoclonal antibodies will be screened by ELISA and tested for specific immunoreactivity with BRCA1 polypeptide or fragments thereof. See, Harlow & Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techinques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow & Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow & Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. The polynucleotides may be composed of DNA, RNA, or synthetic nucleotide analogs.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"BRCA1 Allele" refers to normal alleles of the BRCA1 locus as well as alleles carrying variations that predispose individuals to develop cancer of many sites including, for example, breast, ovarian, colorectal and prostate cancer. Such predisposing alleles are also called "BRCA1 susceptibility alleles".

"BRCA1 Locus," "BRCA1 Gene," "BRCA1 Nucleic Acids" or "BRCA1 Polynucleotide" each refer to polynucleotides, all of which are in the BRCA1 region, that are likely to be expressed in normal tissue, certain alleles of which predispose an individual to develop breast, ovarian, colorectal and prostate cancers. Mutations at the BRCA1 locus may be involved in the initiation and/or progression of other types of tumors. The locus is indicated in part by mutations that predispose individuals to develop cancer. These mutations fall within the BRCA1 region described infra. The BRCA1 locus is intended to include coding sequences, intervening sequences and regulatory elements controlling transcription and/or translation. The BRCA1 locus is intended to include all allelic variations of the DNA sequence.

These terms, when applied to a nucleic acid, refer to a nucleic acid which encodes a BRCA1 polypeptide, fragment, homolog or variant, including, e.g., protein fusions or deletions. The nucleic acids of the present invention will possess a sequence which is either derived from, or substantially similar to a natural BRCA1-encoding gene or one having substantial homology with a natural BRCA1-encoding gene or a portion thereof. The coding sequence for a BRCA1 polypeptide is shown in SEQ ID NO:1, with the amino acid sequence shown in SEQ ID NO:2.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the BRCA1 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a BRCA1-encoding sequence.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega Biotec, U. S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

"BRCA1 Region" refers to a portion of human chromosome 17q21 bounded by the markers tdj1474 and U5R. This region contains the BRCA1 locus, including the BRCA1 gene.

As used herein, the terms "BRCA1 locus," "BRCA1 allele" and "BRCA1 region" all refer to the double-stranded DNA comprising the locus, allele, or region, as well as either of the single-stranded DNAs comprising the locus, allele or region.

As used herein, a "portion" of the BRCA1 locus or region or allele is defined as having a minimal size of at least about eight nucleotides, or preferably about 15 nucleotides, or more preferably at least about 25 nucleotides, and may have a minimal size of at least about 40 nucleotides.

"BRCA1 protein" or "BRCA1 polypeptide" refer to a protein or polypeptide encoded by the BRCA1 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native BRCA1 sequence, preferably in excess of about 90%, and more preferably at least about 95% homologous. Also included are proteins encoded by DNA which hybridize under high or low stringency conditions, to BRCA1-encoding nucleic acids and closely related polypeptides or proteins retrieved by antisera to the BRCA1 protein (s).

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

"Probes". Polynucleotide polymorphisms associated with BRCA1 alleles which predispose to certain cancers or are associated with most cancers are detected by hybridization with a polynucleotide probe which forms a stable hybrid with that of the target sequence, under stringent to moderately stringent hybridization and wash conditions. If it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out nonspecific/ adventitious bindings, that is, which minimize noise. Since such indications identify neutral DNA polymorphisms as well as mutations, these indications need further analysis to demonstrate detection of a BRCA1 susceptibility allele.

Probes for BRCA1 alleles may be derived from the sequences of the BRCA1 region or its cDNAs. The probes may be of any suitable length, which span all or a portion of the BRCA1 region, and which allow specific hybridization to the BRCA1 region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding BRCA1 are preferred as probes. The probes may also be used to determine whether mRNA encoding BRCA1 is present in a cell or tissue.

"Protein modifications or fragments" are provided by the present invention for BRCA1 poly-peptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphoiylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of BRCA1 polypeptides. Immunological activities include both immunogenic function in a target immune system, as well as sharing of immunological epitopes for binding, serving as either a competitor or substitute antigen for an epitope of the BRCA1 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for BRCA1 polypeptides or fragments thereof is described below.

The present invention also provides for fusion polypeptides, comprising BRCA1 polypeptides and fragments. Homologous polypeptides may be fusions between two or more BRCA1 polypeptide sequences or between the sequences of BRCA1 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See, e.g., Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the BRCA1 polypeptides from other biological material, such as from cells transformed with recombinant nucleic acids encoding BRCA1, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A BRCA1 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C. typically in excess of 37° C. and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur & Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, and preferably at least about 95% identity.

"Substantially similar function" refers to the function of a modified nucleic acid or a modified protein, with reference to the wild-type BRCA1 nucleic acid or wild-type BRCA1 polypeptide. The modified polypeptide will be substantially homologous to the wild-type BRCA1 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type BRCA1 polypeptide. Alternatively, the similarity of function (activity) of the modified polypeptide may be higher than the activity of the wild-type BRCA1 polypeptide. The modified poly-peptide is synthesized using conventional techniques, or is encoded by a modified nucleic acid and produced using conventional techniques. The modified nucleic acid is prepared by conventional techniques. A nucleic acid with a function substantially similar to the wild-type BRCA1 gene function produces the modified protein described above.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wisc. 53705. Protein analysis software matches similar sequences using measure of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie & Fink, 1991. A general discussion of techniques and materials for human gene mapping, including mapping of human chromosome 17q, is provided, e.g., in White and Lalouel, 1988.

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention is described, e.g., in Sambrook et al., 1989 or Ausubel et al., 1992.

The polynucleotides of the present invention may also be produced by chemical synthesis, e.g., by the phosphoramidite method described by Beaucage & Carruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native BRCA1 protein or from other receptors or from secreted polypeptides of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al., 1989 or Ausubel et al. 1992.

An appropriate promoter and other necessary vector sequences will be selected so as to be functional in the host, and may include, when appropriate, those naturally associated with BRCA1 genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Moloney leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also Enhancers and Eukaryolic Gene Expression, Cold Spring Harbor Press, Cold Spring Harbor, N. Y. (1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the BRCA1 nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan, 1979. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of BRCA1 polypeptides.

Antisense polynucleotide sequences are useful in preventing or diminishing the expression of the BRCA1 locus, as will be appreciated by those skilled in the art. For example, polynucleotide vectors containing all or a portion of the BRCA1 locus or other sequences from the BRCA1 region (particularly those flanking the BRCA1 locus) may be placed under the control of a promoter in an antisense orientation and introduced into a cell. Expression of such an antisense construct within a cell will interfere with BRCA1 transcription and/or translation and/or replication.

The probes and primers based on the BRCA1 gene sequences disclosed herein are used to identify homologous BRCA1 gene sequences and proteins in other species. These BRCA1 gene sequences and proteins are used in the diagnostic/prognostic, therapeutic and drug screening methods described herein for the species from which they have been isolated.

Methods of Use: Nucleic Acid Diagnosis and Diagnostic Kits

In order to detect the presence of a BRCA1 allele predisposing an individual to cancer, a biological sample such as blood is prepared and analyzed for the presence or absence of susceptibility alleles of BRCA1. In order to detect the presence of neoplasia, the progression toward malignancy of a precursor lesion, or as a prognostic indicator, a biological sample of the lesion is prepared and analyzed for the presence or absence of mutant alleles of BRCA1. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant BRCA1 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 17q. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews & Kricka, 1988; Landegren et al., 1988; Mittlin, 1989; U.S. Pat. No. 4,868,105, and in EPO Publication No. 225,807.

As noted above, non-PCR based screening assays are also contemplated in this invention. An exemplary non-PCR based procedure is provided in Example 11. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding BRCA1. Exemplary probes are provided in Table 9 of this patent application and additionally include the nucleic acid probe corresponding to nucleotide positions 3631 to 3930 of SEQ ID NO:1. Allele specific probes are also contemplated within the scope of this example and exemplary allele specific probes include probes encompassing the predisposing mutations summarized in Tables 11 and 12 of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting BRCA1. Thus, in one example to detect the presence of BRCA1 in a cell sample, more than one probe complementary to BRCA1 is employed and in particular the number of different probes is alternatively 2, 3, or 5 different nucleic acid probe sequences. In another example, to detect the presence of mutations in the BRCA1 gene sequence in a patient, more than one probe complementary to BRCA1 is employed where the cocktail includes probes capable of binding to the allele-specific mutations identified in populations of patients with alterations in BRCA1. In this embodiment, any number of probes can be used, and will preferably include probes corresponding to the major gene mutations identified as predisposing an individual to breast cancer. Some candidate probes contemplated within the scope of the invention include probes that include the allele-specific mutations identified in Tables 11 and 12 and those that have the BRCA1 regions corresponding to SEQ ID NO:1 both 5' and 3' to the mutation site.

Methods of Use: Peptide Diagnosis and Diagnostic Kits

The neoplastic condition of lesions can also be detected on the basis of the alteration of wild-type BRCA1 polypeptide. Such alterations can be determined by sequence analysis in accordance with conventional techniques. More preferably, antibodies (polyclonal or monoclonal) are used to detect differences in, or the absence of BRCA1 peptides. The antibodies may be prepared as discussed above under the heading "Antibodies" and as further shown in Examples 12 and 13. Other techniques for raising and purifying antibodies are well known in the art and any such techniques may be chosen to achieve the preparations claimed in this invention. In a preferred embodiment of the invention, antibodies will immunoprecipitate BRCA1 proteins from solution as well as react with BRCA1 protein on Western or immunoblots of polyacrylamide gels. In another preferred embodiment, antibodies will detect BRCA1 proteins in paraffin or frozen tissue sections, using immunocytochemical techniques.

Preferred embodiments relating to methods for detecting BRCA1 or its mutations include enzyme linked immunosorbent assays (ELISA), radioimmunoassays (RIA), immunoradiometric assays (IRMA) and immtunloenzymatic assays (IEMA), including sandwich assays using monoclonal and/ or polyclonal antibodies. Exemplary sandwich assays are described by David et al. in U.S. Pat. Nos. 5 4,376,110 and 4,486,530, hereby incorporated by reference, and exemplified in Example 14.

Methods of Use: Drug Screening

This invention is particularly useful for screening compounds by using the BRCA1 polypeptide or binding fragment thereof in any of a variety of drug screening techniques.

The BRCA1 polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a BRCA1 polypeptide or fragment and the agent being tested, or examine the degree to which the formation of a complex between a BRCA1 polypeptide or fragment and a known ligand is interfered with by the agent being tested.

Thus, the present invention provides methods of screening for drugs comprising contacting such an agent with a BRCA1 polypeptide or fragment thereof and assaying (i) for the presence of a complex between the agent and the BRCA1 polypeptide or fragment, or (ii) for the presence of a complex between the BRCA1 polypeptide or fragment and a ligand, by methods well known in the art. In such competitive binding assays the BRCA1 polypeptide or fragment is typically labeled. Free BRCA1 polypeptide or fragment is separated from that present in a protein:protein complex, and the amount of free (i.e., uncomplexed) label is a measure of the binding of the agent being tested to BRCA1 or its interference with BRCA1:ligand binding, respectively.

Another technique for drug screening provides high throughput screening for compounds having suitable binding affinity to the BRCA1 polypeptides and is described in detail in Geysen, PCT published application WO 84/03564, published on Sep. 13, 1984. Briefly stated, large numbers of different small peptide test compounds are synthesized on a solid substrate, such as plastic pins or some other surface. The peptide test compounds are reacted with BRCA1 polypeptide and washed. Bound BRCA1 polypeptide is then detected by methods well known in the art.

Purified BRCA1 can be coated directly onto plates for use in the aforementioned drug screening techniques. However, non-neutralizing antibodies to the polypeptide can be used to capture antibodies to immobilize the BRCA1 polypeptide on the solid phase.

This invention also contemplates the use of competitive drug screening assays in which neutralizing antibodies capable of specifically binding the BRCA1 polypeptide compete with a test compound for binding to the BRCA1 polypeptide or fragments thereof. In this manner, the antibodies can be used to detect the presence of any peptide which shares one or more antigenic determinants of the BRCA1 polypeptide.

A further technique for drug screening involves the use of host eukaryotic cell lines or cells (such as described above) which have a nonfunctional BRCA1 gene. These host cell lines or cells are defective at the BRCA1 polypeptide level. The host cell lines or cells are grown in the presence of drug compound. The rate of growth of the host cells is measured to determine if the compound is capable of regulating the growth of BRCA1 defective cells.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., BRCA1 polypeptide) or, for example, of the BRCA1-receptor or ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., BRCA1 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idio-typic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved BRCA1 polypeptide activity or stability or which act as inhibitors, agonists, antagonists, etc. of BRCA1 polypeptide activity. By virtue of the availability of cloned BRCA1 sequences, sufficient amounts of the BRCA1 polypeptide may be made available to perform such analytical studies as x-ray crystallography. In addition, the knowledge of the BRCA1 protein sequence provided herein will guide those employing computer modeling techniques in place of, or in addition to x-ray crystallography.

Methods of Use: Gene Therapy

According to the present invention, a method is also provided of supplying wild-type BRCA1 function to a cell which carries mutant BRCA1 alleles. Supplying such a function should suppress neoplastic growth of the recipient cells. The wild-type BRCA1 gene or a part of the gene may be introduced into the cell in a vector such that the gene remains extrachromosomal. In such a situation, the gene will be expressed by the cell from the extrachromosomal location. If a gene fragment is introduced and expressed in a cell carrying a mutant BRCA1 allele, the gene fragment should encode a part of the BRCA1 protein which is required for non-neoplastic growth of the cell. More preferred is the situation where the wild-type BRCA1 gene or a part thereof is introduced into the mutant cell in such a way that it recombines with the endogenous mutant BRCA1 gene present in the cell. Such recombination requires a double recombination event which results in the correction of the BRCA1 gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the routineer. Cells transformed with the wild-type BRCA1 gene can be used as model systems to study cancer remission and drug treatments which promote such remission.

As generally discussed above, the BRCA1 gene or fragment, where applicable, may be employed in gene therapy methods in order to increase the amount of the expression products of such genes in cancer cells. Such gene therapy is particularly appropriate for use in both cancerous and pre-cancerous cells, in which the level of BRCA1 polypeptide is absent or diminished compared to normal cells. It may also be useful to increase the level of expression of a given BRCA1 gene even in those tumor cells in which the mutant gene is expressed at a "normal" level, but the gene product is not fully functional.

Gene therapy would be carried out according to generally accepted methods, for example, as described by Friedman, 1991. Cells from a patient's tumor would be first analyzed by the diagnostic methods described above, to ascertain the production of BRCA1 polypeptide in the tumor cells. A virus or plasmid vector (see further details below), containing a copy of the BRCA1 gene linked to expression control elements and capable of replicating inside the tumor cells, is prepared. Suitable vectors are known, such as disclosed in U.S. Pat. No. 5,252,479 and PCT published application WO 93/07282. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adenomatus-associated virus (Muzyczka, 1992; Ohi et al., 1990), herpesviruses including HSV and EBV (Margolskee, 1992; Johnson et al., 1992; Fink et al., 1992; Breakfield and Geller, 1987; Freese et al., 1990), and retroviruses of avian (Brandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Constantini and Lacy, 1981); membrane fusion-mediated transfer via liposomes (Felgner et al., 1987; Wang and Huang, 1989; Kaneda et al, 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989b; Wolff et al., 1991; Wagner et al., 1990; Wagner et al., 1991; Cotten et al., 1990; Curiel et al., 1991a; Curiel et al., 1991b). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Gene transfer techniques which target DNA directly to breast and ovarian tissues, e.g., epithelial cells of the breast or ovaries, is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. One appropriate receptor/ligand pair may include the estrogen receptor and its ligand, estrogen (and estrogen analogues). These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy involves two steps which can be performed singly or jointly. In the first step, prepubescent females who carry a BRCA1 susceptibility allele are treated with a gene delivery vehicle such that some or all of their mammary ductal epithelial precursor cells receive at least one additional copy of a functional normal BRCA1 allele. In this step, the treated individuals have reduced risk of breast cancer to the extent that the effect of the susceptible allele has been countered by the presence of the normal allele. In the second step of a preventive therapy, predisposed young females, in particular women who have received the proposed gene therapeutic treatment, undergo hormonal therapy to mimic the effects on the breast of a full term pregnancy.

Methods of Use: Peptide Therapy

Peptides which have BRCA1 activity can be supplied to cells which carry mutant or missing BRCA1 alleles. The sequence of the BRCA1 protein is disclosed (SEQ ID NO:2). Protein can be produced by expression of the cDNA sequence in bacteria, for example, using known expression vectors. Alternatively, BRCA1 polypeptide can be extracted from BRCA1-producing mammalian cells. In addition, the techniques of synthetic chemistry can be employed to synthesize BRCA1 protein. Any of such techniques can provide the preparation of the present invention which comprises the BRCA1 protein. The preparation is substantially free of other human proteins. This is most readily accomplished by synthesis in a microorganism or in vitro.

Active BRCA1 molecules can be introduced into cells by microinjection or by use of liposomes, for example. Alternatively, some active molecules may be taken up by cells, actively or by diffusion. Extracellular application of the BRCA1 gene product may be sufficient to affect tumor growth. Supply of molecules with BRCA1 activity should lead to partial reversal of the neoplastic state. Other molecules with BRCA1 activity (for example, peptides, drugs or organic compounds) may also be used to effect such a reversal. Modified polypeptides having substantially similar function are also used for peptide therapy.

Methods of Use: Transformed Hosts

Similarly, cells and animals which carry a mutant BRCA1 allele can be used as model systems to study and test for substances which have potential as therapeutic agents. The cells are typically cultured epithelial cells. These may be isolated from individuals with BRCA1 mutations, either somatic or germline. Alternatively, the cell line can be engineered to carry the mutation in the BRCA1 allele, as described above. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant BRCA1 alleles, usually from a second animal species, as well as insertion of disrupted homologous genes. Alternatively, the endogenous BRCA1 gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the growth of tumors must be assessed. If the test substance prevents or suppresses the growth of tumors, then the test substance is a candidate therapeutic agent for the treatment of the cancers identified herein. These animal models provide an extremely important testing vehicle for potential therapeutic products.

The present invention is described by reference to the following Examples, which are offered by way of illustration and are not intended to limit the invention in any manner. Standard techniques well known in the art or the techniques specifically described below were utilized.

EXAMPLE 1

Ascertain and Study Kindreds Likely to Have a 17q-Linked Breast Cancer Susceptibility Locus Extensive cancer prone kindreds were ascertained by our University of Utah collaborators from a defined population providing a large set of extended kindreds with multiple cases of breast cancer and many relatives available to study. The large number of meioses present in these large kindreds provided the power to detect whether the BRCA1 locus was segregating, and increased the opportunity for informative recombinants to occur within the small region being investigated. This vastly improved the chances of establishing linkage to the BRCA1 region, and greatly facilitated the reduction of the BRCA1 region to a manageable size, which permits identification of the BRCA1 locus itself.

Each kindred was extended through all available connecting relatives by our collaborators, and to all informative first degree relatives of each proband or cancer case. For these kindreds, additional breast cancer cases and individuals with cancer at other sites of interest (e.g. ovarian) who also appeared in the kindreds were identified through the tumor registry linked files. All breast cancers reported in the kindred which were not confirmed in the Utah Cancer Registry were researched. Medical records or death certificates were obtained for confirmation of all cancers. Each key connecting individual and all informative individuals were invited by our collaborators to participate by providing a blood sample from which DNA was extracted. They also sampled spouses and relatives of deceased cases so that the genotype of the deceased cases could be inferred from the genotypes of their relatives.

Ten kindreds which had three or more cancer cases with inferable genotypes were selected for linkage studies to 17q markers from a set of 29 kindreds originally ascertained for a study of proliferative breast disease and breast cancer (Skolnick et al., 1990). The criterion for selection of these kindreds was the presence of two sisters or a mother and her daughter with breast cancer. Additionally, two kindreds which have been studied by our collaborators since 1980 as part of their breast cancer linkage studies (K1001, K9018), six kindreds ascertained for the presence of clusters of breast and/or ovarian cancer (K2019, K2073, K2079, K2080, K2039, K2082) and a self-referred kindred with early onset breast cancer (K2035) were included. These kindreds were investigated and expanded in our collaborators clinic in the manner described above. Table 1 displays the characteristics of these 19 kindreds which are the subject of subsequent examples. In Table 1, for each kindred the total number of individuals in our database, the number of typed individuals, and the minimum, median, and maximum age at diagnosis of breast/ovarian cancer are reported. Kindreds are sorted in ascending order of median age at diagnosis of breast cancer. Four women diagnosed with both ovarian and breast cancer are counted in both categories.

TABLE 1

| | Description of the 19 Kindreds | | | | | | | | | |
|---|---|---|---|---|---|---|---|---|---|---|
| | No. of Individuals | | Breast | | | | Ovarian | | | |
| | | | | Age at Dx | | | | Age at Dx | | |
| KINDRED | Total | Sample | # Aff. | Min. | Med. | Max. | # Aff. | Min. | Med. | Max. |
| 1910 | 15 | 10 | 4 | 27 | 34 | 49 | — | — | — | — |
| 1001 | 133 | 98 | 13 | 28 | 37 | 64 | — | — | — | — |
| 2035 | 42 | 25 | 8 | 28 | 37 | 45 | 1 | — | 60 | — |
| 2027 | 21 | 11 | 4 | 34 | 38 | 41 | — | — | — | — |
| 9018 | 54 | 17 | 9 | 30 | 40 | 72 | 2 | 46 | 48 | 50 |
| 1925 | 50 | 27 | 4 | 39 | 42 | 53 | — | — | — | — |
| 1927 | 49 | 29 | 5 | 32 | 42 | 51 | — | — | — | — |
| 1911 | 28 | 21 | 7 | 28 | 42 | 76 | — | — | — | — |
| 1929 | 16 | 11 | 4 | 34 | 43 | 73 | — | — | — | — |
| 1901 | 35 | 19 | 10 | 31 | 44 | 76 | — | — | — | — |
| 2082 | 180 | 105 | 20 | 27 | 47 | 67 | 10 | 45 | 52 | 66 |
| 2019 | 42 | 19 | 10 | 42 | 53 | 79 | — | — | — | — |
| 1900 | 70 | 23 | 8 | 45 | 55 | 70 | 1 | — | 78 | — |

TABLE 1-continued

Description of the 19 Kindreds

| KINDRED | No. of Individuals | | Breast | | | | Ovarian | | | |
|---|---|---|---|---|---|---|---|---|---|---|
| | Total | Sample | # Aff. | Age at Dx | | | # Aff. | Age at Dx | | |
| | | | | Min. | Med. | Max. | | Min. | Med. | Max. |
| 2080 | 264 | 74 | 22+ | 27 | 55 | 92 | 4 | 45 | 53 | 71 |
| 2073 | 57 | 29 | 9 | 35 | 57 | 80 | — | — | — | — |
| 1917 | 16 | 6 | 4 | 43 | 58 | 61 | — | — | — | — |
| 1920 | 22 | 14 | 3 | 62 | 63 | 68 | — | — | — | — |
| 2079 | 136 | 18 | 14 | 38 | 66 | 84 | 4 | 52 | 59 | 65 |
| 2039 | 87 | 40 | 14 | 44 | 68 | 88 | 4 | 41 | 51 | 75 |

+Includes one case of male breast cancer.

EXAMPLE 2

Selection of Kindreds Which are Linked to Chromosome 17q and Localization of BRCA1 to the Interval Mfd15–Mfd188

For each sample collected in these 19 kindreds, DNA was extracted from blood (or in two cases from paraffin-embedded tissue blocks) using standard laboratory protocols. Genotyping in this study was restricted to short tandem repeat (STR) markers since, in general, they have high heterozygosity and PCR methods offer rapid turnaround while using very small amounts of DNA. To aid in this effort, four such STR markers on chromosome 17 were developed by screening a chromosome specific cosmid library for CA positive clones. Three of these markers localized to the long arm: (46E6, Easton et al., 1993); (42D6, Easton et al., 1993); 26C2 (D17S514, Oliphant et al., 1991), while the other, 12G6 (D17S513, Oliphant et al., 1991), localized to the short arm near the p53 tumor suppressor locus. Two of these, 42D6 and 46E6, were submitted to the Breast Cancer Linkage Consortium for typing of breast cancer families by investigators worldwide. Oligonucleotide sequences for markers not developed in our laboratory were obtained from published reports, or as part of the Breast Cancer Linkage Consortium, or from other investigators. All genotyping films were scored blindly with a standard lane marker used to maintain consistent coding of alleles. Key samples in the four kindreds presented here underwent duplicate typing for all relevant markers. All 19 kindreds have been typed for two polymorphic CA repeat markers: 42D6 (D17S588), a CA repeat isolated in our laboratory, and Mfd15 (D17S250), a CA repeat provided by J. Weber (Weber et al., 1990). Several sources of probes were used to create genetic markers on chromosome 17, specifically chromosome 17 cosmid and lambda phage libraries created from sorted chromosomes by the Los Alamos National Laboratories (van Dilla et al., 1986).

LOD scores for each kindred with these two markers (42D6, Mfd15) and a third marker, Mfd188 (D17S579, Hall et al., 1992), located roughly midway between these two markers, were calculated for two values of the recombination fraction, 0.001 and 0.1. (For calculation of LOD scores, see Oh, 1985). Likelihoods were computed under the model derived by Claus et al., 1991, which assumes an estimated gene frequency of 0.003, a lifetime risk in gene carriers of about 0.80, and population based age-specific risks for breast cancer in non-gene carriers. Allele frequencies for the three markers used for the LOD score calculations were calculated from our own laboratory typings of unrelated individuals in the CEPH panel (White and Lalouel, 1988).

Table 2 shows the results of the pairwise linkage analysis of each kindred with the three markers 42D6, Mfd188, and Mfd15.

TABLE 2

Pairwise Linkage Analysis of Kindreds

| | Mfd15 (D17S250) Recombination | | Mfd188 (D17S579) Recombination | | 42D6 (D17S588) Recombination | |
|---|---|---|---|---|---|---|
| KINDRED | 0.001 | 0.1 | 0.001 | 0.1 | 0.001 | 0.1 |
| 1910 | 0.06 | 0.30 | 0.06 | 0.30 | 0.06 | 0.30 |
| 1001 | −0.30 | −0.09 | NT | NT | −0.52 | −0.19 |
| 2035 | 2.34 | 1.85 | 0.94 | 0.90 | 2.34 | 1.82 |
| 2027 | −1.22 | −0.33 | −1.20 | −0.42 | −1.16 | −0.33 |
| 9018 | −0.54 | −0.22 | −0.17 | −0.10 | 0.11 | 0.07 |
| 1925 | 1.08 | 0.79 | 0.55 | 0.38 | −0.11 | −0.07 |
| 1927 | −0.41 | 0.01 | −0.35 | 0.07 | −0.44 | −0.02 |
| 1911 | −0.27 | −0.13 | −0.43 | −0.23 | 0.49 | 0.38 |
| 1929 | −0.49 | −0.25 | NT | NT | −0.49 | −0.25 |
| 1901 | 1.50 | 1.17 | 0.78 | 0.57 | 0.65 | 0.37 |
| 2082 | 4.25 | 3.36 | 6.07 | 5.11 | 2.00 | 3.56 |
| 2019 | −0.10 | −0.01 | −0.11 | −0.05 | −0.18 | −0.10 |
| 1900 | −0.14 | −0.11 | NT | NT | −0.12 | −0.05 |
| 2080 | −0.16 | −0.04 | 0.76 | 0.74 | −1.25 | −0.58 |
| 2073 | −0.41 | −0.29 | 0.63 | 0.49 | −0.23 | −0.13 |
| 1917 | −0.02 | −0.02 | NT | NT | −0.01 | 0.00 |
| 1920 | −0.03 | −0.02 | NT | NT | 0.00 | 0.00 |
| 2079 | 0.02 | 0.01 | −0.01 | −0.01 | 0.01 | 0.01 |
| 2039 | −1.67 | −0.83 | 0.12 | 0.59 | −1.15 | 0.02 |

NT—Kindred not typed for mfd188.

Using a criterion for linkage to 17q of a LOD score>1.0 for at least one locus under the CASH model (Claus et al., 1991), four of the 19 kindreds appeared to be linked to 17q (K1901, K1925, K2035, K2082). A number of additional kindreds showed some evidence of linkage but at this time could not be definitively assigned to the linked category. These included kindreds K1911, K2073, K2039, and K2080. Three of the 17q-linked kindreds had informative recombinants in this region and these are detailed below.

Kindred 2082 is the largest 17q-linked breast cancer family reported to date by any group. The kindred contains 20 cases of breast cancer, and ten cases of ovarian cancer. Two cases have both ovarian and breast cancer. The evidence of linkage to 17q for this family is overwhelming; the LOD score with the linked haplotype is over 6.0, despite the existence of three cases of breast cancer which appear to be sporadic, i.e., these cases share no part of the linked haplotype between Mfd15 and 42D6. These three sporadic cases were diagnosed with breast cancer at ages 46, 47, and 54. In smaller kindreds, sporadic cancers of this type greatly confound the analysis of linkage and the correct identification of key recombinants. The key recombinant in the 2082 kindred is a woman who developed ovarian cancer at age 45 whose mother and aunt had ovarian cancer at ages 58 and 66, respectively. She inherited the linked portion of the haplotype for both Mfd188 and 42D6 while inheriting unlinked alleles at Mfd15; this recombinant event placed BRCA1 distal to Mfd15.

K1901 is typical of early-onset breast cancer kindreds. The kindred contains 10 cases of breast cancer with a median age at diagnosis of 43.5 years of age; four cases were diagnosed under age 40. The LOD score for this kindred with the marker 42D6 is 1.5, resulting in a posterior probability of 17q-linkage of 0.96. Examination of haplotypes in this kindred identified a recombinant haplotype in an obligate male carrier and his affected daughter who was diagnosed with breast cancer at age 45. Their linked allele for marker Mfd15 differs from that found in all other cases in the kindred (except one case which could not be completely inferred from her children). The two haplotypes are identical for Mfd188 and 42D6. Accordingly, data from Kindred 1901 would also place the BRCA1 locus distal to Mfd15.

Kindred 2035 is similar to K1901 in disease phenotype. The median age of diagnosis for the eight cases of breast cancer in this kindred is 37. One case also had ovarian cancer at age 60. The breast cancer cases in this family descend from two sisters who were both unaffected with breast cancer until their death in the eighth decade. Each branch contains four cases of breast cancer with at least one case in each branch having markedly early onset. This kindred has a LOD score of 2.34 with Mfd5. The haplotypes segregating with breast cancer in the two branches share an identical allele at Mfd15 but differ for the distal loci Mfd188 and NM23 (a marker typed as part of the consortium which is located just distal to 42D6 (Hall et al., 1992)). Although the two haplotypes are concordant for marker 42D6, it is likely that the alleles are shared identical by state (the same allele but derived from different ancestors), rather than identical by descent (derived from a common ancestor) since the shared allele is the second most common allele observed at this locus. By contrast the linked allele shared at Mfd15 has a frequency of 0.04. This is a key recombinant in our dataset as it is the sole recombinant in which BRCA1 segregated with the proximal portion of the haplotype, thus setting the distal boundary to the BRCA1 region. For this event not to be a key recombinant requires that a second mutant BRCA1 gene be present in a spouse marrying into the kindred who also shares the rare Mfd15 allele segregating with breast cancer in both branches of the kindred. This event has a probability of less than one in a thousand. The evidence from this kindred therefore placed the BRCA1 locus proximal to Mfd188.

EXAMPLE 3

Creation of a Fine Structure Map and Refinement of the BRCA1 Region to Mfd191-Mfd188 using Additional STR Polymorphisms In order to improve the characterization of our recombinants and define closer flanking markers, a dense map of this relatively small region on chromosome 17q was required. The chromosome 17 workshop has produced a consensus map of this region (FIG. 1) based on a combination of genetic and physical mapping studies (Fain, 1992). This map contains both highly polymorphic STR polymorphisms, and a number of nonpolymorphic expressed genes. Because this map did not give details on the evidence for this order nor give any measure of local support for inversions in the order of adjacent loci, we viewed it as a rough guide for obtaining resources to be used for the development of new markers and construction of our own detailed genetic and physical map of a small region containing BRCA1. Our approach was to analyze existing STR markers provided by other investigators and any newly developed markers from our laboratory with respect to both a panel of meiotic (genetic) breakpoints identified using DNA from the CEPH reference families and a panel of somatic cell hybrids (physical breakpoints) constructed for this region. These markers included 26C2 developed in our laboratory which maps proximal to Mfd15, Mfd191 (provided by James Weber), THRA1 (Futreal et al., 1992a), and three polymorphisms kindly provided to us by Dr. Donald Black, NM23 (Hall et al. 1992), SCG40 (D17S181), and 6C1 (D17S293).

Genetic localization of markers. In order to localize new markers genetically within the region of interest, we have identified a number of key meiotic breakpoints within the region, both in the CEPH reference panel and in our large breast cancer kindred (K2082). Given the small genetic distance in this region, they are likely to be only a relatively small set of recombinants which can be used for this purpose, and they are likely to group markers into sets. The orders of the markers within each set can only be determined by physical mapping. However the number of genotypings necessary to position a new marker is minimized. These breakpoints are illustrated in Tables 3 and 4. Using this approach we were able to genetically order the markers THRA1, 6C1, SCG40, and Mfd191. As can be seen from Tables 3 and 4, THRA1 and MFD191 both map inside the Mfd15-Mfd188 region we had previously identified as containing the BRCA1 locus. In Tables 3 and 4, M/P indicates a maternal or paternal recombinant. A "1" indicates inherited allele is of grandpaternal origin, while a "0" indicates grandmaternal origin, and "-" indicates that the locus was untyped or uninformative.

TABLE 3

| | | | CEPH Recombinants | | | | | | |
|---|---|---|---|---|---|---|---|---|---|
| Family | ID | M/P | Mfd15 | THRA1 | Mfd191 | Mfd188 | SCG40 | 6C1 | 42D6 |
| 13292 | 4 | M | 1 | 1 | 1 | 0 | 0 | 0 | 0 |
| 13294 | 4 | M | 1 | 1 | 1 | 0 | 0 | 0 | 0 |
| 13294 | 6 | M | 0 | 0 | 1 | 1 | — | — | — |
| 1334 | 3 | M | 1 | 1 | 1 | 1 | 1 | 0 | 0 |
| 1333 | 4 | M | 1 | 1 | 1 | 0 | — | — | 0 |
| 1333 | 6 | M | 0 | 0 | 1 | 1 | — | — | 1 |
| 1333 | 8 | P | 1 | 0 | 0 | 0 | — | — | 0 |
| 1377 | 8 | M | 0 | — | 0 | 0 | 0 | 0 | 1 |

TABLE 4

Kindred 2082 Recombinants

| Family ID | M/P | Mfd15 | Mfd191 | Mfd188 | SCG40 | 6C1 | 42D6 |
|---|---|---|---|---|---|---|---|
| 75 | M | 0 | 1 | 1 | 1 | — | — |
| 63 | M | 0 | 0 | 1 | 1 | — | 1 |
| 125 | M | 1 | 1 | 1 | 0 | — | 0 |
| 40 | M | 1 | 1 | 0 | 0 | — | 0 |

Analysis of markers Mfd15, Mfd188, Mfd191, and THRA1 in our recombinant families. Mfd15, Mfd188, Mfd191 and THRA1 were typed in our recombinant families and examined for additional information to localize the BRCA1 locus. In kindred 1901, the Mfd15 recombinant was recombinant for THRA1 but uninformative for Mfd191, thus placing BRCA1 distal to THRA1. In K2082, the recombinant with Mfd15 also was recombinant with Mfd191, thus placing the BRCA1 locus distal to Mfd191 (Goldgar et al., 1994). Examination of THRA1 and Mfd191 in kindred K2035 yielded no further localization information as the two branches were concordant for both markers. However, SCG40 and 6C1 both displayed the same pattern as Mfd188, thus increasing our confidence in the localization information provided by the Mfd188 recombinant in this family. The BRCA1 locus, or at least a portion of it, therefore lies within an interval bounded by Mfd191 on the proximal side and Mfd188 on the distal side.

EXAMPLE 4

Development of Genetic and Physical Resources in the Region of Interest

To increase the number of highly polymorphic loci in the Mfd191-Mfd188 region, we developed a number of STR markers in our laboratory from cosmids and YACs which physically map to the region. These markers allowed us to further refine the region.

STSs were identified from genes known to be in the desired region to identify YACs which contained these loci, which were then used to identify subclones in cosmids, P1s or BACs. These subclones were then screened for the presence of a CA tandem repeat using a $(CA)_n$ oligonucleotide (Pharmacia). Clones with a strong signal were selected preferentially, since they were more likely to represent CA-repeats which have a large number of repeats and/or are of near-perfect fidelity to the $(CA)_n$ pattern. Both of these characteristics are known to increase the probability of polymorphism (Weber, 1990). These clones were sequenced directly from the vector to locate the repeat. We obtained a unique sequence on one side of the CA-repeat by using one of a set of possible primers complementary to the end of a CA-repeat, such as $(GT)_{10}T$. Based on this unique sequence, a primer was made to sequence back across the repeat in the other direction, yielding a unique sequence for design of a second primer flanking the CA-repeat. STRs were then screened for polymorphism on a small group of unrelated individuals and tested against the hybrid panel to confirm their physical localization. New markers which satisfied these criteria were then typed in a set of 40 unrelated individuals from the Utah and CEPH families to obtain allele frequencies appropriate for the study population. Many of the other markers reported in this study were tested in a smaller group of CEPH unrelated individuals to obtain similarly appropriate allele frequencies.

Using the procedure described above, a total of eight polymorphic STRs was found from these YACS. Of the loci identified in this manner, four were both polymorphic and localized to the BRCA1 region. Four markers did not localize to cliromosome 17, reflecting the chimeric nature of the YACs used. The four markers which were in the region were denoted AA1, ED2, 4–7, and YM29. AA1 and ED2 were developed from YACs positive for the RNU2 gene, 4–7 from an EPB3 YAC and YM29 from a cosmid which localized to the region by the hybrid panel. A description of the number of alleles, heterozygosity and source of these four and all other STR polymorphisms analyzed in the breast cancer kindreds is given below in Table 5.

TABLE 5

Polymorphic Short Tandem Repeat Markers Used for Fine Structure Mapping of the BRCA1 Locus

| Clone | Gene | Na** | Heterozygosity | Allele* Frequency (%) | | | | | |
|---|---|---|---|---|---|---|---|---|---|
| | | | | 1 | 2 | 3 | 4 | 5 | 6 |
| Mfd15 | D17S250 | 10 | 0.82 | 26 | 22 | 15 | 7 | 7 | 23 |
| THRA1 | THRA1 | 5 | | | | | | | |
| Mfd191 | D17S776 | 7 | 0.55 | 48 | 20 | 11 | 7 | 7 | 7 |
| ED2 | D17S1327 | 12 | 0.55 | 62 | 9 | 8 | 5 | 5 | 11 |
| AA1 | D17S1326 | 7 | 0.83 | 28 | 28 | 25 | 8 | 6 | 5 |
| CA375 | D17S184 | 10 | 0.75 | 26 | 15 | 11 | 9 | 9 | 20 |
| 4–7 | D17S1183 | 9 | 0.50 | 63 | 15 | 8 | 6 | 4 | 4 |
| YM29 | — | 9 | 0.62 | 42 | 24 | 12 | 7 | 7 | 8 |
| Mfd188 | D17S579 | 12 | 0.92 | 33 | 18 | 8 | 8 | 8 | 25 |
| SCG40 | D17S181 | 14 | 0.90 | 20 | 18 | 18 | 10 | 8 | 35 |
| 42D6 | D17S588 | 11 | 0.86 | 21 | 17 | 11 | 10 | 9 | 32 |
| 6C1 | D17S293 | 7 | 0.75 | 30 | 30 | 11 | 11 | 9 | 9 |
| Z109 | D17S750 | 9 | 0.70 | 33 | 27 | 7 | 7 | 7 | 19 |
| tdj1475 | D17S1321 | 13 | 0.84 | 21 | 16 | 11 | 11 | 8 | 33 |
| CF4 | D17S1320 | 6 | 0.63 | 50 | 27 | 9 | 7 | 4 | 3 |
| tdj1239 | D17S1328 | 10 | 0.80 | 86 | 10 | 9 | 7 | 4 | 14 |
| U5 | D17S1325 | 13 | 0.83 | 19 | 16 | 12 | 10 | 9 | 34 |

*Allele codes 1–5 are listed in decreasing frequency; allele numbers do not correspond to fragment sizes. Allele 6 frequency is the joint frequency of all other alleles for each locus.
**Number of alleles seen in the genetically independent DNA samples used for calculating allele frequencies.

The four STR polymorphisms which mapped physically to the region (4–7, ED2, AA1, YM29) were analyzed in the meiotic, breakpoint panel shown initially in Tables 3 and 4. Tables 6 and 7 contain the relevant CEPH data and Kindred 2082 data for localization of these four markers. In the tables, M/P indicates a maternal or paternal recombinant. A "1" indicates inherited allele is of grandpaternal origin, while a "0" indicates grandmaternal origin, and "-" indicates that the locus was untyped or uninformative.

TABLE 6

Key Recombinants Used for Genetic Ordering of New STR Loci Developed in Our Laboratory Within the BRCA1 Region of 17q

| CEPH Family | ID | M/P | Mfd15 | THRA1 | MFD191 | ED2 | AA1 | Z109 | 4–7 | YM29 | Mfd188 | SCG40 | 42D6 |
|---|---|---|---|---|---|---|---|---|---|---|---|---|---|
| 13292 | 4 | M | 1 | 1 | 1 | 1 | 1 | 0 | 0 | 0 | 0 | 0 | 0 |
| 13294 | 4 | M | 1 | 0 | 0 | — | 0 | — | — | — | 0 | — | — |
| 13294 | 6 | M | 0 | 0 | 1 | — | 1 | — | — | — | 1 | — | — |
| 1333 | 4 | M | 1 | 1 | 1 | — | 0 | — | — | 0 | 0 | — | 0 |
| 1333 | 6 | M | 0 | 0 | 1 | — | 1 | — | — | 1 | 1 | — | 1 |
| 1333 | 3 | M | 0 | 0 | 1 | — | — | — | 1 | 1 | 1 | — | 1 |

TABLE 7

Kindred 2082 Recombinants

| ID | M/P | Mfd15 | Mfd191 | ED2 | AA1 | 4–7 | YM29 | Mfd188 | SCG40 | 42D6 |
|---|---|---|---|---|---|---|---|---|---|---|
| 63 | M | 0 | 0 | 1 | — | 1 | 1 | 1 | 1 | 1 |
| 125 | M | 1 | 1 | 1 | — | 1 | 1 | 1 | 0 | 0 |
| 40 | M | 1 | 1 | 0 | — | 0 | — | 0 | 0 | 0 |
| 22 | P | 0 | 0 | 1 | 1 | 1 | 1 | 1 | 1 | 1 |

From CEPH 1333-04, we see that AA1 and YM29 must lie distal to Mfd191. From 13292, it can be inferred that both AA1 and ED2 are proximal to 4–7, YM29, and Mfd188. The recombinants found in K2082 provide some additional ordering information. Three independent observations (individual numbers 22, 40, & 63) place AA1, ED2, 4–7, and YM29, and Mfd188 distal to Mfd191, while ID 125 places 4–7, YM29, and Mfd188 proximal to SCG40. No genetic information on the relative ordering within the two clusters of markers AA1/ED2 and 4–7/YM29/Mfd188 was obtained from the genetic recombinant analysis. Although ordering loci with respect to hybrids which are known to contain "holes" in which small pieces of interstitial human DNA may be missing is problematic, the hybrid patterns indicate that 4–7 lies above both YM29 and Mfd188.

EXAMPLE 5

Genetic Analyses of Breast Cancer Kindreds with Markers AA1,4–7, ED2, and YM29

In addition to the three kindreds containing key recombinants which have been discussed previously, kindred K2039 was shown through analysis of the newly developed STR markers to be linked to the region and to contain a useful recombinant.

Table 8 defines the haplotypes (shown in coded form) of the kindreds in terms of specific marker alleles at each locus and their respective frequencies. In Table 8, alleles are listed in descending order of frequency; frequencies of alleles 1–5 for each locus are given in Table 5. Haplotypes coded H are BRCA1 associated haplotypes, P designates a partial H haplotype, and an R indicates an observable recombinant haplotype. As evident in Table 8, not all kindreds were typed for all markers; moreover, not all individuals within a kindred were typed for an identical set of markers, especially in K2082. With one exception, only haplotypes inherited from affected or at-risk kindred members are shown; haplotypes from spouses marrying into the kindred are not described. Thus in a given sibship, the appearance of haplotypes X and Y indicates that both haplotypes from the affected/at-risk individual were seen and neither was a breast cancer associated haplotype.

TABLE 8

Breast Cancer Linked Haplotypes Found in the Three Kindreds

| Kin. | HAP | Mfd15 | THRA1 | Mfd191 | tdj1475 | ED2 | AA1 | Z109 | CA375 | 4–7 | YM29 | Mfd188 | SCG40 | 6C1 | 42D6 |
|---|---|---|---|---|---|---|---|---|---|---|---|---|---|---|---|
| 1901 | H1 | 1 | 5 | 5 | 3 | 1 | 4 | NI | NI | 1 | 1 | 3 | NI | NI | 1 |
|  | R2 | 9 | 2 | 5 | 6 | 1 | 4 | NI | NI | 1 | 1 | 3 | NI | NI | 1 |
| 2082 | H1 | 3 | NI | 4 | 6 | 6 | 1 | NI | NI | 2 | 1 | 4 | 2 | NI | 1 |
|  | P1 | 3 | NI | 4 | NI | NI | NI | NI | NI | NI | NI | 4 | 2 | NI | 1 |
|  | P2 | 3 | NI | NI | NI | NI | NI | NI | NI | NI | NI | 4 | NI | NI | NI |
|  | R1 | 6 | NI | 1 | 5 | 6 | 1 | NI | NI | 2 | 1 | 4 | 2 | NI | 1 |
|  | R2 | 6 | NI | 4 | 6 | 6 | 1 | NI | NI | 2 | 1 | 4 | 2 | NI | 1 |
|  | R3 | 3 | NI | 4 | NI | 6 | 1 | NI | NI | 2 | 1 | 4 | 1 | NI | 7 |
|  | R4 | 7 | NI | 1 | NI | 1 | 5 | NI | NI | 4 | 6 | 1 | 2 | NI | 1 |
|  | R5 | 3 | NI | 4 | NI | NI | NI | NI | NI | NI | 2 | 1 | NI | NI | NI |
|  | R6 | 3 | NI | 4 | 3 | 1 | 2 | NI | NI | 1 | 2 | 2 | 6 | NI | 6 |

TABLE 8-continued

Breast Cancer Linked Haplotypes Found in the Three Kindreds

| Kin. | HAP | Mfd15 | THRA1 | Mfd191 | tdj1475 | ED2 | AA1 | Z109 | CA375 | 4–7 | YM29 | Mfd188 | SCG40 | 6C1 | 42D6 |
|---|---|---|---|---|---|---|---|---|---|---|---|---|---|---|---|
|  | R7 | 3 | NI | 4 | 3 | 7 | 1 | NI | NI | 1 | 1 | 3 | 7 | NI | 4 |
| 2035 | H1 | 8 | 2 | 1 | NI | 5 | 1 | 1 | 4 | 3 | 1 | 6 | 8 | 2 | 4 |
|  | H2 | 8 | 2 | 1 | NI | 5 | 1 | 1 | 2 | 1 | 1 | 2 | 3 | 1 | 4 |
|  | R2 | 8 | 2 | 1 | NI | 5 | 1 | 1 | 2 | 1 | 1 | 2 | 3 | 6 | 1 |

In kindred K1901, the new markers showed no observable recombination with breast cancer susceptibility, indicating that the recombination event in this kindred most likely took place between THRA1 and ED2. Thus, no new BRCA1 localization information was obtained based upon studying the four new markers in this kindred. In kindred 2082 the key recombinant individual has inherited the linked alleles for ED2, 4–7, AA1, and YM29, and was recombinant for tdj1474 indicating that the recombination event occurred in this individual between tdj1474 and ED2/AA1.

There are three haplotypes of interest in kindred K2035, H1, H2, and R2 shown in Table 8. H1 is present in the four cases and one obligate male carrier descendant from individual 17 while H2 is present or inferred in two cases and two obligate male carriers in descendants of individual 10. R2 is identical to H2 for loci between and including Mfd15 and SCG40, but has recombined between SCG40 and 42D6. Since we have established that BRCA1 is proximal to 42D6, this H2/R2 difference adds no further localization information. H1 and R2 share an identical allele at Mfd15, THRA1, AA1, and ED2 but differ for loci presumed distal to ED2, i.e., 4–7, Mfd188, SCG40, and 6C1. Although the two haplotypes are concordant for the 5th allele for marker YM29, a marker which maps physically between 4–7 and Mfd 188, it is likely that the alleles are shared identical by state rather than identical by descent since this allele is the most common allele at this locus with a frequency estimated in CEPH parents of 0.42. By contrast, the linked alleles shared at the Mfd15 and ED2 loci have frequencies of 0.04 and 0.09, respectively. They also share more common alleles at Mfd191 (frequency=0.52), THRA1, and AA1 (frequency=0.28). This is the key recombinant in the set as it is the sole recombinant in which breast cancer segregated with the proximal portion of the haplotype, thus setting the distal boundary. The evidence from this kindred therefore places the BRCA1 locus proximal to 4–7.

The recombination event in kindred 2082 which places BRCA1 distal to tdj1474 is the only one of the four events described which can be directly inferred; that is, the affected mother's genotype can be inferred from her spouse and offspring, and the recombinant haplotype can be seen in her affected daughter. In this family the odds in favor of affected individuals carrying BRCA1 susceptibility alleles are extremely high; the only possible interpretations of the data are that BRCA1 is distal to Mfd191 or alternatively that the purported recombinant is a sporadic case of ovarian cancer at age 44. Rather than a directly observable or inferred recombinant, interpretation of kindred 2035 depends on the observation of distinct 17q-haplotypes segregating in different and sometimes distantly related branches of the kindred. The observation that portions of these haplotypes have alleles in common for some markers while they differ at other markers places the BRCA1 locus in the shared region. The confidence in this placement depends on several factors: the relationship between the individuals carrying the respective haplotypes, the frequency of the shared allele, the certainty with which the haplotypes can be shown to segregate with the BRCA1 locus, and the density of the markers in the region which define the haplotype. In the case of kindred 2035, the two branches are closely related, and each branch has a number of early onset cases which carry the respective haplotype. While two of the shared alleles are common, (Mfd191, THRA1), the estimated frequencies of the shared alleles at Mfd15, AA1, and ED2 are 0.04, 0.28, and 0.09, respectively. It is therefore highly likely that these alleles are identical by descent (derived from a common ancestor) rather than identical by state (the same allele but derived from the general population).

EXAMPLE 6

Refined Physical Mapping Studies Place the BRCA1 Gene in a Region Flanked by tdj1474 and U5R Since its initial localization to chromosome 17q in 1990 (Hall et al., 1990) a great deal of effort has gone into localizing the BRCA1 gene to a region small enough to allow implementation of effective positional cloning strategies to isolate the gene. The BRCA1 locus was first localized to the interval Mfd15 (D17S250)–42D6 (D17S588) by multipoint linkage analysis (Easton et al., 1993) in the collaborative Breast Cancer Linkage Consortium dataset consisting of 214 families collected worldwide. Subsequent refinements of the localization have been based upon individual recombinant events in specific families. The region THRA1–D17S183 was defined by Bowcock et al., 1993; and the region THRA1–D17S78 was defined by Simard et al., 1993.

We further showed that the BRCA1 locus must lie distal to the marker Mfd191 (D17S776) (Goldgar et al., 1994). This marker is known to lie distal to THRA1 and RARA. The smallest published region for the BRCA1 locus is thus between D17S776 and D17S78. This region still contains approximately 1.5 million bases of DNA, making the isolation and testing of all genes in the region a very difficult task. We have therefore undertaken the tasks of constructing a physical map of the region, isolating a set of polymorphic STR markers located in the region, and analyzing these new markers in a set of informative families to refine the location of the BRCA1 gene to a manageable interval.

Four families provide important genetic evidence for localization of BRCA1 to a sufficiently small region for the application of positional cloning strategies. Two families (K2082, K1901) provide data relating to the proximal boundary for BRCA1 and the other two (K2035, K1813) fix the distal boundary. These families are discussed in detail below. A total of 15 Short Tandem Repeat markers assayable by PCR were used to refine this localization in the families studied. These markers include DS17S7654, DS17S975, tdj1474, and tdj1239. Primer sequences for these markers are provided in SEQ ID NO:3 and SEQ ID NO:4 for DS17S754; in SEQ ID NO:5 and SEQ ID NO:6 for DS17S975; in SEQ ID NO:7 and SEQ ID NO:8 for tdj1474; and, in SEQ ID NO:9 and SEQ ID NO:10 for tdj1239.

Kindred 2082

Kindred 2082 is the largest BRCA1-linked breast/ovarian cancer family studied to date. It has a LOD score of 8.6, providing unequivocal evidence for 17q linkage. This family has been previously described and shown to contain a critical recombinant placing BRCA1 distal to MFD191 (D17S776). This recombinant occurred in a woman diagnosed with ovarian cancer at age 45 whose mother had ovarian cancer at age 63. The affected mother was deceased; however, from her children, she could be inferred to have the linked haplotype present in the 30 other linked cases in the family in the region between Mfd15 and Mfd188. Her affected daughter received the linked allele at the loci ED2, 4-7, and Mfd188, but received the allele on the non-BRCA1 chromosome at Mfd15 and Mfd91. In order to further localize this recombination breakpoint, we tested DNA from the key members of this family for the following markers derived from physical mapping resources: tdj1474, tdj1239, CF4, D17S855. For the markers tdj1474 and CF4, the affected daughter did not receive the linked allele. For the STR locus tdj1239, however, the mother could be inferred to be informative and her daughter did receive the BRCA1-associated allele. D17S855 was not informative in this family. Based on this analysis, the order is 17q centromere-Mfd191-17HSD-CF4-tdj1474-tdj1239-D17S855-ED2-4-7-Mfd188-17q telomere. The recombinant described above therefore places BRCA1 distal to tdj1474, and the breakpoint is localized to the interval between tdj1474 and tdj1239. The only alternative explanation for the data in this family other than that of BRCA1 being located distal to tdj1474, is that the ovarian cancer present in the recombinant individual is caused by reasons independent of the BRCA1 gene. Given that ovarian cancer diagnosed before age 50 is rare, this alternate explanation is exceedingly unlikely.

Kindred 1901

Kindred 1901 is an early-onset breast cancer family with 7 cases of breast cancer diagnosed before 50, 4 of which were diagnosed before age 40. In addition, there were three cases of breast cancer diagnosed between the ages of 50 and 70. One case of breast cancer also had ovarian cancer at age 61. This family currently has a LOD score of 1.5 with D17S855. Given this linkage evidence and the presence of at lease one ovarian cancer case, this family has a posterior probability of being due to BRCA1 of over 0.99. In this family, the recombination comes from the fact that an individual who is the brother of the ovarian cancer case from which the majority of the other cases descend, only shares a portion of the haplotype which is cosegregating with the other cases in the family. However, he passed this partial haplotype to his daughter who developed breast cancer at age 44. If this case is due to the BRCA1 gene, then only the part of the haplotype shared between this brother and his sister can contain the BRCA1 gene. The difficulty in interpretation of this kind of information is that while one can be sure of the markers which are not shared and therefore recombinant, markers which are concordant can either be shared because they are non-recombinant, or because their parent was homozygous. Without the parental genotypic data it is impossible to discriminate between these alternatives. Inspection of the haplotype in K1901, shows that he does not share the linked allele at Mfd15 (D17S250), THRA1, CF4 (D17S1320), and tdj1474 (17DS1321). He does share the linked allele at Mfd191 (D17S776), ED2 (D17S1327), tdj1239 (D17S1328), and Mfd188 (D17S579). Although the allele shared at Mfd191 is relatively rare (0.07), we would presume that the parent was homozygous since they are recombinant with markers located nearby on either side, and a double recombination event in this region would be extremely unlikely. Thus the evidence in this family would also place the BRCA1 locus distal to tdj474. However, the lower limit of this breakpoint is impossible to determine without parental genotype information. It is intriguing that the key recombinant breakpoint in this family confirms the result in Kindred 2082. As before, the localization information in this family is only meaningful if the breast cancer was due to the BRCA1 gene. However, her relatively early age at diagnosis (44) makes this seem very likely since the risk of breast cancer before age 45 in the general population is low (approximately 1%).

Kindred 2035

This family is similar to K1901 in that the information on the critical recombinant events is not directly observed but is inferred from the observation that the two haplotypes which are cosegregating with the early onset breast cancer in the two branches of the family appear identical for markers located in the proximal portion of the 17q BRCA1 region but differ at more distal loci. Each of these two haplotypes occurs in at least four cases of early-onset or bilateral breast cancer. The overall LOD score with ED2 in this family is 2.2, and considering that there is a case of ovarian cancer in the family (indicating a prior probability of BRCA1 linkage of 80%), the resulting posterior probability that this family is linked to BRCA1 is 0.998. The haplotypes are identical for the markers Mfd15, THRA1, Mfd191, ED2, AA1, D17S858 and D17S902. The common allele at Mfd15 and ED2 are both quite rare, indicating that this haplotype is shared identical by descent. The haplotypes are discordant, however, for CA375, 4-7, and Mfd188, and several more distal markers. This indicates that the BRCA1 locus must lie above the marker CA-375. This marker is located approximately 50 kb below D17S78, so it serves primarily as additional confirmation of this previous lower boundary as reported in Simard et al. (1993).

Kindred 1813

Kindred 1813 is a small family with four cases of breast cancer diagnosed at very early ages whose mother also had breast cancer diagnosed at an early age and ovarian cancer some years later. This family yields a maximum multipoint LOD score of 0.60 with 17q markers and, given that there is at least one case of ovarian cancer, results in a posterior probability of being a BRCA1 linked family of 0.93. This family contains a directly observable recombination event in individual 18 (see FIG. 5 in Simard et al., *Human Mol. Genet.* 2:1193-1199 (1993)), who developed breast cancer at age 34. The genotype of her affected mother at the relevant 17q loci can be inferred from her genotypes, her affected sister's genotypes, and the genotypes of three other unaffected siblings. Individual 18 inherits the BRCA1-linked alleles for the following loci: Mfd15, THRA1, D17S800, D17S855, AA1, and D17S931. However, for markers below D17S931, i.e., U5R, vrs31, D17S858, and D17S579, she has inherited the alleles located on the non-disease bearing chromosome. The evidence from this family therefore would place the BRCA1 locus proximal to the marker U5R. Because of her early age at diagnosis (34) it is extremely unlikely that the recombinant individual's cancer is not due to the gene responsible for the other cases of breast/ovarian cancer in this family; the uncertainty in this family comes from our somewhat smaller amount of evidence that breast cancer in this family is due to BRCA1 rather than a second, as yet unmapped, breast cancer susceptibility locus.

Size of the region containing BRCA1

Figure 2:
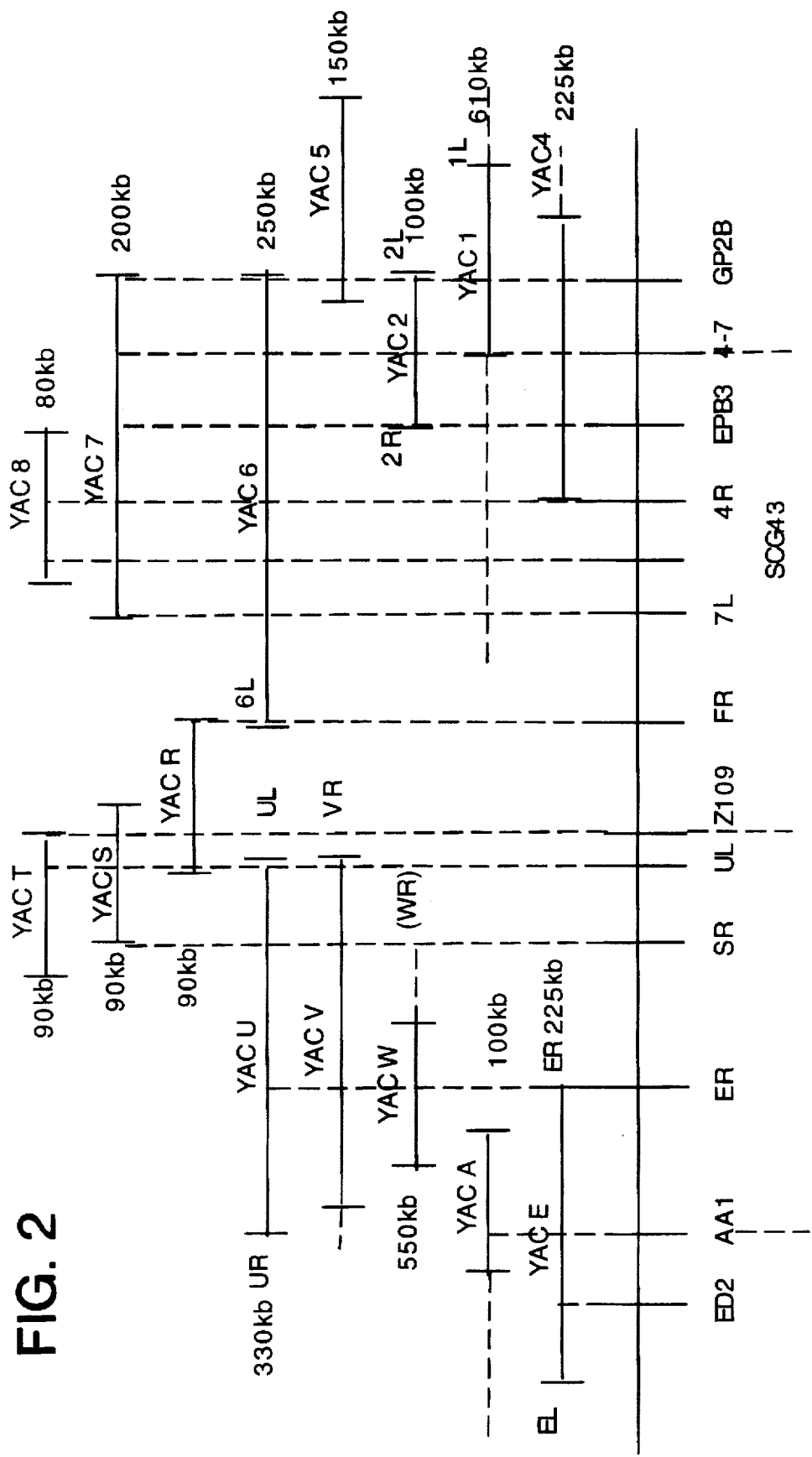
FIG. 2 is a schematic map of YACs which define part of Mfd15-Mfd188 region.

Based on the genetic data described in detail above, the BRCA1 locus must lie in the interval between the markers tdj1474 and U5R, both of which were isolated in our laboratory. Based upon the physical maps shown in FIGS. 2 and 3, we can try to estimate the physical distance between these two loci. It takes approximately 14 P1 clones with an average insert size of approximately 80 kb to span the region. However, because all of these P1s overlap to some unknown degree, the physical region is most likely much smaller than 14 times 80 kb. Based on restriction maps of the clones covering the region, we estimate the size of the region containing BRCA1 to be approximately 650 kb.

EXAMPLE 7

Identification of Candidate cDNA Clones for the BRCA1 Locus by Genomic Analysis of the Contig Region Complete screen of the plausible region. The first method to identify candidate cDNAs, although labor intensive, used known techniques. The method comprised the screening of cosmids and P1 and BAC clones in the contig to identify putative coding sequences. The clones containing putative coding sequences were then used as probes on filters of cDNA libraries to identify candidate cDNA clones for future analysis. The clones were screened for putative coding sequences by either of two methods.

Zoo blots. The first method for identifying putative coding sequences was by screening the cosmid and P1 clones for sequences conserved through evolution across several species. This technique is referred to as "zoo blot analysis" and is described by Monaco, 1986. Specifically, DNAs from cow, chicken, pig, mouse and rat were digested with the restriction enzymes EcoRi and HindIII (8 µg of DNA per enzyme). The digested DNAs were separated overnight on an 0.7% gel at 20 volts for 16 hours (14 cm gel), and the DNA transferred to Nylon membranes using standard Southern blot techniques. For example, the zoo blot filter was treated at 65° C. in 0.1× SSC, 0.5% SDS, and 0.2M Tris, pH 8.0, for 30 minutes and then blocked overnight at 42° C. in 5× SSC, 10% PEG 8000, 20 mM NaPO$_4$ pH 6.8, 100 µg/ml Salmon Sperm DNA, 1x Denhardt's, 50% formamide, 0.1% SDS, and 2 µg/ml C$_o$t-1 DNA.

The cosmid and P1 clones to be analyzed were digested with a restriction enzyme to release the human DNA from the vector DNA. The DNA was separated on a 14 cm, 0.5% agarose gel run overnight at 20 volts for 16 hours. The human DNA bands were cut out of the gel and electroeluted from the gel wedge at 100 volts for at least two hours in 0.5× Tris Acetate buffer (Maniatis et al., 1982). The eluted Not I digested DNA (~15 kb to 25 kb) was then digested with EcoRI restriction enzyme to give smaller fragments (~0.5 kb to 5.0 kb) which melt apart more easily for the next step of labeling the DNA with radionucleotides. The DNA fragments were labeled by means of the hexamer random prime labeling method (Boehringer-Mannheim, Cat. #1004760). The labeled DNA was spermine precipitated (add 100 µl TE, 5 µl 0.1M spermine, and 5 µl of 10 mg/ml salmon sperm DNA) to remove unincorporated radionucleotides. The labeled DNA was then resuspended in 100 µl TE, 0.5M NaCl at 65° C. for 5 minutes and then blocked with Human C$_o$t-1 DNA for 2–4 hrs. as per the manufacturer's instructions (Gibco/BRL, Cat. #5279SA). The C$_o$t-1 blocked probe was incubated on the zoo blot filters in the blocking solution overnight at 42° C. The filters were washed for 30 minutes at room temperature in 2× SSC, 0.1% SDS, and then in the same buffer for 30 minutes at 55° C. The filters were then exposed 1 to 3 days at −70° C. to Kodak XAR-5 film with an intensifying screen. Thus, the zoo blots were hybridized with either the pool of Eco-R1 fragments from the insert, or each of the fragments individually.

HTF island analysis. The second method for identifying cosmids to use as probes on the cDNA libraries was HTF island analysis. Since the pulsed-field map can reveal HTF islands, cosmids that map to these HTF island regions were analyzed with priority. HTF islands are segments of DNA which contain a very high frequency of unmethylated CpG dinucleotides (Tonolio et al., 1990) and are revealed by the clustering of restriction sites of enzymes whose recognition sequences include CpG dinucleotides. Enzymes known to be useful in HTF-island analysis are AscI, NotI, BssHII, EagI, SacII, NaeI, NarI, SmaI, and MluI (Anand, 1992). A pulsed-field map was created using the enzymes NotI, NruI, EagI, SacII, and SalI, and two HTF islands were found. These islands are located in the distal end of the region, one being distal to the GP2B locus, and the other being proximal to the same locus, both outside the BRCA1 region. The cosmids derived from the YACs that cover these two locations were analyzed to identify those that contain these restriction sites, and thus the HTF islands.

cDNA screening. Those clones that contain HTF islands or show hybridization to other species DNA besides human are likely to contain coding sequences. The human DNA from these clones was isolated as whole insert or as EcoR1 fragments and labeled as described above. The labeled DNA was used to screen filters of various cDNA libraries under the same conditions as the zoo blots except that the cDNA filters undergo a more stringent wash of 0.1× SSC, 0.1% SDS at 65° C. for 30 minutes twice.

Most of the cDNA libraries used to date in our studies (libraries from normal breast tissue, breast tissue from a woman in her eighth month of pregnancy and a breast malignancy) were prepared at Clonetech, Inc. The cDNA library generated from breast tissue of an 8 month pregnant woman is available from Clonetech (Cat. #HL1037a) in the Lambda gt-10 vector, and is grown in C600Hfl bacterial host cells. Normal breast tissue and malignant breast tissue samples were isolated from a 37 year old Caucasian female and one-gram of each tissue was sent to Clonetech for mRNA processing and cDNA library construction. The latter two libraries were generated using both random and oligo-dT priming, with size selection of the final products which were then cloned into the Lambda Zap II vector, and grown in XL1-blue strain of bacteria as described by the manufacturer. Additional tissue-specific cDNA libraries include human fetal brain (Stratagene, Cat. 936206), human testis (Clonetech Cat. HL3024), human thymus (Clonetech Cat. HL 1127n), human brain (Clonetech Cat. HL11810), human placenta (Clonetech Cat 1075b), and human skeletal muscle (Clonetech Cat. HL1124b).

The cDNA libraries were plated with their host cells on NZCYM plates, and filter lifts are made in duplicate from each plate as per Maniatis et al. (1982). Insert (human) DNA from the candidate genomic clones was purified and radioactively labeled to high specific activity. The radioactive DNA was then hybridized to the cDNA filters to identify those cDNAs which correspond to genes located within the candidate cosmid clone. cDNAs identified by this method were picked, replated, and screened again with the labeled clone insert or its derived EcoR1 fragment DNA to verify their positive status. Clones that were positive after this second round of screening were then grown up and their DNA purified for Southern blot analysis and sequencing.

Clones were either purified as plasmid through in vivo excision of the plasmid from the Lambda vector as described in the protocols from the manufacturers, or isolated from the Lambda vector as a restriction fragment and subcloned into plasmid vector.

The Southern blot analysis was performed in duplicate, one using the original genomic insert DNA as a probe to verify that cDNA insert contains hybridizing sequences. The second blot was hybridized with cDNA insert DNA from the largest cDNA clone to identify which clones represent the same gene. All cDNAs which hybridize with the genomic clone and are unique were sequenced and the DNA analyzed to determine if the sequences represent known or unique genes. All cDNA clones which appear to be unique were further analyzed as candidate BRCA1 loci. Specifically, the clones are hybridized to Northern blots to look for breast specific expression and differential expression in normal versus breast tumor RNAs. They are also analyzed by PCR on clones in the BRCA1 region to verify their location. To map the extent of the locus, full length cDNAs are isolated and their sequences used as PCR probes on the YACs and the clones surrounding and including the original identifying clones. Intron-exon boundaries are then further defined through sequence analysis.

We have screened the normal breast, 8 month pregnant breast and fetal brain cDNA libraries with zoo blot-positive Eco R1 fragments from cosmid BAC and P1 clones in the region. Potential BRCA1 cDNA clones were identified among the three libraries. Clones were picked, replated, and screened again with the original probe to verify that they were positive.

Analysis of hybrid-selected cDNA. cDNA fragments obtained from direct selection were checked by Southern blot hybridization against the probe DNA to verify that they originated from the contig. Those that passed this test were sequenced in their entirety. The set of DNA sequences obtained in this way were then checked against each other to find independent clones that overlapped. For example, the clones 694-65, 1240-1 and 1240-33 were obtained independently and subsequently shown to derive from the same contiguous cDNA sequence which has been named EST:489:1.

Analysis of candidate clones. One or more of the candidate genes generated from above were sequenced and the information used for identification and classification of each expressed gene. The DNA sequences were compared to known genes by nucleotide sequence comparisons and by translation in all frames followed by a comparison with known amino acid sequences. This was accomplished using Genetic Data Environment (GDE) version 2.2 software and the Basic Local Alignment Search Tool (Blast) series of client/server software packages (e.g., BLASTN 1.3.1 3MP), for sequence comparison against both local and remote sequence databases (e.g., GenBank), running on Sun SPARC workstations. Sequences reconstructed from collections of cDNA clones identified with the cosmids and P1 s have been generated. All candidate genes that represented new sequences were analyzed further to test their candidacy for the putative BRCA1 locus.

Mutation screening. To screen for mutations in the affected pedigrees, two different approaches were followed. First, genomic DNA isolated from family members known to carry the susceptibility allele of BRCA1 was used as a template for amplification of candidate gene sequences by PCR. If the PCR primers flank or overlap an intron/exon boundary, the amplified fragment will be larger than predicted from the cDNA sequence or will not be present in the amplified mixture. By a combination of such amplification experiments and sequencing of P1, BAC or cosmid clones using the set of designed primers it is possible to establish the intron/exon structure and ultimately obtain the DNA sequences of genomic DNA from the pedigrees.

A second approach that is much more rapid if the intron/exon structure of the candidate gene is complex involves sequencing fragments amplified from pedigree lymphocyte cDNA. CDNA synthesized from lymphocyte mRNA extracted from pedigree blood was used as a substrate for PCR amplification using the set of designed primers. If the candidate gene is expressed to a significant extent in lymphocytes, such experiments usually produce amplified fragments that can be sequenced directly without knowledge of intron/exon junctions.

The products of such sequencing reactions were analyzed by gel electrophoresis to determine positions in the sequence that contain either mutations such as deletions or insertions, or base pair substitutions that cause amino acid changes or other detrimental effects.

Any sequence within the BRCA1 region that is expressed in breast is considered to be a candidate gene for BRCA1. Compelling evidence that a given candidate gene corresponds to BRCA1 comes from a demonstration that pedigree families contain defective alleles of the candidate.

EXAMPLE 8

Identification of BRCA1

Identification of BRCA1. Using several strategies, a detailed map of transcripts was developed for the 600 kb region of 17q21 between D17S1321 and D17S1324. Candidate expressed sequences were defined as DNA sequences obtained from: 1) direct screening of breast, fetal brain, or lymphocyte cDNA libraries, 2) hybrid selection of breast, lymphocyte or ovary cDNAs, or 3) random sequencing of genomic DNA and prediction of coding exons by XPOUND (Thomas and Skolnick, 1994). These expressed sequences in many cases were assembled into contigs composed of several independently identified sequences. Candidate genes may comprise more than one of these candidate expressed sequences. Sixty-five candidate expressed sequences within this region were identified by hybrid selection, by direct screening of cDNA libraries, and by random sequencing of P1 subclones. Expressed sequences were characterized by transcript size, DNA sequence, database comparison, expression pattern, genomic structure, and, most importantly, DNA sequence analysis in individuals from kindreds segregating 17q-linked breast and ovarian cancer susceptibility.

Figures 4, 5:
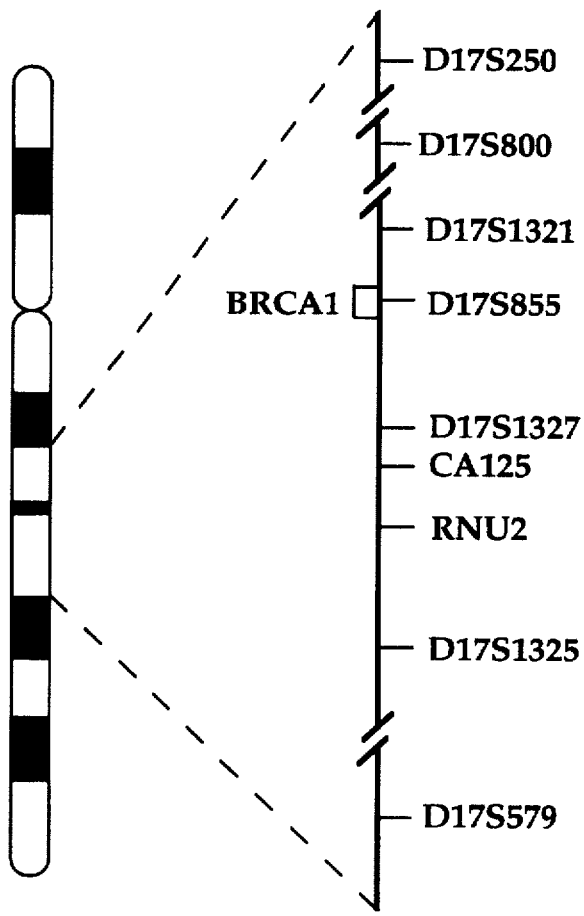
FIG. 4 is a schematic map of human chromosome 17. The pertinent region containing BRCA1 is expanded to indicate the relative positions of two previously identified genes, CA125 and RNU2. BRCA1 spans the marker D17S855.
FIG. 5 shows alignment of the BRCA1 zinc-finger domain with 3 other zinc-finger domains that scored highest in a Smith-Waterman alignment. RPT1 encodes a protein that appears to be a negative regulator of the IL-2 receptor in mouse. RIN1 encodes a DNA-binding protein that includes a RING-finger motif related to the zinc-finger. RFP1 encodes a putative transcription factor that is the N-terminal domain of the RET oncogene product. The bottom line contains the C3HC4 consensus zinc-finger sequence showing the positions of cysteines and one histidine that form the zinc ion binding pocket.

Three independent contigs of expressed sequence, 1141:1 (649 bp), 694:5 (213 bp) and 754:2 (1079 bp) were isolated and eventually shown to represent portions of BRCA1. When ESTs for these contigs were used as hybridization probes for Northern analysis, a single transcript of approximately 7.8 kb was observed in normal breast mRNA, suggesting that they encode different portions of a single gene. Screens of breast, fetal brain, thymus, testes, lymphocyte and placental cDNA libraries and PCR experiments with breast mRNA linked the 1141:1, 694:5 and 754:2 contigs. 5' RACE experiments with thymus, testes, and breast mRNA extended the contig to the putative 5' end, yielding a composite full length sequence. PCR and direct sequencing of P1s and BACs in the region were used to identify the location of introns and allowed the determination of splice donor and acceptor sites. These three expressed sequences were merged into a single transcription unit that proved in the final analysis to be BRCA1. This transcription unit is located adjacent to D17S855 in the center of the 600 kb region (FIG. 4).

Figure 6:
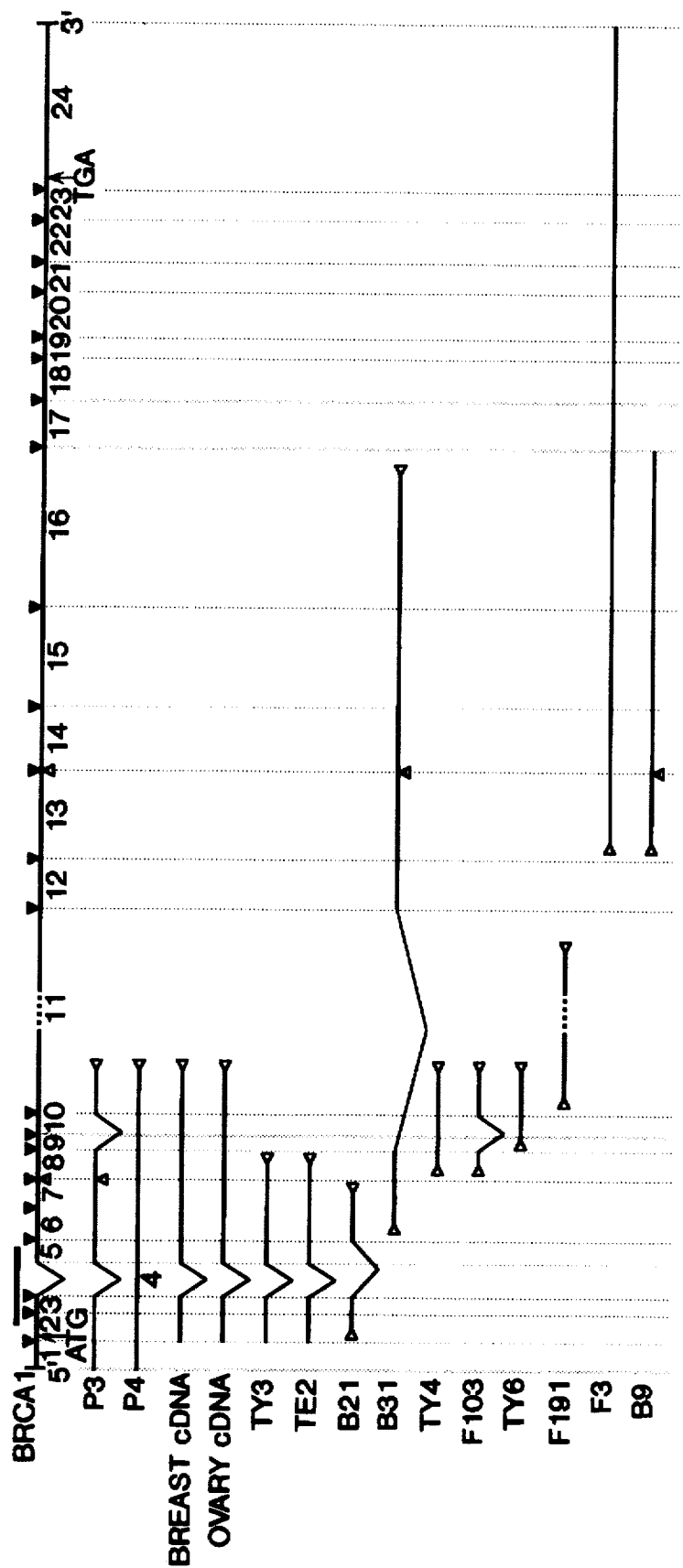
FIG. 6 is a diagram of BRCA1 mRNA showing the locations of introns and the variants of BRCA1 mRNA produced by alternative splicing. Intron locations are shown by dark triangles and the exons are numbered below the line representing the cDNA. The top cDNA is the composite used to generate the peptide sequence of BRCA1. Alternative forms identified as cDNA clones or hybrid selection clones are shown below.
Figure 7:
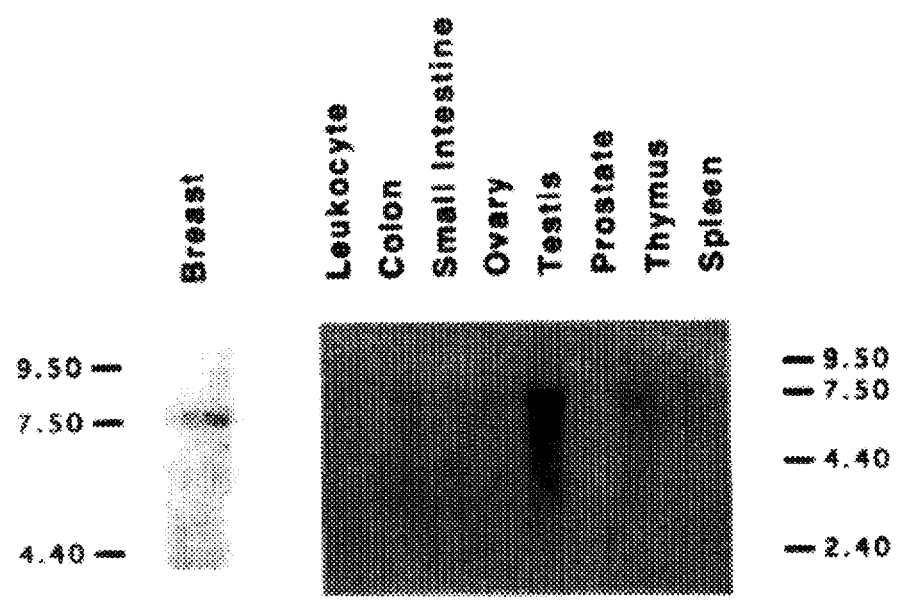
FIG. 7 shows the tissue expression pattern of BRCA1. The blot was obtained from Clontech and contains RNA from the indicated tissues. Hybridization conditions were as recommended by the manufacturer using a probe consisting of nucleotide positions 3631 to 3930 of BRCA1. Note that both breast and ovary are heterogeneous tissues and the percentage of relevant epithelial cells can be variable. Molecular weight standards are in kilobases.

Combination of sequences obtained from cDNA clones, hybrid selection sequences, and amplified PCR products allowed construction of a composite full length BRCA1 cDNA (SEQ ID NO:1). The sequence of the BRCA1 cDNA (up through the stop codon) has also been deposited with GenBank and assigned accession number U-14680. This deposited sequence is incorporated herein by reference. The cDNA clone extending farthest in the 3' direction contains a poly(A) tract preceded by a polyadenylation signal. Conceptual translation of the cDNA revealed a single long open reading frame of 208 kilodaltons (amino acid sequence: SEQ ID NO:2) with a potential initiation codon flanked by sequences resembling the Kozak consensus sequence (Kozak, 1987). Smith-Waterman (Smith and Waterman, 1981) and BLAST (Altschul et al., 1990) searches identified a sequence near the amino terminus with considerable homology to zinc-finger domains (FIG. 5). This sequence contains cysteine and histidine residues present in the consensus C3HC4 zinc-finger motif and shares multiple other residues with zinc-finger proteins in the databases. The BRCA1 gene is composed of 23 coding exons arrayed over more than 100 kb of genomic DNA (FIG. 6). Northern blots using fragments of the BRCA1 cDNA as probes identified a single transcript of about 7.8 kb, present most abundantly in breast, thymus and testis, and also present in ovary (FIG. 7). Four alternatively spliced products were observed as independent cDNA clones; 3 of these were detected in breast and 2 in ovary mRNA (FIG. 6). A PCR survey from tissue cDNAs further supports the idea that there is considerable heterogeneity near the 5' end of transcripts from this gene; longest deletion being 1,155 bp. The predominant form of the BRCA1 protein in breast and ovary lacks exon 4. The nucleotide sequence for BRCA1 exon 4 is shown in SEQ ID NO:11, with the predicted amino acid sequence shown in SEQ ID NO:12.

Figure 8:
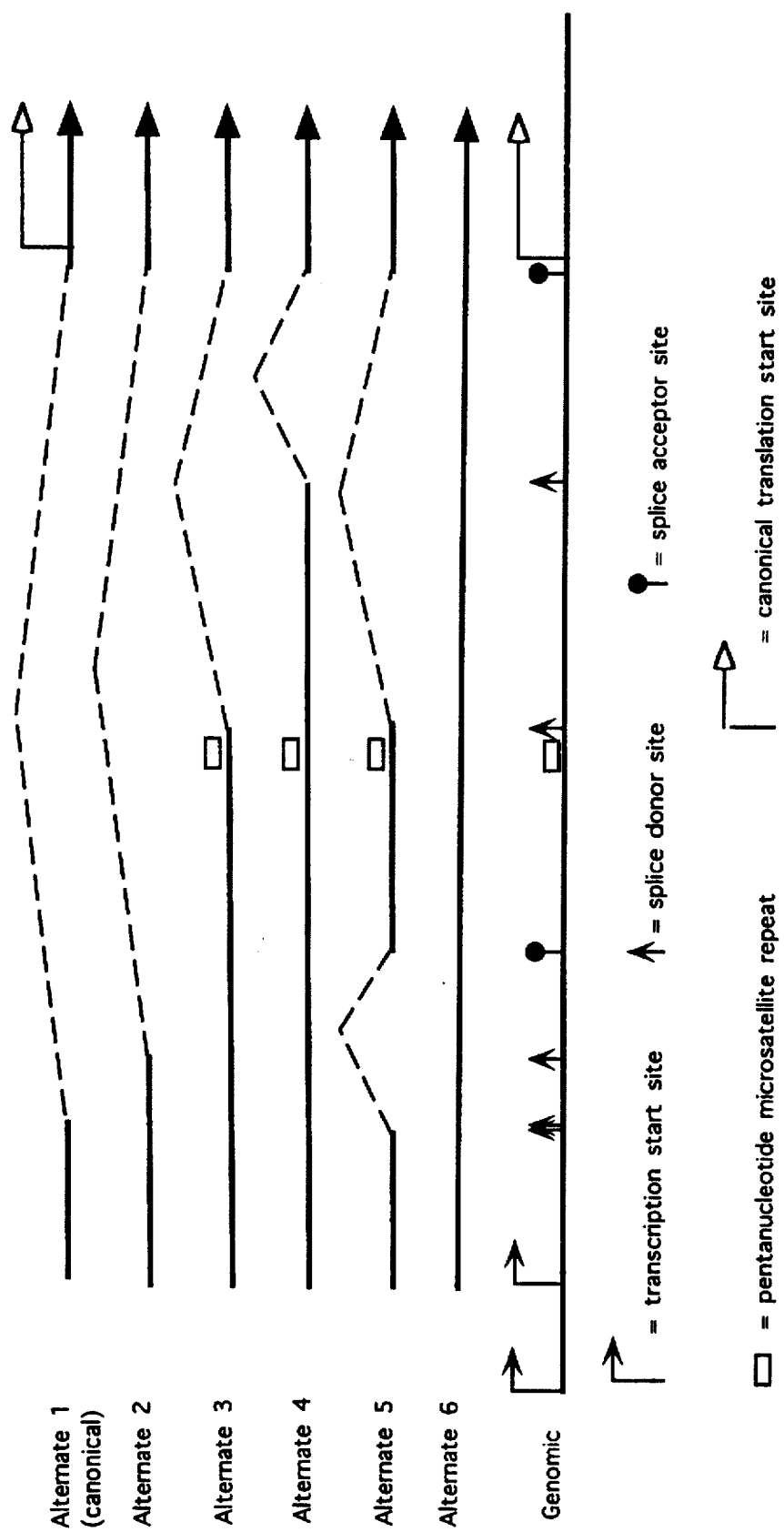
FIG. 8 is a diagram of the 5' untranslated region plus the beginning of the translated region of BRCA1 showing the locations of introns and the variants of BRCA1 mRNA produced by alternative splicing. Intron locations are shown by broken dashed lines. Six alternate splice forms are shown.

Additional 5' sequence of BRCA1 genomic DNA is set forth in SEQ ID NO:13. The G at position 1 represents the potential start site in testis. The A in position 140 represents the potential start site in somatic tissue. There are six alternative splice forms of this 5' sequence as shown in FIG. 8. The G at position 356 represents the canonical first splice donor site. The G at position 444 represents the first splice donor site in two clones (testis 1 and testis 2). The G at position 889 represents the first splice donor site in thymus 3. A fourth splice donor site is the G at position 1230. The T at position 1513 represents the splice acceptor site for all of the above splice donors. A fifth alternate splice form has a first splice donor site at position 349 with a first acceptor site at position 591 and a second splice donor site at position 889 and a second acceptor site at position 1513. A sixth alternate form is unspliced in this 5' region. The A at position 1532 is the canonical start site, which appears at position 120 of SEQ ID NO:1. Partial genomic DNA sequences determined for BRCA1 are set forth in FIGS. 10A–10H and SEQ ID Numbers:14–34. The lower case letters (in FIGS. 10A–10H) denote intron sequence while the upper case letters denote exon sequence. Indefinite intervals within introns are designated with vvvvvvvvvvvvv in FIGS. 10A–10H. The intron/exon junctions are shown in Table 9. The CAG found at the 5' end of exons 8 and 14 is found in some cDNAs but not in others. Known polymorphic sites are shown in FIGS. 10A–10H in boldface type and are underlined.

TABLE 9

| Exon No. | Base Position* 5' | 3' | Length | Intron Borders 5' | 3' |
|---|---|---|---|---|---|
| e1 | 1 | 100 | 100 | GATAAATTAAAACTGCGACTGCGCGGCGTG[35]* | GTAGTAGAGTCCCGGGAAAGGGACAGGGGG[36] |
| e2 | 101 | 199 | 99 | ATATATATATGTTTTTCTAATGTGTTAAAG[37] | GTAAGTCAGCACAAGAGTGTATTAATTTGG[38] |
| e3 | 200 | 253 | 54 | TTTCTTTTTCTCCCCCCCCTACCCTGCTAG[39] | GTAAGTTTGAATGTGTTATGTGGCTCCATT[40] |
| e4 | *** | *** | 111 | AGCTACTTTTTTTTTTTTTTTTTTGAGACAG[41] | GTAAGTGCACACCACCATATCCAGCTAAAT[42] |
| e5 | 254 | 331 | 78 | AATTGTTCTTTCTTTCTTTATAATTTATAG[43] | GTATATAATTTGGTAATGATGCTAGGTTGG[44] |
| e6 | 332 | 420 | 89 | GAGTGTGTTTCTCAAACAATTTAATTTCAG[45] | GTAAGTGTTGAATATCCCAAGAATCACACT[46] |
| e7 | 421 | 560 | 140 | AAACATAATGTTTTCCCTTGTATTTTACAG[47] | GTAAAACCATTTGTTTTCTTCTTCTTCTTC[48] |
| e8 | 561 | 666 | 106 | TGCTTGACTGTTCTTTACCATACTGTTTAG[49] | GTAAGGGTCTCAGGTTTTTTAAGTATTTAA[50] |
| e9 | 667 | 712 | 46 | TGATTTATTTTTTGGGGGGAAATTTTTTAG[51] | GTGAGTCAAAGAGAACCTTTGTCTATGAAG[52] |
| e10 | 713 | 789 | 77 | TCTTATTAGGACTCTGTCTTTTCCCTATAG[53] | GTAATGGCAAAGTTTGCCAACTTAACAGGC[54] |
| e11 | 790 | 4215 | 3426 | GAGTACCTTGTTATTTTTGTATATTTTCAG[55] | GTATTGGAACCAGGTTTTTGTGTTTGCCCC[56] |
| e12 | 4216 | 4302 | 87 | ACATCTGAACCTCTGTTTTTGTTATTTAAG[57] | AGGTAAAAAGCGTGTGTGTGTGTGCACATG[58] |
| e13 | 4303 | 4476 | 174 | CATTTTCTTGGTACCATTTATCGTTTTTGA[59] | GTGTGTATTGTTGGCCAAACACTGATATCT[60] |
| e14 | 4477 | 4603 | 127 | AGTAGATTTGTTTTCTCATTCCATTTAAAG[61] | GTAAGAAACATCAATGTAAAGATGCTGTGG[62] |
| e15 | 4604 | 4794 | 191 | ATGGTTTTCTCCTTCCATTTATCTTTCTAG[63]** | GTAATATTTCATCTGCTGTATTGGAACAAA[64] |
| e16 | 4795 | 5105 | 311 | TGTAAATTAAACTTCTCCCATTCCTTTCAG[65] | GTGAGTGTATCCATATGTATCTCCCTAATG[66] |
| e17 | 5106 | 5193 | 88 | ATGATAATGGAATATTTGATTTAATTTCAG[67] | GTATACCAAGAACCTTTACAGAATACCTTG[68] |
| e18 | 5194 | 5271 | 78 | CTAATCCTTTGAGTGTTTTTCATTCTGCAG[69] | GTAAGTATAATACTATTTCTCCCCTCCTCC[70] |
| e19 | 5272 | 5312 | 41 | TGTAACCTGTCTTTTCTATGATCTCTTTAG[71] | GTAAGTACTTGATGTTACAAACTAACCAGA[72] |
| e20 | 5313 | 5396 | 84 | TCCTGATGGGTGTGTTTGGTTTCTTTCAG[73] | GTAAAGCTCCCTCCCTCAAGTTGACAAAAA[74] |
| e21 | 5397 | 5451 | 55 | CTGTCCCTCTCTCTTCCTCTCTTCTTCCAG[75] | GTAAGAGCCTGGGAGAACCCCAGAGTTCCA[76] |
| e22 | 5452 | 5525 | 74 | AGTGATTTACATGTAAATGTCCATTTTAG[77] | GTAAGTATTGGGTGCCCTGTCAGTGTGGGA[78] |
| e23 | 5526 | 5586 | 61 | TTGAATGCTCTTTCCTTCCTGGGGATCCAG[79] | GTAAGGTGCCTCGCATGTACCTGTGCTATT[80] |
| e24 | 5587 | 5914 | 328 | CTAATCTCTGCTTGTGTTCTCTGTCTCCAG[81] | |

*Base numbers in SEQ ID NO: 1.
**Numbers in superscript refer to SEQ ID NOS.
***e4 from SEQ ID NO: 11.

the molecular basis for the heterogeneity involves differential choice of the first splice donor site, and the changes detected all alter the transcript in the region 5' of the identified start codon. We have detected six potential alternate splice donors in this 5' untranslated region, with the Low stringency blots in which genomic DNA from organisms of diverse phylogenetic background were probed with BRCA1 sequences that lack the zinc-finger region revealed strongly hybridizing fragments in human, monkey, sheep and pig, and very weak hybridization signals in rodents. This result indicates that, apart from the zinc-finger domain, BRCA1 is conserved only at a moderate level through evolution.

Germline BRCA1 mutations in 17q-linked kindreds. The most rigorous test for BRCA1 candidate genes is to search for potentially disruptive mutations in carrier individuals from kindreds that segregate 17q-linked susceptibility to breast and ovarian cancer. Such individuals must contain BRCA1 alleles that differ from the wildtype sequence. The set of DNA samples used in this analysis consisted of DNA from individuals representing 8 different BRCA1 kindreds (Table 10).

TABLE 10

KINDRED DESCRIPTIONS AND ASSOCIATED LOD SCORES

| Kindred | Cases (n) Br | Br < 50 | Ov | Sporadic Cases[1] (n) | LOD Score | Markers(s) |
|---|---|---|---|---|---|---|
| 2082 | 31 | 20 | 22 | 7 | 9.49 | D17S1327 |
| 2099 | 22 | 14 | 2* | 0 | 2.36 | D17S800/D17S855[2] |
| 2035 | 10 | 8 | 1* | 0 | 2.25 | D17S1327 |
| 1901 | 10 | 7 | 1* | 0 | 1.50 | D17S855 |
| 1925 | 4 | 3 | 0 | 0 | 0.55 | D17S579 |
| 1910 | 5 | 4 | 0 | 0 | 0.36 | D17S579/D17S250[2] |
| 1927 | 5 | 4 | 0 | 1 | −0.44 | D17S250 |
| 1911 | 8 | 5 | 0 | 2 | −0.20 | D17S250 |

[1]Number of women with breast cancer (diagnosed under age 50) or ovarian cancer (diagnosed at any age) who do not share the BRCA1-linked haplotype segregating in the remainder of the cases in the kindred.
[2]Multipoint LOD score calculated using both markers
*kindred contains one individual who had both breast and ovarian cancer; this individual is counted as a breast cancer case and as an ovarian cancer case.

The logarithm of the odds (LOD) scores in these kindreds range from 9.49 to −0.44 for a set of markers in 17q21. Four of the families have convincing LOD scores for linkage, and 4 have low positive or negative LOD scores. The latter kindreds were included because they demonstrate haplotype sharing at chromosome 17q21 for at least 3 affected members. Furthermore, all kindreds in the set display early age of breast cancer onset and 4 of the kindreds include at least one case of ovarian cancer, both hallmarks of BRCA1 kindreds. One kindred, 2082, has nearly equal incidence of breast and ovarian cancer, an unusual occurrence given the relative rarity of ovarian cancer in the population. All of the kindreds except two were ascertained in Utah. K2035 is from the midwest. K2099 is an African-American kindred from the southern USA.

In the initial screen for predisposing mutations in BRCA1, DNA from one individual who carries the perdisplotype in each kindred was tested. The 23 coding exons and associated splice junction were amplified either from genomic DNA samples or from cDNA prepared from lymphocyte mRNA. When the amplified DNA sequences were compared to the wildtype sequence, 4 of the 8 kindred samples were found to contain sequence variants (Table 11).

TABLE 11

PREDISPOSING MUTATIONS

| Kindred Number | Mutation | Coding Effect | Location* |
|---|---|---|---|
| 2082 | C → T | Gln → Stop | 4056 |
| 1910 | extra C | frameshift | 5385 |
| 2099 | T → G | Met → Arg | 5443 |

TABLE 11-continued

PREDISPOSING MUTATIONS

| Kindred Number | Mutation | Coding Effect | Location* |
|---|---|---|---|
| 2035 | ? | loss of transcript | |
| 1901 | 11 bp deletion | frameshift | 189 |

*In Sequence ID NO: 1

All four sequence variants are heterozygous and each appears in only one of the kindreds. Kinderd 2082 contains a nonsense mutation in exon 11 (FIG. 9A), Kindred 1910 contains a single nucleoting insertion in exon 20 (FIG. 9B), and Kindred 2099 contains a missense mutation in exon 21, resulting in a Met→Arg substitution. The frameshift and nonsense mutations are likely disruptive to the function of the BRCA1 product. The peptide encoded by the frameshift allele in Kindred 1910 would contain an altered amino acid sequence beginning 108 residues from the wildtype C-terminus. The peptide encoded by the frameshift allele in Kindred 1901 would contain an altered amino acid sequence beginning with the 24th residue from the wildtype N-terminus. The mutant allele in Kindred 2082 would encode a protein missing 551 residues from the C-terminus. The missense substitution observed in Kindred 2099 is potentially disruptive as it causes the replacement of a small hydrophobic amino acid (Met), by a large charged residue (Arg). Eleven common polymorphisms were also identified, 8 in coding sequence and 3 in introns.

Figure 9A:
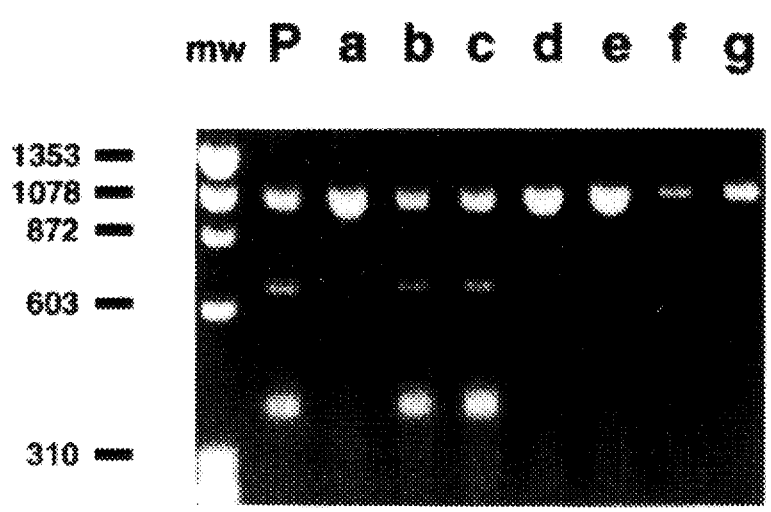
FIG. 9A shows a nonsense mutation in Kindred 2082. P indicates the person originally screened, b and c are haplotype carriers, a, d, e, f, and g do not carry the BRCA1 haplotype. The C to T mutation results in a stop codon and creates a site for the restriction enzyme AvrII. PCR amplification products are cut with this enzyme. The carriers are heterozygous for the site and therefore show three bands. Non-carriers remain uncut.
Figure 9B:
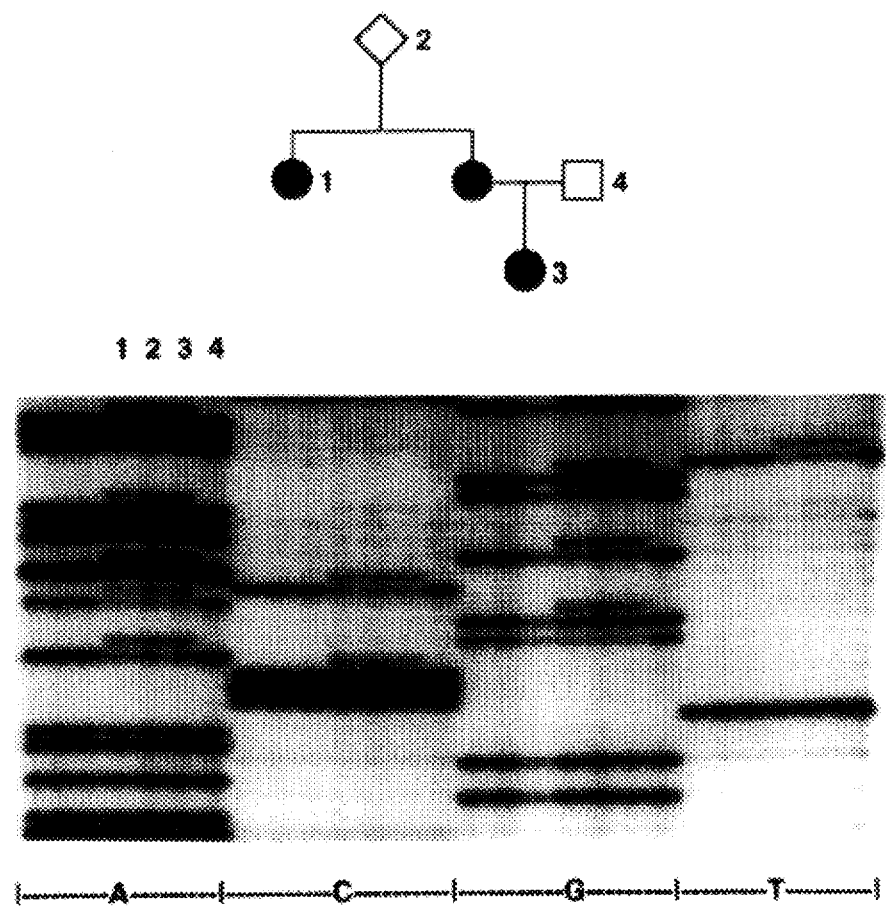
FIG. 9B shows a mutation and cosegregation analysis in BRCA1 kindreds. Carrier individuals are represented as filled circles and squares in the pedigree diagrams. Frameshift mutation in Kindred 1910. The first three lanes are control, noncarrier samples. Lanes labeled 1-3 contain sequences from carrier individuals. Lane 4 contains DNA from a kindred member who does not carry the BRCA1 mutation. The diamond is used to prevent identification of the kindred. The frameshift resulting from the additional C is apparent in lanes labeled 1, 2, and 3.
Figure 9C:
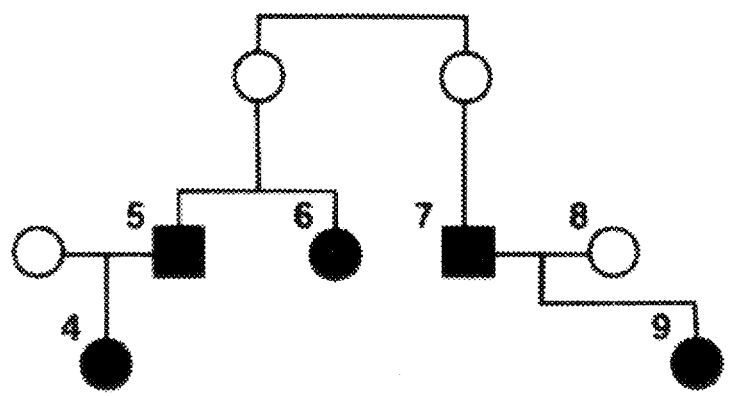
FIG. 9C shows a mutation and cosegregation analysis in BRCA1 kindreds. Carrier individuals are represented as filled circles and squares in the pedigree diagrams. Inferred regulatory mutation in Kindred 2035. ASO analysis of carriers and noncarriers of 2 different polymorphisms (PM1 and PM7) which were examined for heterozygosity in the germline and compared to the heterozygosity of lymphocyte mRNA. The top 2 rows of each panel contain PCR products amplified from genomic DNA and the bottom 2 rows contain PCR products amplified from cDNA. "A" and "G" are the two alleles detected by the ASO. The dark spots indicate that a particular allele is present in the sample. The first three lanes of PM7 represent the three genotypes in the general population.
Figure 9C:
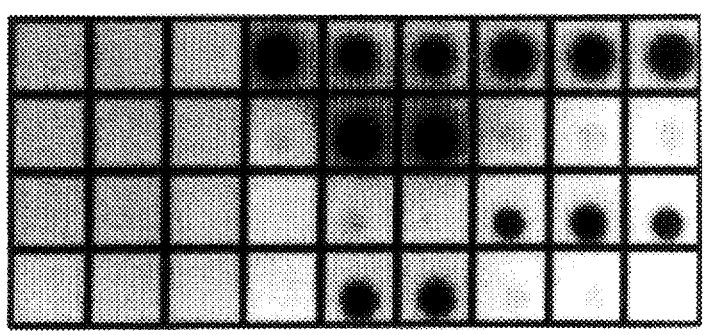
Figure 9C:
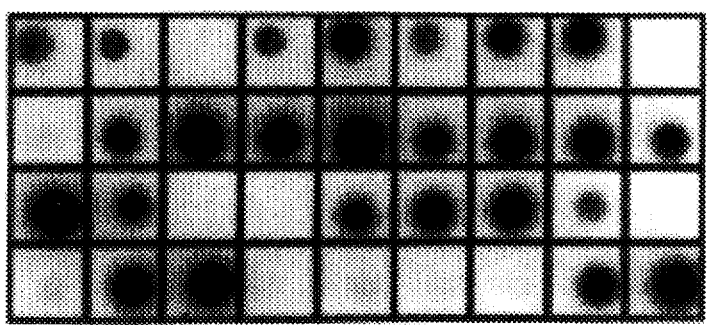

The individual studied in Kindred 2035 evidently contains a regulatory mutation in BRCA 1. In her cDNA, a polymorphic site (A→G at base 3667) appeared homozygous, whereas her genomic DNA revealed heterozygosity at this position (FIG. 9C). A possible explanation for this observation is that mRNA from her mutated BRCA1 allele is absent due to a mutation that affects its production or stability. This possibility was explored further by examining 5 polymorphic sites in the BRCA1 coding region, which are separated by as much as 3.5 kb in the BRCA1 transcript. In all cases where her genomic DNA appeared heterozygous for a polymorphism, cDNA appeared homozygous. In individuals from other kindreds and in nonhaplotype carriers in Kindred 2035, these polymorphic sites could be observed as heterozygous in cDNA, implying that amplification from cDNA was not biased in favor of one allele. This analysis indicates that a BRCA1 mutation in Kindred 2035 either prevents transcription or causes instability or aberrant splicing of the BRCA1 transcript.

Cosegregation of BRCA1 mutations with BRCA1haplotypes and population frequency analysis. In addition to potentially disrupting protein function, two criteria must be met for a sequence variant to qualify as a candidate predisposing mutation. The variant must: 1) be present in individuals from the kindred who carry the predisposing BRCA 1 haplotype and absent in other members of the kindred, and 2) be rare in the general population.

Each mutation was tested for cosegregation with BRCA1. For the frameshift mutation in Kindred 1910, two other haplotype carriers and one non-carrier were sequenced (FIG. 9B). Only the carriers exhibited the frameshift mutation. The C to T change in Kindred 2082 created a new AvrII restriction site. Other carriers and non-carriers in the kindred were tested for the presence of the restriction site (FIG. 9A). An allele-specific oligonucleotide (ASO) was designed to detect the presence of the sequence variant in Kindred 2099. Several individuals from the kindred, some known to carry the haplotype associated with the predisposing allele, and others known not to carry the associated haplotype, were screened by ASO for the mutation previously detected in the kindred. In each kindred, the corresponding mutant allele was detected in individuals carrying the BRCA1-associated haplotype, and was not detected in noncarriers. In the case of the potential regulatory mutation observed in the individual from Kindred 2035, cDNA and genomic DNA from carriers in the kindred were compared for heterozygosity at polymorphic sites. In every instance, the extinguished allele in the cDNA sample was shown to lie on the chromosome that carries the BRCA1 predisposing allele (FIG. 9C).

To exclude the possibility that the mutations were simply common polymorphisms in the population, ASOs for each mutation were used to screen a set of normal DNA samples. Gene frequency estimates in Caucasians were based on random samples from the Utah population. Gene frequency estimates in African-Americans were based on 39 samples provided by M. Peracek-Vance which originate from African-Americans used in her linkage studies and 20 newborn Utah African-Americans. None of the 4 potential predisposing mutations was found in the appropriate control population, indicating that they are rare in the general population. Thus, two important requirements for BRCA1 susceptibility alleles were fulfilled by the candidate predisposing mutations: 1) cosegregation of the mutant allele with disease, and 2) absence of the mutant allele in controls, indicating a low gene frequency in the general population.

Phenotypic Expression of BRCA1 Mutations. The effect of the mutations on the BRCA1 protein correlated with differences in the observed phenotypic expression in the BRCA1 kindreds. Most BRCA 1 kindreds have a moderately increased ovarian cancer risk, and a smaller subset have high risks of ovarian cancer, comparable to those for breast cancer (Easton et al., 1993). Three of the four kindreds in which BRCA1 mutations were detected fall into the former category, while the fourth (K2082) falls into the high ovarian cancer risk group. Since the BRCA1 nonsense mutation found in K2082 lies closer to the amino terminus than the other mutations detected, it might be expected to have a different phenotype. In fact, Kindred K2082 mutation has a high incidence of ovarian cancer, and a later mean age at diagnosis of breast cancer cases than the other kindreds (Goldgar et al., 1994). This difference in age of onset could be due to an ascertainment bias in the smaller, more highly penetrant families, or it could reflect tissue-specific differences in the behavior of BRCA1 mutations. The other 3 kindreds that segregate known BRCA1 mutations have, on average, one ovarian cancer for every 10 cases of breast cancer, but have a high proportion of breast cancer cases diagnosed in their late 20's or early 30's. Kindred 1910, which has a frameshift mutation, is noteworthy because three of the four affected individuals had bilateral breast cancer, and in each case the second tumor was diagnosed within a year of the first occurrence. Kindred 2035, which segregates a potential regulatory BRCA1 mutation, might also be expected to have a dramatic phenotype. Eighty percent of breast cancer cases in this kindred occur under age 50. This figure is as high as any in the set, suggesting a BRCA1 mutant allele of high penetrance (Table 10).

Although the mutations described above clearly are deleterious, causing breast cancer in women at very young ages, each of the four kindreds with mutations includes at least one woman who carries the mutation who lived until age 80 without developing a malignancy. It will be of utmost importance in the studies that follow to identify other genetic or environmental factors that may ameliorate the effects of BRCA1 mutations.

In four of the eight putative BRCA1-linked kindreds, potential predisposing mutations were not found. Three of these four have LOD scores for BRCA1-linked markers of less than 0.55. Thus, these kindreds may not in reality segregate BRCA1 predisposing alleles. Alternatively, the mutations in these four kindreds may lie in regions of BRCA1 that, for example, affect the level of transcript and therefore have thus far escaped detection.

Role of BRCA1 in Cancer. Most tumor suppressor genes identified to date give rise to protein products that are absent, nonfunctional, or reduced in function. The majority of TP53 mutations are missense; some of these have been shown to produce abnormal p53 molecules that interfere with the function of the wildtype product (Shaulian el al., 1992; Srivastava et al., 1993). A similar dominant negative mechanism of action has been proposed for some adenomatous polyposis coli (APC) alleles that produce truncated molecules (Su et al., 1993), and for point mutations in the Wilms' tumor gene (WT1) that alter DNA binding of the protein (Little et al., 1993). The nature of the mutations observed in the BRCA1 coding sequence is consistent with production of either dominant negative proteins or nonfunctional proteins. The regulatory mutation inferred in Kindred 2035 cannot be a dominant negative; rather, this mutation likely causes reduction or complete loss of BRCA1 expression from the affected allele.

The BRCA1 protein contains a $C_3HC_4$ zinc-finger domain, similar to those found in numerous DNA binding proteins and implicated in zinc-dependent binding to nucleic acids. The first 180 amino acids of BRCA1 contain five more basic residues than acidic residues. In contrast, the remainder of the molecule is very acidic, with a net excess of 70 acidic residues. The excess negative charge is particularly concentrated near the C-terminus. Thus, one possibility is that BRCA1 encodes a transcription factor with an N-terminal DNA binding domain and a C-terminal transactivational "acidic blob" domain. Interestingly, another familial tumor suppressor gene, WT1, also contains a zinc-finger motif (Haber el al., 1990). Many cancer predisposing mutations in WT1 alter zinc-finger domains (Little et al., 1993; Haber et al., 1990; Little et al., 1992). WT1 encodes a transcription factor, and alternative splicing of exons that encode parts of the zinc-finger domain alter the DNA binding properties of WT1 (Bickmore et al., 1992). Some alternatively spliced forms of WT1 mRNA generate molecules that act as transcriptional repressors (Drummond et al., 1994). Some BRCA1 splicing variants may alter the zinc-finger motif, raising the possibility that a regulatory mechanism similar to 10 that which occurs in WT1 may apply to BRCA1.

EXAMPLE 9

Analysis of Tumors for BRCA1 Mutations

To focus the analysis on tumors most likely to contain BRCA1 mutations, primary breast and ovarian carcinomas were typed for LOH in the BRCA1 region. Three highly polymorphic, simple tandem repeat markers were used to assess LOH: D17S1323 and D17S855, which are intragenic to BRCA1, and D17S1327, which lies approximately 100 kb distal to BRCA1. The combined LOH frequency in informative cases (i.e., where the germline was heterozygous) was 32/72 (44%) for the breast carcinomas and 12/21 (57%) for the ovarian carcinomas, consistent with previous measurements of LOH in the region (Futreal et al., 1992b; Jacobs et al., 1993; Sato et al., 1990; Eccles et al., 1990; Cropp et al., 1994). The analysis thus defined a panel of 32 breast tumors and 12 ovarian tumors of mixed race and age of onset to be examined for BRCA mutations. The complete 5,589 bp coding region and intron/exon boundary sequences of the gene were screened in this tumor set by direct sequencing alone or by a combination of single-strand conformation analysis (SSCA) and direct sequencing.

A total of six mutations (of which two are identical) was found, one in an ovarian tumor, four in breast tumors and one in a male unaffected haplotype carrier (Table 12). One mutation, Glu1541Ter, introduced a stop codon that would create a truncated protein missing 323 amino acids at the carboxy terminus. In addition, two missense mutations were identified. These are Ala1708Glu and Met1775Arg and involve substitutions of small, hydrophobic residues by charged residues. Patients 17764 and 19964 are from the same family. In patient OV24 nucleotide 2575 is deleted and in patients 17764 and 19964 nucleotides 2993–2996 are deleted.

TABLE 12

Predisposing Mutations

| Patient | Codon | Nucleotide Change | Amino Acid Change | Age of Onset | Family History |
|---|---|---|---|---|---|
| BT098 | 1541 | GAG → TAG | Glu → Stop | 39 | – |
| OV24 | 819 | 1 bp deletion | frameshift | 44 | – |
| BT106 | 1708 | GCG → GAG | Ala → Glu | 24 | + |
| MC44 | 1775 | ATG → AGG | Met → Arg | 42 | + |
| 17764 | 958 | 4 bp deletion | frameshift | 31 | + |
| 19964 | 958 | 4 bp deletion | frameshift |  | +* |

*Unaffected haplotype carrier, male

Several lines of evidence suggest that all five mutations represent BRCA1 susceptibility alleles:

(i) all mutations are present in the germline;

(ii) all are absent in appropriate control populations, suggesting they are not common polymorphisms;

(iii) each mutant allele is retained in the tumor, as is the case in tumors from patients belonging to kindreds that segregate BRCA1 susceptibility alleles (Smith et al., 1992; Kelsell et al., 1993) (if the mutations represented neutral polymorphisms, they should be retained in only 50% of the cases);

(iv) the age of onset in the four breast cancer cases with mutations varied between 24 and 42 years of age, consistent with the early age of onset of breast cancer in individuals with BRCA1 susceptibility; similarly, the ovarian cancer case was diagnosed at 44, an age that falls in the youngest 13% of all ovarian cancer cases; and finally, (v) three of the five cases have positive family histories of breast or ovarian cancer found retrospectively in their medical records, although the tumor set was not selected with regard to this criterion.

BT106 was diagnosed at a very early age with breast cancer. Her mother had ovarian cancer, her father had melanoma, and her paternal grandmother also had breast cancer. Patient MC44, an African-American, had bilateral breast cancer at an early age. This patient had a sister who died of breast cancer at a very early age. Her mutation (Met1775Arg) had been detected previously in Kindred 2099, an African-American family that segregates a BRCA1 susceptibility allele, and was absent in African-American and Caucasian controls.

Patient MC44, to our knowledge, is unrelated to Kindred 2099. The detection of a rare mutant allele, once in a BRCA1 kindred and once in the germline of an apparently unrelated early-onset breast cancer case, suggests that the Met1775Arg change may be a common predisposing mutation in African-Americans. Collectively, these observations indicate that all four BRCA1 mutations in tumors represent susceptibility alleles; no somatic mutations were detected in the samples analyzed.

The paucity of somatic BRCA1 mutations is unexpected, given the frequency of LOH on 17q, and the usual role of susceptibility genes as tumor suppressors in cancer progression. There are three possible explanations for this result: (i) some BRCA1 mutations in coding sequences were missed by our screening procedure; (ii) BRCA1 somatic mutations fall primarily outside the coding exons; and (iii) LOH events in 17q do not reflect BRCA1 somatic mutations.

If somatic BRCA1 mutations truly are rare in breast and ovary carcinomas, this would have strong implications for the biology of BRCA1. The apparent lack of somatic BRCA1 mutations implies that there may be some fundamental difference in the genesis of tumors in genetically predisposed BRCA1 carriers, compared with tumors in the general population. For example, mutations in BRCA1 may have an effect only on tumor foination at a specific stage early in breast and ovarian development. This possibility is consistent with a primary function for BRCA1 in premenopausal breast cancer. Such a model for the role of BRCA1 in breast and ovarian cancer predicts an interaction between reproductive hormones and BRCA1 function. However, no clinical or pathological differences in familial versus sporadic breast and ovary tumors, other than age of onset, have been described (Lynch et al., 1990). On the other hand, the recent finding of increased TP53 mutation and microsatellite instability in breast tumors from patients with a family history of breast cancer (Glebov et al., 1994) may reflect some difference in tumors that arise in genetically predisposed persons. The involvement of BRCA1 in this phenomenon can now be addressed directly. Alternatively, the lack of somatic BRCA1 mutations may result from the existence of multiple genes that function in the same pathway of tumor suppression as BRCA1, but which collectively represent a more favored target for mutation in sporadic tumors. Since mutation of a single element in a genetic pathway is generally sufficient to disrupt the pathway, BRCA1 might mutate at a rate that is far lower than the sum of the mutational rates of the other elements.

EXAMPLE 10

Analysis of the BRCA1 Gene

The structure and function of BRCA1 gene are determined according to the following methods.

Biological Studies. Mammalian expression vectors containing BRCA1 cDNA are constructed and transfected into appropriate breast carcinoma cells with lesions in the gene. Wild-type BRCA1 cDNA as well as altered BRCA1 cDNA are utilized. The altered BRCA1 cDNA can be obtained from altered BRCA1 alleles or produced as described below. Phenotypic reversion in cultures (e.g., cell morphology, doubling time, anchorage-independent growth) and in animals (e.g., tumorigenicity) is examined. The studies will employ both wild-type and mutant forms (Section B) of the gene.

Molecular Genetics Studies. In vitro mutagenesis is performed to construct deletion mutants and missense mutants (by single base-pair substitutions in individual codons and cluster charged→alanine scanning mutagenesis). The mutants are used in biological, biochemical and biophysical studies.

Mechanism Studies. The ability of BRCA1 protein to bind to known and unknown DNA sequences is examined. Its ability to transactivate promoters is analyzed by transient reporter expression systems in mammalian cells. Conventional procedures such as particle-capture and yeast two-hybrid system are used to discover and identify any functional partners. The nature and functions of the partners are characterized. These partners in turn are targets for drug discovery.

Structural Studies. Recombinant proteins are produced in E. coli, yeast, insect and/or mammalian cells and are used in crystallographical and NMR studies. Molecular modeling of the proteins is also employed. These studies facilitate structure-driven drug design.

EXAMPLE 11

Two Step Assay to Detect the Presence of BRCA1 in a Sample

Patient sample is processed according to the method disclosed by Antonarakis et al. (1985), separated through a 1% agarose gel and transferred to nylon membrane for Southern blot analysis.

Membranes are UV cross linked at 150 mJ using a GS Gene Linker (Bio-Rad). BRCA1 probe corresponding to nucleotide positions 3631–3930 of SEQ ID NO:1 is subcloned into pTZ18U. The phagemids are transformed into E. coli MV1190 infected with M13KO7 helper phage (Bio-Rad, Richmond, Calif.). Single stranded DNA is isolated according to standard procedures (see Sambrook et al., 1989).

Blots are prehybridized for 15–30 min at 65° C. in 7% sodium dodecyl sulfate (SDS) in 0.5M $NaPO_4$. The methods follow those described by Nguyen et al., 1992. The blots are hybridized overnight at 65° C. in 7% SDS, 0.5M $NaPO_4$ with 25–50 ng/ml single stranded probe DNA. Post-hybridization washes consist of two 30 min washes in 5% SDS, 40 mM $NaPO_4$ at 65° C., followed by two 30 min washes in 1% SDS, 40 mM $NaPO_4$ at 65° C.

Next the blots are rinsed with phosphate buffered saline (pH 6.8) for 5 min at room temperature and incubated with 0.2% casein in PBS for 30–60 min at room temperature and rinsed in PBS for 5 min. The blots are then preincubated for 5–10 minutes in a shaking water bath at 45° C. with hybridization buffer consisting of 6M urea, 0.3M NaCl, and 5X Denhardt's solution (see Sambrook, et al., 1989). The buffer is removed and replaced with 50–75 µl/cm² fresh hybridization buffer plus 2.5 nM of the covalently cross-linked oligonucleotide-alkaline phosphatase conjugate with the nucleotide sequence complementary to the universal primer site (UP-AP, Bio-Rad). The blots are hybridized for 20–30 min at 45° C. and post hybridization washes are incubated at 45° C. as two 10 min washes in 6M urea, 1× standard saline citrate (SSC), 0.1% SDS and one 10 min wash in 1× SSC, 0.1% Triton®X-100. The blots are rinsed for 10 min at room temperature with 1× SSC.

Blots are incubated for 10 min at room temperature with shaking in the substrate buffer consisting of 0.1M diethanolamine, 1 mM $MgCl_2$, 0.02% sodium azide, pH 10.0. Individual blots are placed in heat sealable bags with substrate buffer and 0.2 mM AMPPD (3-(2'-spiroadamantane)-4-methoxy -4-(3'-phosphoryloxy)phenyl-1,2-dioxetane, disodium salt, Bio-Rad). After a 20 min incubation at room temperature with shaking, the excess AMPPD solution is removed. The blot is exposed to X-ray film overnight. Positive bands indicate the presence of BRCA1.

EXAMPLE 12

Generation of Polyclonal Antibody against BRCA1

Segments of BRCA1 coding sequence were expressed as fusion protein in E. coli. The overexpressed protein was purified by gel elution and used to immunize rabbits and mice using a procedure similar to the one described by Harlow and Lane, 1988. This procedure has been shown to generate Abs against various other proteins (for example, see Kraemer et al., 1993).

Briefly, a stretch of BRCA1 coding sequence was cloned as a fusion protein in plasmid PET5A (Novagen, Inc., Madison, Wis.). The BRCA1 incorporated sequence includes the amino acids corresponding to #1361–1554 of SEQ ID NO:2. After induction with IPTG, the overexpression of a fusion protein with the expected molecular weight was verified by SDS/PAGE. Fusion protein was purified from the gel by electroelution. The identification of the protein as the BRCA1 fusion product was verified by protein sequencing at the N-terminus. Next, the purified protein was used as immunogen in rabbits. Rabbits were immunized with 100 µg of the protein in complete Freund's adjuvant and boosted twice in 3 week intervals, first with 100µg of immunogen in incomplete Freund's adjuvant followed by 100 µg of immunogen in PBS. Antibody containing serum is collected two weeks thereafter.

This procedure is repeated to generate antibodies against the mutant forms of the BRCA1 gene.

These antibodies, in conjunction with antibodies to wild type BRCA1, are used to detect the presence and the relative level of the mutant forms in various tissues and biological fluids. EXAMPILE 13

Generation of Monoclonal Antibodies Specific for BRCA1

Monoclonal antibodies are generated according to the following protocol. Mice are immunized with immunogen comprising intact BRCA1 or BRCA1 peptides (wild type or mutant) conjugated to keyhole limpet hemocyanin using glutaraldehyde or EDC as is well known.

The immunogen is mixed with an adjuvant. Each mouse receives four injections of 10 to 100 µg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of BRCA1 specific antibodies by ELISA or RIA using wild type or mutant BRCA1 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 14

Sandwich Assay for BRCA1

Monoclonal antibody is attached to a solid surface such as a plate, tube, bead, or particle. Preferably, the antibody is attached to the well surface of a 96-well ELISA plate. 100 µl sample (e.g., serum, urine, tissue cytosol) containing the BRCA1 peptide/protein (wild-type or mutant) is added to the solid phase antibody. The sample is incubated for 2 hrs at room temperature. Next the sample fluid is decanted, and the solid phase is washed with buffer to remove tunbound material. 100 µl of a second monoclonal antibody (to a different determinant on the BRCA1 peptide/protein) is added to the solid phase. This antibody is labeled with a detector molecule (e.g., $^{125}$I, enzyme, fluorophore, or chromophore) and the solid phase with the second antibody is incubated for two hrs at room temperature. The second antibody is decanted and the solid phase is washed with buffer to remove unbound material.

The amount of bound label, which is proportional to the amount of BRCA1 peptide/protein present in the sample, is quantitated. Separate assays are performed using monoclonal antibodies which are specific for the wild-type BRCA1 as well as monoclonal antibodies specific for each of the mutations identified in BRCA1.

Industrial Utility

As previously described above, the present invention provides materials and methods for use in testing BRCA1 alleles of an individual and an interpretation of the normal or predisposing nature of the alleles. Individuals at higher than normal risk might modify their lifestyles appropriately. In the case of BRCA1, the most significant non-genetic risk factor is the protective effect of an early, full term pregnancy. Therefore, women at risk could consider early childbearing or a therapy designed to simulate the hormonal effects of an early full-term pregnancy. Women at high risk would also strive for early detection and would be more highly motivated to learn and practice breast self examination. Such women would also be highly motivated to have regular mammograms, perhaps starting at an earlier age than the general population. Ovarian screening could also be undertaken at greater frequency. Diagnostic methods based on sequence analysis of the BRCA1 locus could also be applied to tumor detection and classification. Sequence analysis could be used to diagnose precursor lesions. With the evolution of the method and the accumulation of information about BRCA1 and other causative loci, it could become possible to separate cancers into benign and malignant.

Women with breast cancers may follow different surgical procedures if they are predisposed, and therefore likely to have additional cancers, than if they are not predisposed. Other therapies may be developed, using either peptides or small molecules (rational drug design). Peptides could be the missing gene product itself or a portion of the missing gene product. Alternatively, the therapeutic agent could be another molecule that mimics the deleterious gene's function, either a peptide or a nonpeptidic molecule that seeks to counteract the deleterious effect of the inherited locus. The therapy could also be gene based, through introduction of a normal BRCA1 allele into individuals to make a protein which will counteract the effect of the deleterious allele. These gene therapies may take many forms and may be directed either toward preventing the tumor from forming, curing a cancer once it has occurred, or stopping a cancer from metastasizing.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Altschul, S. F. et al. (1990). *J. Mol. Biol* 215: 195–197.
American Cancer Society, Cancer Facts & Figures - 1992. (American Cancer Society, Atlanta, Ga.).
Anand, R. (1992). *Techniques for the Analysis of Complex Genomes*, (Academic Press).
Anderson, et al. (1980). *Proc. Natl. Acad Sci. USA* 77:5399–5403.
Anderson, D. E. (1972). *J. Natl. Cancer Inst* 48:1029–1034.
Anderson, J. A., et al. (1992). *J. Otolaryngology* 21:321.
Antonarakis, S. E., et al. (1985). *New Eng. J. Med* 313:842–848.
Ausubel, F. M., et al. (1992). *Current Protocols in Molecular Biology*, (J. Wiley and Sons, N.Y.)
Beaucage & Carruthers (1981). *Tetra. Letts.* 22:1859–1862.
Berkner (1992). *Curr. Top. Microbiol. Immunol.* 158:39–61.
Berkner, et al. (1988). *BioTechniques* 6:616–629.
Bickmore, W. A., et al. (1 992). *Science* 257:235–7.
Bishop, D. T., et al. (1988). *Genet. Epidemiol.* 5:151–169.
Bishop, D. T. and Gardner, E. J. (1980). In: *Banbury Report 4: Cancer Incidence in Defined Populations* (J. Cairns, J. L. Lyon, M. Skolnick, eds.), Cold Spring Harbor Laboratory, Cold Spring Harbor, N.Y., 309–408.
Botstein, et al. (1980). *Am. J Hum. Genet.* 32:314–331.
Bowcock, A. M., et al. (1993). *Am. J. Hum. Genet.* 52:718.
Brandyopadhyay and Temin (1984). *Mol. Cell Biol.* 4:749–754.
Breakfield and Geller (1987). *MoL Neurobiol.* 1:337–371.
Brinster, et al. (1981). *Cell* 27:223–231.
Buchschacher and Panganiban (1992). *J. Virol.* 66:2731–2739.
Buckler, et al. (1991). *Proc. Nail Acad Sci. USA* 88:4005–4009.
Caluon-Albright, L., et al. (1994). *Cancer Research* 54:2378–2385.
Capecchi, M. R. (1989). *Science* 244:1288.
Cariello (1988). *Human Genetics* 42:726.
Claus, E., et al. (1991). *Am. J Hum. Genet.* 48:232–242.
Conner, B. J., et al. (1983). *Proc. Natl. Acad Sci. USA* 80:278–282.
Constantini and Lacy ( 1981). *Nature* 294:92–94.
Cotten, et al. (1990). *Proc. Natl. Acad. Sci. USA* 87:4033–4037.
Cotton, et al. (1988). *Proc. Natl. Acad. Sci. USA* 85:4397.
Cropp, C.S., et al. (1994). *Cancer Res.* 54:2548–2551.
Culver, et al. (1992). *Science* 256:1550–1552.
Curiel, et al. (1991a). *Proc. Natl. Acad. Sci. USA* 88:8850–8854.
Curiel, et al. (1991b). *Hum. Gene Ther.* 3:147–154.
Deutscher, M. (1990). *Meth. Enzymology* 182 (Academic Press, San Diego, Calif.).
Donehower, L. A., et al. (1992). *Nature* 356:215.
Drummond,I. A., et al. (1994). *Mol. Cell Biol.* 14:3800–9.
Easton, D., et al. (1993). *Am. J. Hum. Genet.* 52:678–701.
Eccles, D. M., et al. (1990). *Oncogene* 5:1599–1601.
*Enhancers and Eurkaryotic Gene Expression*, Cold Spring Harbor Press, Cold Spring Harbor, N.Y. (1983).
Erickson, J. et al. (1990). *Science* 249:527–533.
Fain, P. R. (1992). *Cytogen. Cell Genet.* 60:178.
Fegner, et al. (1987). *Proc. Natl. Acad. Sci. USA* 84:7413–7417.

Fiers, et a l. (1978). *Nature* 273:113.
Fink, et al. (1992). *Hum. Gene Ther.* 3:11–19.
Finkelstein, J., et al. (1990). *Genomics* 7:167–172.
Freese, et al. (1990). *Biochem. Pharmacol.* 40:2189–2199.
Friedman, T. (1991). In *Therapy for Genetic Diseases*, T. Friedman, ed., Oxford University Press, pp. 105–121.
Futreal (1993). Ph.D. Thesis, University of North Carolina, Chapel Hill.
Futreal, A., et al. (1992a). *Hum. Molec. Genet.* 1:66.
Futreal, P. A., et al. (1992b). *Cancer Res.* 52:2624–2627.
Glebov, O. K., et al. (1994). *Cancer Res.* 54:3703–3709.
Glover, D. (1985). *DNA Cloning*, I and II (Oxford Press).
Go, R. C. P., et al. (1983). *J. Natl. Cancer Inst.* 71:455–461.
Goding (1986). *Monoclonal Antibodies. Principles and Practice*, 2d ed. (Academic Press, N.Y.).
Godowski, et al. (1988). *Science* 241:812–816.
Goldgar, D. E., et al. (1994). *J. Natl. Can. Inst.* 86:3:200–209.
Gordon, et al. (1980). *Proc. Natl. Acad. Sci. USA* 77:7380–7384.
Gorziglia and Kapikian (1992). *J. Virol.* 66:4407–4412.
Graham and van der Eb (1973). *Virology* 52:456–467.
Grompe, M., (1993). *Nature Genetics* 5:111–117.
Grompe, M., et al., (1989). *Proc. Natl. Acad. Sci. USA* 86:5855–5892.
Guthrie, G. & Fink, G. R. (1991). *Guide to Yeast Genetics and Molecular Biology* (Academic Press).
Haber, D. A., et al. (1990). *Cell* 61:1257–69.
Hall, J. M., et al. (1990). *Science* 250:1684–1689.
Hall, J. M., et al. (1992). *Amn. J. Hum. Genet.* 50:1235–1241.
Harlow & Lane (1988). *Antibodies: A Laboratory Manual* (Cold Spring Harbor Laboratory, Cold Spring Harbor, N.Y.
Hasty, P., K., et al. (1991). *Nature* 350:243.
Helseth, et al. (1990). *J. Virol.* 64:2416–2420.
Hodgson, J. (1991). *Bio/Technology* 9:19–21.
Huse, et al. (1989). *Science* 246:1275–1281.
Innis et al. (1990). *PCR Protocols: A Guide to Methods and Applications* (Academic Press, San Diego, Calif.).
Jablonski, E., et al. (1986). *Nuc. Acids Res.* 14:6115–6128.
Jacobs, I. J., et al. (1993). *Cancer Res.* 53:1218–1221.
Jakoby, W. B. and Pastan, I. H. (eds.) (1979). *Cell Culture. Methods in Enzymology*, volume 58 (Academic Press, Inc., Harcourt Brace Jovanovich (N.Y.)).
Jeffreys, et al. (1985). *Nature* 314:67–73.
Johnson, et al. (1992). *J. Virol.* 66:2952–2965.
Kamb, A. et al. (1994). *Science* 264:436–440.
Kandpal, et al. (1990). *Nucl. Acids Res.* 18:1789–1795.
Kaneda, et al. (1989). *J. Biol. Chem.* 264:12126–12129.
Kanehisa (1984). *Nucl. Acids Res.* 12:203–213.
Kelsell, D. P., et al. (1993). *Human Mol. Genet.* 2:1823–1828.
Kinszler, K. W., et al. (1991). *Science* 251:1366–1370.
Knudson, A. G. (1993). *Nature Genet.* 5:103.
Kohler, G. and Milstein, C. (1975). *Nature* 256:495–497.
Kozak, M. (1987). *Nucleic Acids Res.* 15:8125–8148.
Kraemer, F.B. et aL (1993). *J. Lipid Res.* 34:663–672.
Kubo, T., et al. (1988). *FEBS Letts.* 241:119.
Landegren, et al. (1988). *Science* 242:229.
Lim, et al. (1992). *Circulation* 83:2007–2011.
Lindsay, S., et al. (1987). *Natire* 327:336–368.
Litt, et al. (1989). Am. J. *Hum. Genet.* 44:397–401.
Little, M. H., et al. (1992). *Proc. Natl. Acad. Sci. USA* 89:4791.
Little, M. H., et al. (1993). *Hum. Mol. Genet.* 2:259.
Lovett, et al. (1991). *Proc. Natl. Acad. Sci. USA* 88:9628–9632.
Lynch, H. T., et al. (1990). *Gynecol. Oncol* 36:48–55.
Madzak, et al. (1992). *J. Gen. Virol.* 73:1533–1536.
Malkin, D., et al. (1990). *Science* 250:1233–1238.
Maniatis, T., et al. (1982). *Molecular Cloning: A Laboratory Manual* (Cold Spring Harbor Laboratory, Cold Spring Harbor, N.Y.).
Mann and Baltimore (1985). *J. Virol.* 54:401–407.
Margaritte, et al. (1992). *Am. J. Hum. Genet.* 50:1231–1234.
Margolskee (1992). *Curr. Top. Microbiol. Immunol.* 158:67–90.
Martin, R., et al. (1990). *BioTechniques* 9:762–768.
Matteucci, M. D. and Caruthers, M. H. (1981). *J. Am. Chem. Soc.* 103:3185.
Matthews & Kricka (1988). *Anal. Biochem.* 169:1.
Merrifield (1963). *J. Am. Chem. Soc.* 85:2149–2156.
Mettlin, C., et al. (1990). *American Journal of Epidemiology* 131:973–983.
Metzger, et al. (1988). *Nature* 334:31–36.
Miller (1992). *Curr. Top. Microbiol. Immunol.* 158:1–24.
Miller, et al. (1985). *Mol. Cell. Biol.* 5:431–437.
Miller, et al. (1988). *J. Virol.* 62:4337–4345.
Mittlin (1989). *Clinical Chem.* 35:1819.
Modrich, P. (1991). *Ann. Rev. Genet.* 25:229–253.
Mombaerts, P., et al. (1992). *Cell* 68:869.
Monaco, et al. (1986). *Nature* 323:646.
Moss (1992). *Curr. Top. Microbiol. Immunol.* 158:25–38.
Muzyczka (1992). *Curr. Top. Microbiol. Immunol.* 158:97–123.
Nabel (1992). *Hum. Gene Ther.* 3:399–410.
Nabel, et al. (1990). *Science* 249:1285–1288.
Nakamura, et al. (1987). *Science* 235:1616–1622.
Narod, S. A., et al. (1991). *The Lancet* 338:82–83.
Newman, B., et al. (1988). *Proc. Natl. Acad. Sci. USA* 85:3044–3048.
Newton, C. R., Graham, A., Heptinstall, L. E., Powell, S. J., Summers, C., Kalsheker, N., Smith, J. C., and Markham, A. F. (1989). *Nucl. Acids Res.* 17:2503–2516.
Nguyen, Q., et al. (1992). *BioTechniques* 13:116–123.
Novack, et al. (1986). *Proc. Natl. Acad. Sci. USA* 83:586.
Oh, J. (1985). *Analysis of Human Genetic Linkage*, Johns Hopkins University Press, Baltimore, Md, pp. 1–216.
Ohi, et al. (1990). *Gene* 89:279–282.
Oliphant, A., et al (1991). *Nucleic Acid Res.* 19:4794.
Oliphant, A., et al. (1991). *Nucleic Acid Res.* 19:4795.
Orita, et al. (1989). *Proc. Natl. Acad. Sci. USA* 86:2776–2770.
Page, et al. (1990). *J. Virol.* 64:5370–5276.
Pellicer, et al. (1980). *Science* 209:1414–1422.
Petropoulos, et al. (1992). *J. Virol.* 66:3391–3397.
Philpott, K. L., et al. (1992). *Science* 256:1448.
Pierce, et al. (1992). *Proc. Natl. Acad. Sci. USA* 89:2056–2060.
Quantin, et al. (1992). *Proc. Natl. Acad. Sci. USA* 89:2581–2584.
Rano & Kidd (1989). *Nucl. Acids Res.* 17:8392.
Rigby, P. W. J., et al. (1977). *J. Mol. Biol.* 113:237–251.
Rosenfeld, et al. (1992). *Cell* 68:143–155.
Sambrook, J., et al. (1989). *Molecular Cloning: A Laboratory Manual*, 2nd Ed. (Cold Spring, Harbor Laboratory, Cold Spring Harbor, N.Y.).
Sato, T., et al. (1990). *Cancer Res.* 50:7184–7189.
Scharf (1986). *Science* 233:1076.
Scopes, R. (1982). *Protein Purification: Principles and Practice*, (Springer-Verlag, N.Y.).
Shaulian, E., et al. (1992). *Mwol. Cell Biol.* 12:5581–92.
Sheffield, V. C., et al. (1989). *Proc. Natl. Acad. Sci. USA* 86:232–236.

Sheffield, V. C., et al. (1991). *Am. J. Hum. Genet.* 49:699–706.
Shenk, et al. (1975). *Proc. Natl. Acad. Sci. USA* 72:989.
Shimada, et al. (1991). *J. Clin. Invest.* 88:1043–1047.
Shinkai, Y., et al. (1992). *Cell* 68:855.
Shizuya, H., et al. (1992). *Proc. Natl. Acad. Sci. USA* 89:8794–8797.
Simard, J., et al. (1993). *Human Mol Genet.* 2:1193–1199.
Skolnick, M. H. and Wallace, B. R. (1988). *Genomics* 2:273–279.
Skolnick, M. H., et al. (1990). *Science* 250:1715–1720.
Smith, S. A., et al. (1992). *Nature Genetics* 2:128–131.
Smith, T. F. and Waterman, M.S. (1981). *J. Mol. Biol.* 147:195–197.
Snouwaert, J. N., et al. (1992). *Science* 257:1083.
Sorge, et al. (1984). *Mol. Cell. Biol.* 4:1730–1737.
Srivastava, S., et al. (1993). *Cancer Res.* 53:4452–5.
Sternberg (1990). *Proc. Natl. Acad. Sci. USA* 87:103–107.
Stemberg, et al. (1990). *The New Biologist* 2:151–162.
Stewart, et al. (1992). *Hum. Gene Ther.* 3:267–275.
Stratford-Perricaudet, et al. (1990). *Hum. Gene Ther.* 1:241–256.
Swift, M., et al. (1991). *N. Engl. J. Med.* 325:1831–1836.
Swift, M., et al. (1976). *Cancer Res.* 36:209–215.
Su, L. K., et al. (1993). *Cancer Res.* 53:2728–31.
Thomas, A. and Skolnick, M. H. (1994). *IMA Journal of Mathematics Applied in Medicine and Biology* (in press).
Tonolio, D., et al. (1990). Cold Spring Harbor Conference.
Valancius, V. & Smithies, O. (1991). *Mol. Cell Biol.* 11:1402.
van Dilla, et al. (1986). *Biotechnology* 4:537–552.
Wagner, et al. (1990). *Proc. Natl. Acad. Sci. USA* 87:3410–3414.
Wagner, et al. (1991). *Proc. Natl. Acad. Sci. USA* 88:4255–4259.
Wang and Huang (1989). *Biochemistry* 28:9508–9514.
Wartell, R. M., et al. (1990). *Nucl. Acids Res.* 18:2699–2705.
Weber, J. L. (1990). *Genomics* 7:524–530.
Weber and May (1989). *Am. J. Hum. Genet.* 44:388–396.
Weber, J. L., et al. (1990). *Nucleic Acid Res.* 18:4640.
Wells, J. A. (1991). *Methods in Enzymol.* 202:390–411.
Wetmur & Davidson (1968). *J. Mol. Biol.* 31:349–370.
White, M. B., et al.,(1992). *Genomics* 12:301–306.
White and LaUuel (1988). *Ann. Rev. Genet.* 22:259–279.
Wilkinson, et al. (1992). *Nucleic Acids Res.* 20:22,4–2239.
Willams and Anderson (1984). *Genet. Epidemiol.* 1:7–20.
Wolff, et al. (1990). *Science* 247:1465–1468.
Wolff, et al. (1991). *BioTechniques* 11:474–485.
Wooster, R., et al. (1994). *Science* 265:2088.
Wu, et al. (989a). *Genomics* 4:560–569.
Wu, et al. (989b). *J. Biol. Chem.* 26 4:16985–16987.
Wu, et al. (991). *J. Biol. Chem.* 266:143 138–14342.
Zenke, et al. (1 990). *Proc. Natl. Acad. Sci. USA* 87:3655–3659.

List of Patents and Patent Applications :
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110
U.S. Pat. No. 4,486,530
U.S. Pat. No. 4,683,195
U.S. Pat. No. 4,683,202
U.S. Pat. No. 4,816,567
U.S. Pat. No. 4,868,105
U.S. Pat. No. 5,252,479
EPO Publication No. 225,807
European Patent Application Publication No. 0332435
Geysen, H., PCT published application WO 84/03564, published 13 Sep. 1984
Hitzeman et al., EP 73,675A
PCT published application WO 93/07282

---

What is claimed is:

1. An isolated DNA coding for a BRCA1 polypeptide, said polypeptide having the amino acid sequence set forth in SEQ ID NO:2.

2. The isolated DNA of claim 1, wherein said DNA has the nucleotide sequence set forth in SEQ ID NO:1.

3. The isolated DNA of claim 1 which contains BRCA1 regulatory sequences.

4. The isolated DNA of claim 2 which contains BRCA1 regulatory sequences.

5. An isolated DNA having at least 15 nucleotides of the DNA of claim 1.

6. An isolated DNA having at least 15 nucleotides of the DNA of claim 2.

7. An isolated DNA selected from the group consisting of:
   (a) a DNA having the nucleotide sequence set forth in SEQ ID NO:1 having T at nucleotide position 4056;
   (b) a DNA having the nucleotide sequence set forth in SEQ ID NO:1 having an extra C at nucleotide position 5385;
   (c) a DNA having the nucleotide sequence set forth in SEQ ID NO: 1 having G at nucleotide position 5443; and, (d) a DNA having the nucleotide sequence set forth in SEQ ID NO:1 having 11 base pairs at nucleotide positions 189–199 deleted.

8. A replicative cloning vector which comprises the isolated DNA of claim 1 or parts thereof and a replicon operative in a host cell.

9. A replicative cloning vector which comprises the isolated DNA of claim 2 or parts thereof and a replicon operative in a host cell.

10. An expression system which comprises the isolated DNA of claim 1 or parts thereof operably linked to suitable control sequences.

11. An expression system which comprises the isolated DNA of claim 2 or parts thereof operably linked to suitable control sequences.

12. Host cells transformed with the expression system of claim 10.

13. Host cells transformed with the expression system of claim 11.

14. A method of producing BRCA1 polypeptide which comprises culturing the cells of claim 12 under conditions effective for the production of saod BRCA1 polypeptide and harvesting the BRCA1 polypeptide.

15. A method of producing BRCA1 polypeptide which comprises culturing the cells of claim 13 under conditions effective for the producton of said BRCA1 polypeptide and harvesting the BRCA1 polypeptide.

16. A pair of single-stranded DNA primers for determination of a nuycleotide sequence of a BRCA1 gene by a polymerase chin reaction, the sequence of said primers being derived from human chromosomne 17q, wherein the use of said primers in a polymerase chain reaction results in the synthesis of DNA having all or part of the sequence of the BRCA1 gene.

17. The pair of primers of claim 16 wherin said BRCA1 gene has the nucleotide sequence set forth in SEQ ID NO:1.

18. A kit for detecting mutations in the BRCA1 gene resulting in a susceptibility to breast and ovariann cancers comprising at least one oligonucleotide prime specific for a BRCA1 gene mutation and instructions relatiing to detectiong mutations in the BRCA1 gene.

19. A kit for detecting mutations in the BRCA1 gene resulting in a sisceptibility to breast and ovarian cancers comprising at least one allele-specific oligimucleotide probe for a BRCA1 gene mutation and instructions relating to detecting mutations in the BRCA1 gene.

20. A method for screening potential cancer therapeutics which comprises: growing a transformed eukaryotic host cell containing an altered BRCA1 gene causing cancer in the presence of a compound suspected of being a cancer therapeutic, growing said transformed eukaryotic host cell in the absence of said compound, determining the rate of growth of said host cell in the presence of said compound and the rate of growth of said host cell in the absence of said compound and comparing the growth rate of said host cells, wherein a slower rate of growth of said host cell in the presence of said compound is indicative of a cancer therapeutic.

* * * * *

UNITED STATES PATENT AND TRADEMARK OFFICE
CERTIFICATE OF CORRECTION

PATENT NO. : 5,747,282
DATED : May 5, 1998
INVENTOR(S) : Mark H. Skolnick et al.

It is certified that error appears in the above-identified patent and that said Letters Patent is hereby corrected as shown below:

Title page,
Please add the following references:
--

U.S. PATENT DOCUMENTS 5,236,844    08/1993    Basset et al.

FOREIGN PATENT DOCUMENTS

| | | |
|---|---|---|
| 0 518 650 | 12/1992 | European Patent Office |
| 91/09964 | 07/1991 | WO |
| 92/00311 | 01/1992 | WO |
| 92/11874 | 07/1992 | WO |
| 94/00764 | 01/1994 | WO |
| 95/19369 | 07/1995 | WO |

PUBLICATIONS

Castilla, L.H. et al. (1994). "Mutations in the BRCA 1 gene in families with early-onset breast and ovarian cancer," *Nature Genetics* 8:87-391.

Friedman, L.S. et al. (1994). "Confirmation of BRCA 1 by analysis of germline mutations linked to breast and ovarian cancer in ten families," *Nature Genetics* 8:399-404.

Goldgar, D.E. et al. (1994). "A Large Kindred With 17q-Linked Breast and Ovarian Cancer: Genetic, Pheotypic, and Genealogical Analysis," *J. Natl. Caner Institute* 86:200-209.

Liang P. et al. (1992). "Differential Display and Cloning of Messenger RNAs from Human Breast Cancer versus Mammary Epithelial Cells," Caner Researh 52:6966-6968.

Neuhausen, S.L. et al. (1994). "A P1-based physical map of the region from D17S776 to D17378 containing the breast cancer susceptibility gene BRCA1," *Hum. Mol. Gen.* 3:1919-1926.

Sato, T. et al. (1992). " The Human Prohibitin Gene Located on Chromosome 17q21 is Mutated in Sporadic Breast Cancer," Cancer Research 52:1543-1646.

UNITED STATES PATENT AND TRADEMARK OFFICE
CERTIFICATE OF CORRECTION

PATENT NO.    : 5,747,282
DATED         : May 5, 1998
INVENTOR(S)   : Mark. H. Skolnick et al.

It is certified that error appears in the above-identified patent and that said Letters Patent is hereby corrected as shown below:

Stampfer, M.R. et al. (1993). "Culture Systems for Study of Human Mammary Epithelial Cell Proliferation, Differentiation and Transformation," *Cancer Surveys* 18:7-34.

Wooster, R. et al. (1994). "Localization of a Breast Cancer Susceptibility Gene, BRCA2, to Chromosome 13q12-13," *Science* 265:2088-2090.

Albertsen, H., et al. (1994). "Genetic Mapping of the BRCA1 Region on Chromosome 17q21," *Am. J. Hum. Genet.* 54:516-525.

Anderson, D.E. (1972). "A Genetic Study of Human Breast Cancer," *J. Natl. Cancer Inst.* 48:1029-1034.

Arason, A., et al. (1993). "Linkage Analysis of Chromosome 17q markers and Breast-Ovarian Cancer in Icelandic Families, and Possible Relationship to Prostatic Cancer," Am. J. Hum. Genet. 52:711-717.

Bishop, T.D. and Gardner, E.J. (1980). "Analysis of the Genetic Predisposition to Cancer in Individual Pedigrees," Banbury Report 4: Cancer Incidence in Defined Populations, Cairns et al., eds., Cold Spring Harbor Laboratory, Cold Spring Harbor, New York, pp. 389-408.

Bishop, D.T., et al. (1988). "Segregation and Linkage Analysis of Nine Utah Breast Cancer Pedigrees," *Genet. Epidemiol.* 5:151-169.

Black, D.M., et al. (1993). "A Somatic Cell Hybrid Map of the Long Arm of Human Chromosome 17, Containing the Familial Breast Cancer Locus (BRCA1)," *Am. J. Hum. Genet.* 52:702-710.

Bowcock, A.M., et al. (1993). "THRA1 and D17S183 Flank an Interval of <4cM for the Breast-Ovarian Cancer Gene (BRCA1) on Chromosome 17q21," *Am. J. Hum. Genet.* 52: 718-722.

Boyd, J. (1995). "BRCA1: More than a hereditary breast cancer gene?" *Nature Genetics* 9:335-336.

Chamberlain. J.S., et al. (1993). "BRCA1 Maps Proximal to D17S579 on Chromosome 17q21 by Genetic Analysis," *Am. J. Hum. Genet.* 52:792-798.

UNITED STATES PATENT AND TRADEMARK OFFICE
CERTIFICATE OF CORRECTION

PATENT NO. : 5,747,282
DATED : May 5, 1998
INVENTOR(S) : Mark. H. Skolnick et al.

Page 3 of 6

It is certified that error appears in the above-identified patent and that said Letters Patent is hereby corrected as shown below:

Claus, E.B., et al. (1991). "Genetic Analysis of Breast Cancer in the Cancer and Steroid Hormone Study," *Am. J. Hum. Genet.* 48:232-242.

Cohen, B.B., et al. (1993). "Linkage of a Major Breast Cancer Gene to Chromosome 17q12-21: Results from 15 Edinburgh Families," *Am. J. Hum. Genet.* 52:723-729.

Devilee, P., et al. (1993). "Linkage to Markers for the Chromosome Region 17q12-q21 in 13 Dutch Breast Cancer Kindreds," *Am. J. Hum. Genet.* 52:730-735.

Dunphy, W.G. and Newport, J.W. (1989). "Fission Yeast p13 Blocks Mitotic Activation and Tyrosine Dephosphorylation of the Xenopus cdc2 Protein Kinase," *Cell* 58:181-191.

Easton, D.F., et al. (1993). "Genetic Linkage Analysis in Familial Breast and Ovarian Cancer: Results form 214 Families," *Am. J. Hum. Genet.* 52:678-701.

Fain, P.R. (1992). "Third international workshop on human chromosome 17 mapping," *Cytogen. Cell Genet.* 60:178-186.

Feunteun, J., et al. (1993). "A Breast-Ovarian Cancer Susceptibility Gene Maps to Chromosome 17q21," *Am. J. Hum. Genet.* 52:736-742.

Ford, D., et al. (1993). "The risks of cancer in BRCA1 mutation carriers," *Am. J. Hum. Genet. 53(supplement)*:abstract no. 298.

Futreal, P.A., et al. (1994). "*BRCA1* Mutations in Primary Breast and Ovarian Carcinomas," *Science 266*:120-122.

Goldgar, D.E., et al. (1993). "Chromosome 17q Linkage Studies of 18 Utah Breast Cancer Kindreds," *Am. J. Hum. Genet. 52*:743-748

Gould, K.L. and Nurse, P. (1989). "Tyrosine Phosphorylation of the fission yeast $cdc2^+$ protein kinase regulates entry into mitosis," *Nature 342*:39-45.

Hall, J.M., et al. (1990). "Linkage of Early-Onset Familial Breast Cancer to Chromosome 17q21," *Science 250*:1684-1689.

Hall, J.M., et al. (1992). "Closing in on a Breast Cancer Gene on Chromosome 17q," *Am. J. Hum. Genet. 50*:1235-1241.

UNITED STATES PATENT AND TRADEMARK OFFICE
CERTIFICATE OF CORRECTION

PATENT NO. : 5,747,282
DATED : May 5, 1998
INVENTOR(S) : Mark. H. Skolnick et al.

It is certified that error appears in the above-identified patent and that said Letters Patent is hereby corrected as shown below:

Hosking, L., et al. (1995). "A somatic *BRCA1* mutation in an ovarian tumour," *Nature Genetics 9*:343-344.

Ishibashi, T., et al. (1992). "Expression cloning of a human dual-specificity phosphatase," *Proc. Natl. Acad. Sci. USA 89*:12170-12174.

Kamb, A., et al. (1994). "Localization of the VHR Phosphatase Gene and Its Analysis as a Candidate for BRCA1," *Genomics 23*: 163-167.

Kumagai, A. and Dunphy, W.G. (1991). "The cdc25 Protein Controls Tyroosine Dephosphorylation of the cdc2 Protein in a Cell-Free system," *Cell 64*:903-914.

Lindblom, A., et al. (1993). "Linkage Analysis with Markers on 17q in 29 Swedish Breast Cancer Families," *Am. J. Hum. Genet. 52:*749-753.

Malkin, D., et al. (1990). "Germ Line p53 Mutations in a familial Syndrome of Breast Cancer, Sarcomas, and Other Neoplasms," *Science 250:*1233-1238.

Margaritte, P., et al. (1992). "Linkage of Familial Breast Cancer to Chromosome 17q21 May Not be Restricted to Early-Onset Disease," *Am. J. Hum. Genet. 50*: 1231-1234.

Mazoyer, S., et al. (1993). "Linkage Analysis of 19 French Breast Cancer Families, with Five Chromosome 17q Markers," *Am. J. Hum. Genet. 52:*754-760.

Merajver, S.D., et al. (1995). "Somatic mutation s in the *BRCA1* gene in sporadic ovarian tumours," *Nature Genetices 9:*439-443.

Miki, Y., et al. (1994). "A Strong Candidate for the Breast and Ovarian Cancer Susceptibility Gene *BRCA1*," *Science 266:*66-71.

Milner, B.J., et al. (1993). "Linkage "Studies with 17q and 18q Markers in a Breast/ Ovarian Cancer Family," *Am. J. Hum. Genet. 52:*761-766.

Narod, S.A., et al. (1991). "Familial breast-ovarian cancer locus on chromosome 17q12-q23," *Lancet 338:*82-83.

Newman, B. et al. (1988). "Inheritance of human breast cancer: Evidence for autosomal dominant transmission in high-risk families," *Proc. Natl. Acad. Sci. USA 85:*3044-3048.

UNITED STATES PATENT AND TRADEMARK OFFICE
CERTIFICATE OF CORRECTION

PATENT NO.    : 5,747,282
DATED         : May 5, 1998
INVENTOR(S)   : Mark. H. Skolnick et al.

It is certified that error appears in the above-identified patent and that said Letters Patent is hereby corrected as shown below:

O'Connell, P., et al. (1994). "A Radiation Hybrid Map of the BRCA1 Region," *Am. J. Hum. Genet. 54:*526-534.

Roberts, L. (1993). "Zeroing In on a Breast Cancer Susceptibility Gene," *Science 259:*622-625.

Shattuck-Eidens, D., et al. (1995). "A Collaborative Survey of 80 Mutations in the BRCA1 Breast and Ovarian Cancer Susceptibility Gene," JAMA *273:*535-541.

Simard, J., et al. (1994). "Common origins of BRCA1 mutations in Canadian breast and ovarian cancer families," *Nature Genetics 8:*392-398.

Smith, S.A., et al. (1992). "Allele losses in the region 17q12-21 in familial breast and ovarian cancer involve the wild-type chromosome," *Nature Genetics 2:*128-131.

Smith, S.A., et al. (1993). "Genetic Heterogeneity and Localization of a Familial Breast-Ovarian Cancer Gene on Chromosome 17q12-q21," *Am. J. Hum. Genet. 52:*767-776.

Spurr, N.K., et al. (1993). "Linkage Analysis of Early-Onset Breast and Ovarian Cancer Families, with Markers on the Long Arm of Chromosome 17," *Am. J. Hum. Genet. 52:*777-785.

Teare, M.D., et al. (1993). "A Linkage Study in Seven Breast Cancer Families," *Am. J. Hum. Genet. 52:*786-788.

Thompson, M.E., et al. (1995). "Decreased expression of *BRCA1* accelerates growth and is often present during sporadic breast cancer progression," *Nature Genetics 9:* 444-450.

Ullrich, A. and Schlessinger, J. (1990). "Signal Transductin by Receptors with Tyrosine Kinase Activity," *Cell 61:*203-212.

Williams, W.R. and Anderson, D.E. (1984). "Genetic Epidemiology of Breast Cancer: Segregation Analysis of 200 Danish Pedigrees," *Genet. Epidemiol. 1:*7-20.

Zimmerman, W., et al. (1993). "Linkage Analysis in German Breast Cancer Families with Early Onset of the Disease, Using Highly Polymorphic Markers from the Chromosome 17q11-q24 Region," *Am. J. Hum. Genet. 52:*789-791

UNITED STATES PATENT AND TRADEMARK OFFICE
CERTIFICATE OF CORRECTION

PATENT NO. : 5,747,282
DATED : May 5, 1998
INVENTOR(S) : Mark. H. Skolnick et al.

It is certified that error appears in the above-identified patent and that said Letters Patent is hereby corrected as shown below:

Go, R.C.P., et al. (1983). "Genetic Epidemiology of Breast Cancer and Associated Cancers in High-Risk Families. I. Segregation Analysis," *J. Natl. Cancer Inst.* 71:455-461. --;

Column 36,
Line 36, "collaborators" should be -- collaborators' --;

Column 155,
Line 17, "saod" should be -- said --.

Signed and Sealed this

Fourth Day of December, 2001

Attest:

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO. : 5,747,282  
APPLICATION NO. : 08/483554  
DATED : May 5, 1998  
INVENTOR(S) : Skolnick et al.

Page 1 of 1

It is certified that error appears in the above-identified patent and that said Letters Patent is hereby corrected as shown below:

Col. 155, Claim 16, line 24, please change "nuycleotide" to --nucleotide--.

Col. 155, Claim 16, line 25, please change "chin" to --chain--.

Col. 156, Claim 18, line 4, please change "ovariann" to --ovarian--.

Col. 156, Claim 18, line 5, please change "prime" to --primer--.

Col. 156, Claim 18, line 6, please change "detectiong" to --detecting--.

Col. 156, Claim 19, line 10, please change "sisceptibility" to --susceptibility--.

Col. 156, Claim 19, line 11, please change "oligimucleotide" to --oligonucleotide--.

Signed and Sealed this

Twenty-fourth Day of November, 2009

David J. Kappos  
*Director of the United States Patent and Trademark Office*